(12) United States Patent
Hakozaki et al.

(10) Patent No.: US 10,468,120 B2
(45) Date of Patent: *Nov. 5, 2019

(54) METHOD OF GENERATING A HYPERPIGMENTATION CONDITION GENE EXPRESSION SIGNATURE

(71) Applicant: The Procter & Gamble Company, Cincinnati, OH (US)

(72) Inventors: Tomohiro Hakozaki, Cincinnati, OH (US); Wenzhu Zhao, Mason, OH (US); Robert Lloyd Binder, Montgomery, OH (US); Jun Xu, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 162 days.

This patent is subject to a terminal disclaimer.

(21) Appl. No.: 13/851,873

(22) Filed: Mar. 27, 2013

(65) Prior Publication Data

US 2013/0261006 A1    Oct. 3, 2013

Related U.S. Application Data

(60) Provisional application No. 61/618,115, filed on Mar. 30, 2012.

(51) Int. Cl.
| | |
|---|---|
| *G01N 33/48* | (2006.01) |
| *G01N 33/50* | (2006.01) |
| *G16B 20/00* | (2019.01) |
| *C12Q 1/6881* | (2018.01) |
| *C12N 15/10* | (2006.01) |
| *C12Q 1/6883* | (2018.01) |
| *G16B 25/00* | (2019.01) |

(52) U.S. Cl.
CPC ......... *G16B 20/00* (2019.02); *C12N 15/1072* (2013.01); *C12Q 1/6881* (2013.01); *C12Q 1/6883* (2013.01); *G01N 33/5044* (2013.01); *C12Q 2600/148* (2013.01); *C12Q 2600/158* (2013.01); *G16B 25/00* (2019.02)

(58) Field of Classification Search
None
See application file for complete search history.

(56) References Cited

U.S. PATENT DOCUMENTS

| | | | |
|---|---|---|---|
| 3,755,560 | A | 8/1973 | Dickert et al. |
| 4,421,769 | A | 12/1983 | Dixon et al. |
| 4,677,120 | A | 6/1987 | Parish et al. |
| 4,885,311 | A | 12/1989 | Parish et al. |
| 5,049,584 | A | 9/1991 | Purcell et al. |
| 5,124,356 | A | 6/1992 | Purcell et al. |
| RE34,075 | E | 9/1992 | Purcell et al. |
| 2002/0169562 | A1 | 11/2002 | Stephanopoulos |
| 2007/0040306 | A1 | 2/2007 | Morel et al. |
| 2007/0205226 | A1 | 9/2007 | Honda et al. |
| 2008/0280844 | A1* | 11/2008 | Lessnick .............. C12Q 1/6886 514/44 A |
| 2009/0017080 | A1 | 1/2009 | Tanner et al. |
| 2010/0189669 | A1* | 7/2010 | Hakozaki ....................... 424/60 |
| 2010/0292085 | A1* | 11/2010 | Lum ................... G01N 33/5067 506/7 |
| 2011/0150798 | A1 | 6/2011 | Bacus |
| 2011/0269852 | A1* | 11/2011 | McDaniel ..................... 514/789 |
| 2012/0149773 | A1* | 6/2012 | Park ..................... A61K 31/203 514/552 |
| 2013/0165470 | A1* | 6/2013 | Isfort ................... A61K 31/439 514/289 |

FOREIGN PATENT DOCUMENTS

| | | |
|---|---|---|
| WO | WO 2003/100557 | 12/2003 |
| WO | WO 2005/040416 | 5/2005 |
| WO | 2012011904 A1 | 1/2012 |
| WO | 2012116081 A2 | 8/2012 |
| WO | WO2012116081 * | 8/2012 |
| WO | WO 2014/028572 | 2/2014 |

OTHER PUBLICATIONS

Affymetrix HGU133A 2.0 (release 33, submitted Oct. 30, 2012), Affymetrix.com.*
Hakozaki et al.(2002)British Journal of Dermatology 147.1 (2002): 20-31.*
Aoki et al. (British Journal of Dermatology 156.6 (2007): 1214-1223).*
Kang et al.( Journal of Investigative Dermatology (2011) 131, 1692-1700).*
Robinson et al.( J Am Acad Dermatol Sup 60 (2009)[Poster presentation]).*
Niacinamide Research Update, P&Gbeauty, uploaded 2011, pp. 1-6.*
Ozsolak et al. RNA sequencing: advances, challenges and opportunities. Nature Reviews Genetics, vol. 12, Feb. 2011, pp. 87-98. (Year: 2011).*
Yamaguchi et al. The regulation of skin pigmentation. The Journal of Biological Chemistry, vol. 282, pp. 27557-27561. (Year: 2007).*
Millikin, Cheri et al. "Topical N-acetyl glucosamine and niacinamide affect pigmentation relevant gene expression in in vitro geonomics experimentation" Journal American Acadamy of Dermatology, Feb. 2007.

(Continued)

Primary Examiner — Russell S Negin
(74) Attorney, Agent, or Firm — John G. Powell

(57) ABSTRACT

A method of generating a hyperpigmentation condition gene expression signature for use in identifying connections between perturbagens and genes associated with a skin pigmentation condition. The method includes providing a gene expression profile for a reference sample of human skin cells not affected with a pigmentation condition; generating a gene expression profile for a sample of human skin cells from a subject exhibiting the hyperpigmentation condition; comparing the expression profiles to determine a gene expression signature that includes a set of differentially expressed genes; assigning an identifier to each gene constituting the gene expression signature and ordering the identifiers according to the direction of differential expression to create one or more gene expression signature lists; and storing the one or more gene expression signature lists on at least one computer readable medium.

4 Claims, 73 Drawing Sheets

(56) References Cited

OTHER PUBLICATIONS

Bissett, Donald, et al. "Genomic Expression Changes Induced by Topical N-acetyl Glucosamine in Skin Equivalent Cultures in Vitro" Journal of Cosmetic Dermatology, 6 (4) :232-238;Dec. 2007.
Yumiko, I., et al. "Identification of Novel Hair-Growth Inducers by means of Connectivity Mapping", FASEB Journal, vol. 24, May 2010.
Hughes, T.R. et al. "Functional discovery via a compendium of expression profiles" Cell vol. 102, 109-126 (2000).
Jagetia G. C. et al, "Genotoxic Effect of Hydroquinone on the Cultured Mouse Spleenocytes"Toxicology Letter 121(1):15-20, 2001.
Lamb, Justin, et al. "Connectivity Map: Gene Expression Signatures to Connect Small Molecules, Genes, and Disease", Science, vol. 313, 2006.
M. Hollander et al. "Nonparametric Statistical Methods"; Wiley, New York, ed. 2, 1999 see, e.g., pp. 178-185.
Raynaud E. et al., "Depigmentation for cosmetic purposes: prevalence and side-effects in a female population in Senegal "Ann Dermatol Venereol 128(6-7):720-724, 2001 (abstract).
Shimizu K. et al., "The skin-lightening effects of artocarpin on UVB-induced pigmentation "Planta Med 68(1):79-81, 2002.
Sivapirabu, G. et al., "Topical Nicotinamide Modulates Cellular Energy Metabolism and Provides Broad-Spectrum Protection Against Ultraviolet Radiation-Induced Immunosuppression in Humans", British Journal of Dermatology 2009.
Subramanian,, A. et al, Gene set enrichment analysis: A knowledge-based approach for interpreting genome-wide expression profiles. (2005) Proc.Natl.Acad Sci U.S.A, 102, 15545-15550.
International Search Report; PCT/US2013/034055; dated Jun. 11, 2013; 17 pages.
International Search Report PCT/US2013/034052; dated Jun. 11, 2013; 18 pages.
International Search Report PCT/US2013/034054; dated Jun. 13, 2013; 18 pages.
International Search Report PCT/US2013/034117; dated Jun. 11, 2013; 17 pages.
Mills, K.J. "Dandruff/seborrhoeic dermatitis is characterized by an inflammatory genomic signature and possible immune dysfunction" Transcriptional Analysis of the condition and treatment effects of zinc pyrithione 2012 British Association of Dermatologists 166 (Suppl 2), pp. 33-40.
Mihaly, J. "Decreased retinoid concentration and retinoid signaling pathways in human atopic dermatitis" 2011 John Wiley & Sons, Experimental Dermatology, 20, pp. 326-330.
Ding-Dar, L. "Retinoid-Responsive Trascriptional Changes in Epidermal Keratinocytes" J. Cellular Physiology 220: pp. 427-329; 2009.
Guttman-Yassky E., et al., "Major differences in inflammatory dendritic cells and their products distinguish atopic dermatitis from psoriasis", J. Allergy Clin. Immunol., vol. 119, No. 5, pp. 1210-1217, May, 2007, USA.

* cited by examiner

FIG. 1

Table A: Pigmentation control targets and some Benchmark Agents

| Pigmentation Control Target Examples | Effective Agent Examples |
|---|---|
| Tyrosinase inhibition | Hydroquinone, resorcinols, kojic acid, arbutin, deoxy-arbutin, ascorbic acid (vitamin C) |
| Tyrosinase copper chelation | Ellagic acid, kojic acid |
| Inhibition of tyrosinase glycosylation | Glucosamine, N-acetyl glucosamine, tunicamycin |
| Melanosome transfer | Niacinamide, protease inhibitors |
| Inhibit binding of alpha-MSH to melanocyte | N-undecylenoyl-phenylalanine |
| Down regulation of tyrosinase | Retinoid (trans-retinoic acid, retinol and its esters, retinaldehyde) |
| Antioxidant | Vitamin C compounds, vitamin E, sulfhydryl compounds |
| Anti-inflammatory agent | Hydrocortisone, phytosterol, glycyrrhetinic acid, tranexamic acid, chamomile extract |
| Increase epidermal turnover | Retinoids, salicylic acid, alpha-hydroxy acids, alpha-keto acids, adenosine monophosphate |

FIG. 2A

Table B: Age Spot Signature; top 200 up-regulated

| Affy ID | Gene Symbol | Title | Public ID | p |
|---|---|---|---|---|
| 203941_at | INTS9 | integrator complex subunit 9 | NM_018250 | 0.00012 |
| 204736_s_at | CSPG4 | chondroitin sulfate proteoglycan 4 | NM_001897 | 0.00033 |
| 218567_x_at | DPP3 | dipeptidyl-peptidase 3 | NM_005700 | 0.00051 |
| 200630_x_at | SET | SET translocation (myeloid leukemia-associated) | AV702810 | 0.00059 |
| 207145_at | MSTN | myostatin | NM_005259 | 0.00060 |
| 214333_x_at | IDH3G | isocitrate dehydrogenase 3 (NAD+) gamma | U69268 | 0.00073 |
| 207365_x_at | USP34 | ubiquitin specific peptidase 34 | NM_014709 | 0.00096 |
| 217953_at | PHF3 | PHD finger protein 3 | AL050329 | 0.00097 |
| 217586_x_at | | | N35922 | 0.00100 |
| 215200_x_at | | UG0651E06 | AK022362 | 0.00120 |
| 202396_at | TCERG1 | transcription elongation regulator 1 | NM_006706 | 0.00123 |
| 203518_at | LYST | lysosomal trafficking regulator | NM_000081 | 0.00132 |
| 221692_s_at | MRPL34 | mitochondrial ribosomal protein L34 | AB049652 | 0.00157 |
| 202573_at | CSNK1G2 | casein kinase 1, gamma 2 | AL530441 | 0.00168 |
| 210232_at | CDC42 | cell division cycle 42 (GTP binding protein, 25kDa) | M35543 | 0.00184 |
| 202704_at | TOB1 | transducer of ERBB2, 1 | AA675892 | 0.00186 |
| 217040_x_at | SOX15 | SRY (sex determining region Y)-box 15 | AB025355 | 0.00188 |
| 217759_at | TRIM44 | tripartite motif-containing 44 | BF431488 | 0.00190 |
| 216859_x_at | | | AL080112 | 0.00254 |
| 212254_s_at | DST | dystonin | AI798790 | 0.00266 |
| 211464_x_at | CASP6 | caspase 6, apoptosis-related cysteine peptidase | U20537 | 0.00272 |
| 206765_at | KCNJ2 | potassium inwardly-rectifying channel, subfamily J, member 2 | AF153820 | 0.00287 |
| 200055_at | TAF10 | TAF10 RNA polymerase II, TATA box binding protein (TBP)-associated factor, 30kDa | NM_006284 | 0.00304 |
| 210547_x_at | ICA1 | islet cell autoantigen 1, 69kDa | L21181 | 0.00325 |
| 218394_at | ROGDI | rogdi homolog (Drosophila) | NM_024589 | 0.00328 |
| 201471_s_at | SQSTM1 | sequestosome 1 | NM_003900 | 0.00330 |
| 205555_s_at | MSX2 | msh homeobox 2 | D31771 | 0.00367 |
| 212143_s_at | IGFBP3 | insulin-like growth factor binding protein 3 | BF340228 | 0.00391 |
| 203029_s_at | PTPRN2 | protein tyrosine phosphatase, receptor type, N polypeptide 2 | NM_002847 | 0.00396 |
| 200771_at | LAMC1 | laminin, gamma 1 (formerly LAMB2) | NM_002293 | 0.00400 |
| 203057_s_at | PRDM2 | PR domain containing 2, with ZNF domain | AV724783 | 0.00415 |
| 200882_s_at | PSMD4 | proteasome (prosome, macropain) 26S subunit, non-ATPase, 4 | NM_002810 | 0.00429 |
| 214715_x_at | ZNF160 | zinc finger protein 160 | AK024789 | 0.00436 |
| 221219_s_at | KLHDC4 | kelch domain containing 4 | NM_017566 | 0.00437 |
| 202720_at | TES | testis derived transcript (3 LIM domains) | NM_015641 | 0.00474 |
| 202178_at | PRKCZ | protein kinase C, zeta | NM_002744 | 0.00500 |
| 220761_s_at | TAOK3 | TAO kinase 3 | NM_016281 | 0.00500 |
| 213582_at | ATP11A | ATPase, Class VI, type 11A | BF439472 | 0.00503 |

FIG. 2B

| Affy ID | Gene Symbol | Title | Public ID | p |
|---|---|---|---|---|
| 212454_x_at | HNRPDL | Heterogeneous nuclear ribonucleoprotein D-like | AI762552 | 0.00517 |
| 203247_s_at | ZNF24 | zinc finger protein 24 | BC003566 | 0.00519 |
| 203714_s_at | TBCE | tubulin folding cofactor E | NM_003193 | 0.00532 |
| 217916_s_at | FAM49B | family with sequence similarity 49, member B | NM_016623 | 0.00539 |
| 202049_s_at | ZMYM4 | zinc finger, MYM-type 4 | AA521508 | 0.00556 |
| 202468_s_at | CTNNAL1 | catenin (cadherin-associated protein), alpha-like 1 | NM_003798 | 0.00564 |
| 221737_at | GNA12 | guanine nucleotide binding protein (G protein) alpha 12 | AK024696 | 0.00569 |
| 207618_s_at | BCS1L | BCS1-like (yeast) | NM_004328 | 0.00572 |
| 205522_at | HOXD4 | homeobox D4 | NM_014621 | 0.00575 |
| 218082_s_at | UBP1 | upstream binding protein 1 (LBP-1a) | NM_014517 | 0.00576 |
| 210095_s_at | IGFBP3 | insulin-like growth factor binding protein 3 | M31159 | 0.00592 |
| 221802_s_at | KIAA1598 | KIAA1598 | AU157109 | 0.00603 |
| 214474_at | PRKAB2 | protein kinase, AMP-activated, beta 2 non-catalytic subunit | NM_005399 | 0.00606 |
| 204873_at | PEX1 | peroxisome biogenesis factor 1 | NM_000466 | 0.00610 |
| 222055_at | FAHD2A | fumarylacetoacetate hydrolase domain containing 2A | AA723370 | 0.00626 |
| 222055_at | FAHD2B | fumarylacetoacetate hydrolase domain containing 2B | AA723370 | 0.00626 |
| 200980_s_at | PDHA1 | pyruvate dehydrogenase (lipoamide) alpha 1 | NM_000284 | 0.00636 |
| 211945_s_at | ITGB1 | integrin, beta 1 (fibronectin receptor, beta polypeptide, antigen CD29 includes MDF2, MSK12) | BG500301 | 0.00649 |
| 201227_s_at | NDUFB8 | NADH dehydrogenase (ubiquinone) 1 beta subcomplex, 8, 19kDa | NM_005004 | 0.00652 |
| 220602_s_at | | | NM_025084 | 0.00652 |
| 204430_s_at | SLC2A5 | solute carrier family 2 (facilitated glucose/fructose transporter), member 5 | NM_003039 | 0.00655 |
| 205379_at | CBR3 | carbonyl reductase 3 | NM_001236 | 0.00661 |
| 204752_x_at | PARP2 | poly (ADP-ribose) polymerase family, member 2 | NM_005484 | 0.00681 |
| 217850_at | GNL3 | guanine nucleotide binding protein-like 3 (nucleolar) | NM_014366 | 0.00682 |
| 203637_s_at | MID1 | midline 1 (Opitz/BBB syndrome) | NM_000381 | 0.00683 |
| 201310_s_at | C5orf13 | chromosome 5 open reading frame 13 | NM_004772 | 0.00685 |
| 45572_s_at | GGA1 | golgi associated, gamma adaptin ear containing, ARF binding protein 1 | AW009695 | 0.00689 |
| 200027_at | NARS | asparaginyl-tRNA synthetase | NM_004539 | 0.00729 |
| 49679_s_at | MT1P3 | Metallothionein 1 pseudogene 3 | AA243774 | 0.00732 |
| 219231_at | TGS1 | trimethylguanosine synthase homolog (S. cerevisiae) | NM_024831 | 0.00737 |
| 215228_at | NHLH2 | nescient helix loop helix 2 | AA166895 | 0.00743 |
| 202124_s_at | TRAK2 | trafficking protein, kinesin binding 2 | AV705253 | 0.00754 |
| 219790_s_at | NPR3 | natriuretic peptide receptor C/guanylate cyclase C (atrionatriuretic peptide receptor C) | NM_000908 | 0.00821 |
| 210424_s_at | GOLGA8A | golgi autoantigen, golgin subfamily a, 8A | AF163441 | 0.00827 |
| 210424_s_at | GOLGA8B | golgi autoantigen, golgin subfamily a, 8B | AF163441 | 0.00827 |
| 219039_at | SEMA4C | sema domain, immunoglobulin domain (Ig), transmembrane domain (TM) and short cytoplasmic domain, (semaphorin) 4C | NM_017789 | 0.00835 |
| 215220_s_at | TPR | translocated promoter region (to activated MET oncogene) | AK023111 | 0.00835 |
| 209306_s_at | SWAP70 | SWAP-70 protein | AI139569 | 0.00837 |

FIG. 2C

| Affy ID | Gene Symbol | Title | Public ID | p |
|---|---|---|---|---|
| 202939_at | ZMPSTE24 | zinc metallopeptidase (STE24 homolog, S. cerevisiae) | NM_005857 | 0.00853 |
| 212987_at | FBXO9 | F-box protein 9 | AL031178 | 0.00858 |
| 211417_x_at | GGT1 | gamma-glutamyltransferase 1 | L20493 | 0.00868 |
| 206648_at | ZNF571 | zinc finger protein 571 | NM_016536 | 0.00883 |
| 211704_s_at | SPIN2B | spindlin family, member 2B | AF356353 | 0.00886 |
| 211704_s_at | SPIN2A | spindlin family, member 2A | AF356353 | 0.00886 |
| 221489_s_at | SPRY4 | sprouty homolog 4 (Drosophila) | W48843 | 0.00898 |
| 213376_at | ZBTB1 | zinc finger and BTB domain containing 1 | AI656706 | 0.00899 |
| 208374_s_at | CAPZA1 | capping protein (actin filament) muscle Z-line, alpha 1 | NM_006135 | 0.00902 |
| 201715_s_at | ACIN1 | apoptotic chromatin condensation inducer 1 | NM_014977 | 0.00905 |
| 48117_at | CCDC101 | coiled-coil domain containing 101 | AA160496 | 0.00907 |
| 201416_at | SOX4 | SRY (sex determining region Y)-box 4 | BG528420 | 0.00918 |
| 201810_s_at | SH3BP5 | SH3-domain binding protein 5 (BTK-associated) | AL562152 | 0.00931 |
| 221188_s_at | CIDEB | cell death-inducing DFFA-like effector b | NM_014430 | 0.00955 |
| 213140_s_at | SS18L1 | synovial sarcoma translocation gene on chromosome 18-like 1 | AB014593 | 0.00957 |
| 218612_s_at | TSSC4 | tumor suppressing subtransferable candidate 4 | NM_005706 | 0.00959 |
| 205286_at | TFAP2C | transcription factor AP-2 gamma (activating enhancer binding protein 2 gamma) | U85658 | 0.00978 |
| 207949_s_at | ICA1 | islet cell autoantigen 1, 69kDa | NM_004968 | 0.00978 |
| 200639_s_at | YWHAZ | tyrosine 3-monooxygenase/tryptophan 5-monooxygenase activation protein, zeta polypeptide | NM_003406 | 0.00982 |
| 201804_x_at | TBCB | tubulin folding cofactor B | NM_001281 | 0.01002 |
| 206217_at | EDA | ectodysplasin A | NM_001399 | 0.01014 |
| 205424_at | TBKBP1 | TBK1 binding protein 1 | NM_014726 | 0.01015 |
| 202220_at | KIAA0907 | KIAA0907 | NM_014949 | 0.01017 |
| 203274_at | F8A1 | coagulation factor VIII-associated (intronic transcript) 1 | NM_012151 | 0.01033 |
| 220051_at | PRSS21 | protease, serine, 21 (testisin) | NM_006799 | 0.01039 |
| 210153_s_at | ME2 | malic enzyme 2, NAD(+)-dependent, mitochondrial | M55905 | 0.01052 |
| 202123_s_at | ABL1 | v-abl Abelson murine leukemia viral oncogene homolog 1 | NM_005157 | 0.01061 |
| 207011_s_at | PTK7 | PTK7 protein tyrosine kinase 7 | NM_002821 | 0.01075 |
| 215672_s_at | KIAA0828 | adenosylhomocysteinase 3 | AK025372 | 0.01076 |
| 218946_at | NFU1 | NFU1 iron-sulfur cluster scaffold homolog (S. cerevisiae) | NM_015700 | 0.01083 |
| 215016_x_at | DST | dystonin | BC004912 | 0.01091 |
| 218856_at | TNFRSF21 | tumor necrosis factor receptor superfamily, member 21 | NM_016629 | 0.01101 |
| 201403_s_at | MGST3 | microsomal glutathione S-transferase 3 | NM_004528 | 0.01104 |
| 205811_at | POLG2 | polymerase (DNA directed), gamma 2, accessory subunit | NM_007215 | 0.01108 |
| 202860_at | DENND4B | DENN/MADD domain containing 4B | NM_014856 | 0.01126 |
| 35666_at | SEMA3F | sema domain, immunoglobulin domain (Ig), short basic domain, secreted, (semaphorin) 3F | U38276 | 0.01130 |
| 61734_at | RCN3 | reticulocalbin 3, EF-hand calcium binding domain | AI797684 | 0.01141 |
| 204751_x_at | DSC2 | desmocollin 2 | NM_004949 | 0.01143 |
| 217812_at | YTHDF2 | YTH domain family, member 2 | NM_016258 | 0.01161 |
| 210941_at | PCDH7 | protocadherin 7 | AB006756 | 0.01172 |

FIG. 2D

| Affx ID | Gene Symbol | Title | Public ID | p |
|---|---|---|---|---|
| 214604_at | HOXD11 | homeobox D11 | NM_021192 | 0.01176 |
| 218638_s_at | SPON2 | spondin 2, extracellular matrix protein | NM_012445 | 0.01182 |
| 217973_at | DCXR | dicarbonyl/L-xylulose reductase | NM_016286 | 0.01188 |
| 219007_at | NUP43 | nucleoporin 43kDa | NM_024647 | 0.01195 |
| 222136_x_at | ZNF43 | zinc finger protein 43 | AK022905 | 0.01206 |
| 217752_s_at | CNDP2 | CNDP dipeptidase 2 (metallopeptidase M20 family) | NM_018235 | 0.01211 |
| 204078_at | SC65 | synaptonemal complex protein SC65 | NM_006455 | 0.01233 |
| 218376_s_at | MICAL1 | microtubule associated monoxygenase, calponin and LIM domain containing 1 | NM_022765 | 0.01237 |
| 208820_at | PTK2 | PTK2 protein tyrosine kinase 2 | AL037339 | 0.01279 |
| 207060_at | EN2 | engrailed homeobox 2 | NM_001427 | 0.01282 |
| 202265_at | BMI1 | BMI1 polycomb ring finger oncogene | NM_005180 | 0.01310 |
| 219826_at | ZNF419 | zinc finger protein 419 | NM_024691 | 0.01335 |
| 204133_at | RRP9 | RRP9, small subunit (SSU) processome component, homolog (yeast) | NM_004704 | 0.01341 |
| 210652_s_at | C1orf34 | chromosome 1 open reading frame 34 | BC004399 | 0.01353 |
| 221974_at | IPW | Imprinted in Prader-Willi syndrome | AW770748 | 0.01355 |
| 210720_s_at | APBA2BP | amyloid beta (A4) precursor protein-binding, family A, member 2 binding protein | AB039947 | 0.01365 |
| 204525_at | PHF14 | PHD finger protein 14 | NM_014660 | 0.01366 |
| 221057_at | SPATA1 | spermatogenesis associated 1 | NM_022354 | 0.01378 |
| 217225_x_at | NOMO2 | NODAL modulator 2 | AL512687 | 0.0139 |
| 212281_s_at | TMEM97 | transmembrane protein 97 | BF038366 | 0.01392 |
| 203735_x_at | PPFIBP1 | PTPRF interacting protein, binding protein 1 (liprin beta 1) | N35896 | 0.01403 |
| 200775_s_at | HNRPK | heterogeneous nuclear ribonucleoprotein K | BC000355 | 0.01412 |
| 50277_at | GGA1 | golgi associated, gamma adaptin ear containing, ARF binding protein 1 | AW001443 | 0.01428 |
| 215828_at | | MRNA; cDNA DKFZp547C126 (from clone DKFZp547C126) | AL359599 | 0.01442 |
| 211609_x_at | PSMD4 | proteasome (prosome, macropain) 26S subunit, non-ATPase, 4 | U51007 | 0.01444 |
| 43977_at | TMEM161A | transmembrane protein 161A | AI660497 | 0.01453 |
| 218783_at | INTS7 | integrator complex subunit 7 | AL133049 | 0.01460 |
| 217317_s_at | | | AB002391 | 0.01470 |
| 209800_at | KRT16 | keratin 16 (focal non-epidermolytic palmoplantar keratoderma) | AF061812 | 0.01487 |
| 214594_x_at | ATP8B1 | ATPase, Class I, type 8B, member 1 | BG252666 | 0.01499 |
| 207688_s_at | INHBC | inhibin, beta C | NM_005538 | 0.01511 |
| 217409_at | MYO5A | myosin VA (heavy chain 12, myoxin) | Z22957 | 0.01511 |
| 203052_at | C2 | complement component 2 | NM_000063 | 0.01521 |
| 200001_at | CAPNS1 | calpain, small subunit 1 | NM_001749 | 0.01531 |
| 216973_s_at | HOXB7 | homeobox B7 | S49765 | 0.01535 |
| 65588_at | LOC388796 | hypothetical LOC388796 | AA827892 | 0.01552 |
| 214092_x_at | SFRS14 | splicing factor, arginine/serine-rich 14 | AI928127 | 0.01565 |
| 208994_s_at | PPIG | peptidylprolyl isomerase G (cyclophilin G) | AI638762 | 0.01572 |
| 202047_s_at | CBX6 | chromobox homolog 6 | AI458128 | 0.01595 |

FIG. 2E

| Affx ID | Gene Symbol | Title | Public ID | p |
|---|---|---|---|---|
| 202828_s_at | MMP14 | matrix metallopeptidase 14 (membrane-inserted) | NM_004995 | 0.01619 |
| 212977_at | CXCR7 | chemokine (C-X-C motif) receptor 7 | AI817041 | 0.01633 |
| 208613_s_at | FLNB | filamin B, beta (actin binding protein 278) | AV712733 | 0.01667 |
| 210005_at | GART | phosphoribosylglycinamide formyltransferase, phosphoribosylglycinamide synthetase, phosphoribosylaminoimidazole synthetase | D32051 | 0.01694 |
| 218095_s_at | TMEM165 | transmembrane protein 165 | NM_018475 | 0.01705 |
| 212911_at | DNAJC16 | DnaJ (Hsp40) homolog, subfamily C, member 16 | AB023179 | 0.01706 |
| 218984_at | PUS7 | pseudouridylate synthase 7 homolog (S. cerevisiae) | NM_019042 | 0.01712 |
| 202912_at | ADM | adrenomedullin | NM_001124 | 0.0172 |
| 202332_at | CSNK1E | casein kinase 1, epsilon | NM_001894 | 0.01741 |
| 218940_at | C14orf138 | chromosome 14 open reading frame 138 | NM_024558 | 0.01752 |
| 202115_s_at | NOC2L | nucleolar complex associated 2 homolog (S. cerevisiae) | NM_015658 | 0.01762 |
| 203468_at | CDK10 | cyclin-dependent kinase (CDC2-like) 10 | NM_003674 | 0.01774 |
| 33322_i_at | SFN | stratifin | X57348 | 0.01804 |
| 203201_at | PMM2 | phosphomannomutase 2 | NM_000303 | 0.01814 |
| 212561_at | RAB6IP1 | RAB6 interacting protein 1 | AA349595 | 0.01829 |
| 222169_x_at | SH2D3A | SH2 domain containing 3A | N71739 | 0.01829 |
| 212401_s_at | CDC2L2 | cell division cycle 2-like 2 (PITSLRE proteins) | AI767436 | 0.01831 |
| 200839_s_at | CTSB | cathepsin B | NM_001908 | 0.01846 |
| 214614_at | MNX1 | motor neuron and pancreas homeobox 1 | AI738662 | 0.01868 |
| 202128_at | KIAA0317 | KIAA0317 | NM_014821 | 0.01870 |
| 213359_at | HNRPD | Heterogeneous nuclear ribonucleoprotein D (AU-rich element RNA binding protein 1, 37kDa) | W74620 | 0.01887 |
| 220668_s_at | DNMT3B | DNA (cytosine-5-)-methyltransferase 3 beta | NM_006892 | 0.01902 |
| 214218_s_at | XIST | X (inactive)-specific transcript | AV699347 | 0.01906 |
| 212237_at | ASXL1 | additional sex combs like 1 (Drosophila) | N64780 | 0.01913 |
| 214123_s_at | C4orf10 | chromosome 4 open reading frame 10 | AI126492 | 0.01917 |
| 203502_at | BPGM | 2,3-bisphosphoglycerate mutase | NM_001724 | 0.01919 |
| 207730_x_at | | | NM_017932 | 0.01935 |
| 214787_at | DENND4A | DENN/MADD domain containing 4A | BE268538 | 0.01955 |
| 210235_s_at | PPFIA1 | protein tyrosine phosphatase, receptor type, f polypeptide (PTPRF), interacting protein (liprin), alpha 1 | U22815 | 0.01961 |
| 211729_x_at | BLVRA | biliverdin reductase A | BC005902 | 0.01962 |
| 210047_at | SLC11A2 | solute carrier family 11 (proton-coupled divalent metal ion transporters), member 2 | AF064484 | 0.01991 |
| 218294_s_at | NUP50 | nucleoporin 50kDa | AF267865 | 0.01994 |
| 203555_at | PTPN18 | protein tyrosine phosphatase, non-receptor type 18 (brain-derived) | NM_014369 | 0.02038 |
| 213672_at | MARS | methionyl-tRNA synthetase | AA621558 | 0.02045 |
| 209974_s_at | BUB3 | BUB3 budding uninhibited by benzimidazoles 3 homolog (yeast) | AF047473 | 0.02046 |
| 202248_at | E2F4 | E2F transcription factor 4, p107/p130-binding | BC000110 | 0.02049 |
| 212761_at | TCF7L2 | transcription factor 7-like 2 (T-cell specific, HMG-box) | AI949687 | 0.02051 |
| 202528_at | GALE | UDP-galactose-4-epimerase | NM_000403 | 0.02056 |

FIG. 2F

| Affy ID | Gene Symbol | Title | Public ID | p |
|---|---|---|---|---|
| 200077_s_at | OAZ1 | ornithine decarboxylase antizyme 1 | D87914 | 0.02077 |
| 209485_s_at | OSBPL1A | oxysterol binding protein-like 1A | W19983 | 0.02083 |
| 201850_at | CAPG | capping protein (actin filament), gelsolin-like | NM_001747 | 0.02091 |
| 208806_at | CHD3 | chromodomain helicase DNA binding protein 3 | BE379542 | 0.02097 |
| 74694_s_at | RABEP2 | rabaptin, RAB GTPase binding effector protein 2 | AA907940 | 0.02097 |
| 218002_s_at | CXCL14 | chemokine (C-X-C motif) ligand 14 | NM_004887 | 0.02102 |
| 206377_at | FOXF2 | forkhead box F2 | NM_001452 | 0.02102 |
| 203083_at | THBS2 | thrombospondin 2 | NM_003247 | 0.02115 |
| 217805_at | ILF3 | interleukin enhancer binding factor 3, 90kDa | NM_004516 | 0.02124 |
| 202245_at | LSS | lanosterol synthase (2,3-oxidosqualene-lanosterol cyclase) | AW084510 | 0.02136 |

FIG. 2G

Table C: Age Spot Signature; top 200 down-regulated

| Affy ID | Gene Symbol | Title | Public ID | p |
|---|---|---|---|---|
| 201401_s_at | ADRBK1 | adrenergic, beta, receptor kinase 1 | M80776 | 0.00005 |
| 205193_at | MAFF | v-maf musculoaponeurotic fibrosarcoma oncogene homolog F (avian) | NM_012323 | 0.00006 |
| 216221_s_at | PUM2 | pumilio homolog 2 (Drosophila) | D87078 | 0.00011 |
| 207206_s_at | ALOX12 | arachidonate 12-lipoxygenase | NM_000697 | 0.00013 |
| 209602_s_at | GATA3 | GATA binding protein 3 | AI796169 | 0.00016 |
| 203642_s_at | COBLL1 | COBL-like 1 | NM_014900 | 0.00025 |
| 210832_x_at | PTGER3 | prostaglandin E receptor 3 (subtype EP3) | D38298 | 0.00037 |
| 217589_at | RAB40A | RAB40A, member RAS oncogene family | AW300309 | 0.00048 |
| 217797_at | UFC1 | ubiquitin-fold modifier conjugating enzyme 1 | NM_016406 | 0.00049 |
| 201288_at | ARHGDIB | Rho GDP dissociation inhibitor (GDI) beta | NM_001175 | 0.00050 |
| 219416_at | SCARA3 | scavenger receptor class A, member 3 | NM_016240 | 0.00051 |
| 220892_s_at | PSAT1 | phosphoserine aminotransferase 1 | NM_021154 | 0.00053 |
| 208643_s_at | XRCC5 | X-ray repair complementing defective repair in Chinese hamster cells 5 (double-strand-break rejoining; Ku autoantigen, 80kDa) | J04977 | 0.00065 |
| 218841_at | ASB8 | ankyrin repeat and SOCS box-containing 8 | NM_024095 | 0.00067 |
| 200822_x_at | TPI1 | triosephosphate isomerase 1 | NM_000365 | 0.00072 |
| 201777_s_at | KIAA0494 | KIAA0494 | BC002525 | 0.00076 |
| 205568_at | AQP9 | aquaporin 9 | NM_020980 | 0.00078 |
| 212165_at | TMEM183A | transmembrane protein 183A | AF070537 | 0.00088 |
| 212165_at | TMEM183B | transmembrane protein 183B | AF070537 | 0.00088 |
| 206156_at | GJB5 | gap junction protein, beta 5 | NM_005268 | 0.00092 |
| 212638_s_at | WWP1 | WW domain containing E3 ubiquitin protein ligase 1 | BF131791 | 0.00098 |
| 209457_at | DUSP5 | dual specificity phosphatase 5 | U16996 | 0.00105 |
| 209976_s_at | CYP2E1 | cytochrome P450, family 2, subfamily E, polypeptide 1 | AF182276 | 0.00133 |
| 213764_s_at | MFAP5 | microfibrillar associated protein 5 | AW665892 | 0.00141 |
| 212588_at | PTPRC | protein tyrosine phosphatase, receptor type, C | Y00062 | 0.00143 |

FIG. 2H

| Affy ID | Gene Symbol | Title | Public ID | p |
|---|---|---|---|---|
| 213030_s_at | PLXNA2 | plexin A2 | AI688418 | 0.00147 |
| 219627_at | ZNF767 | zinc finger family member 767 | NM_024910 | 0.00155 |
| 202776_at | DNTTIP2 | deoxynucleotidyltransferase, terminal, interacting protein 2 | NM_014597 | 0.00164 |
| 213686_at | VPS13A | vacuolar protein sorting 13 homolog A (S. cerevisiae) | AI186145 | 0.00167 |
| 206038_s_at | NR2C2 | nuclear receptor subfamily 2, group C, member 2 | NM_003298 | 0.00172 |
| 205158_at | RNASE4 | ribonuclease, RNase A family, 4 | NM_002937 | 0.00178 |
| 206417_at | CNGA1 | cyclic nucleotide gated channel alpha 1 | NM_000087 | 0.00185 |
| 218190_s_at | UCRC | ubiquinol-cytochrome c reductase complex (7.2 kD) | NM_013387 | 0.00185 |
| 211942_x_at | RPL13A | ribosomal protein L13a | BF979419 | 0.00186 |
| 201879_at | ARIH1 | ariadne homolog, ubiquitin-conjugating enzyme E2 binding protein, 1 (Drosophila) | AI694332 | 0.00187 |
| 208485_x_at | CFLAR | CASP8 and FADD-like apoptosis regulator | NM_003879 | 0.00189 |
| 212433_x_at | RPS2 | ribosomal protein S2 | AA630314 | 0.00193 |
| 200869_at | RPL18A | ribosomal protein L18a | NM_000980 | 0.00200 |
| 208258_s_at | GAS2L1 | growth arrest-specific 2 like 1 | NM_006478 | 0.00215 |
| 216304_x_at | YME1L1 | YME1-like 1 (S. cerevisiae) | AJ295618 | 0.00218 |
| 201572_x_at | DCTD | dCMP deaminase | NM_001921 | 0.00221 |
| 218191_s_at | LMBRD1 | LMBR1 domain containing 1 | NM_018368 | 0.00238 |
| 211654_x_at | HLA-DQB1 | major histocompatibility complex, class II, DQ beta 1 | M17565 | 0.00239 |
| 203801_at | MRPS14 | mitochondrial ribosomal protein S14 | AA013164 | 0.0028 |
| 208370_s_at | RCAN1 | regulator of calcineurin 1 | NM_004414 | 0.00290 |
| 204502_at | SAMHD1 | SAM domain and HD domain 1 | NM_015474 | 0.00291 |
| 210299_s_at | FHL1 | four and a half LIM domains 1 | AF063002 | 0.00292 |
| 202454_s_at | ERBB3 | v-erb-b2 erythroblastic leukemia viral oncogene homolog 3 (avian) | NM_001982 | 0.00294 |
| 210756_s_at | NOTCH2 | Notch homolog 2 (Drosophila) | AF308601 | 0.00307 |
| 217837_s_at | VPS24 | vacuolar protein sorting 24 homolog (S. cerevisiae) | NM_016079 | 0.00308 |
| 205883_at | ZBTB16 | zinc finger and BTB domain containing 16 | NM_006006 | 0.00324 |
| 203000_at | STMN2 | stathmin-like 2 | BF967657 | 0.00327 |
| 205504_at | BTK | Bruton agammaglobulinemia tyrosine kinase | NM_000061 | 0.00331 |
| 202294_at | STAG1 | stromal antigen 1 | AI126490 | 0.00332 |
| 206114_at | EPHA4 | EPH receptor A4 | NM_004438 | 0.00334 |
| 213549_at | PDZD8 | PDZ domain containing 8 | AI890972 | 0.00336 |
| 214877_at | CDKAL1 | CDK5 regulatory subunit associated protein 1-like 1 | BE794663 | 0.00338 |
| 213264_at | PCBP2 | poly(rC) binding protein 2 | AW025150 | 0.00355 |
| 219349_s_at | EXOC2 | exocyst complex component 2 | NM_018303 | 0.00356 |
| 202716_at | PTPN1 | protein tyrosine phosphatase, non-receptor type 1 | NM_002827 | 0.00368 |
| 205067_at | IL1B | interleukin 1, beta | NM_000576 | 0.00379 |
| 210137_s_at | DCTD | dCMP deaminase | BC001286 | 0.00384 |
| 211749_s_at | VAMP3 | vesicle-associated membrane protein 3 (cellubrevin) | BC005941 | 0.00391 |
| 207114_at | LY6G6C | lymphocyte antigen 6 complex, locus G6C | NM_025261 | 0.00399 |
| 202371_at | TCEAL4 | transcription elongation factor A (SII)-like 4 | NM_024863 | 0.00401 |
| 217977_at | SEPX1 | selenoprotein X, 1 | NM_016332 | 0.00402 |

FIG. 2I

| Affy ID | Gene Symbol | Title | Public ID | p |
|---|---|---|---|---|
| 209111_at | RNF5 | ring finger protein 5 | BC004155 | 0.00404 |
| 215549_x_at | LOC643854 | similar to CTAGE family, member 5 | AC005587 | 0.00414 |
| 218024_at | BRP44L | brain protein 44-like | NM_016098 | 0.00426 |
| 216996_s_at | FASTKD2 | FAST kinase domains 2 | AK021557 | 0.00429 |
| 205590_at | RASGRP1 | RAS guanyl releasing protein 1 (calcium and DAG-regulated) | NM_005739 | 0.00433 |
| 218218_at | APPL2 | adaptor protein, phosphotyrosine interaction, PH domain and leucine zipper containing 2 | NM_018171 | 0.00439 |
| 212875_s_at | C21orf25 | chromosome 21 open reading frame 25 | AP001745 | 0.00443 |
| 205404_at | HSD11B1 | hydroxysteroid (11-beta) dehydrogenase 1 | NM_005525 | 0.00444 |
| 201682_at | PMPCB | peptidase (mitochondrial processing) beta | NM_004279 | 0.00449 |
| 203141_s_at | AP3B1 | adaptor-related protein complex 3, beta 1 subunit | AW058575 | 0.00468 |
| 209604_s_at | GATA3 | GATA binding protein 3 | BC003070 | 0.00468 |
| 210375_at | PTGER3 | prostaglandin E receptor 3 (subtype EP3) | X83858 | 0.00472 |
| 209373_at | MALL | mal, T-cell differentiation protein-like | BC003179 | 0.00476 |
| 210907_s_at | PDCD10 | programmed cell death 10 | BC002506 | 0.00480 |
| 219653_at | LSM14B | LSM14B, SCD6 homolog B (S. cerevisiae) | NM_014054 | 0.00480 |
| 204155_s_at | KIAA0999 | KIAA0999 protein | AA044154 | 0.00483 |
| 219681_s_at | RAB11FIP1 | RAB11 family interacting protein 1 (class I) | NM_025151 | 0.00499 |
| 213945_s_at | NUP210 | Nucleoporin 210kDa | AA909765 | 0.00506 |
| 209566_at | INSIG2 | insulin induced gene 2 | AL080184 | 0.00512 |
| 209292_at | ID4 | Inhibitor of DNA binding 4, dominant negative helix-loop-helix protein | AL022726 | 0.00515 |
| 202445_s_at | NOTCH2 | Notch homolog 2 (Drosophila) | NM_024408 | 0.00517 |
| 212573_at | ENDOD1 | endonuclease domain containing 1 | AF131747 | 0.00520 |
| 31637_s_at | NR1D1 | nuclear receptor subfamily 1, group D, member 1 | X72631 | 0.00534 |
| 31637_s_at | THRA | thyroid hormone receptor, alpha (erythroblastic leukemia viral (v-erb-a) oncogene homolog, avian) | X72631 | 0.00534 |
| 205128_x_at | PTGS1 | prostaglandin-endoperoxide synthase 1 (prostaglandin G/H synthase and cyclooxygenase) | NM_000962 | 0.00543 |
| 206628_at | SLC5A1 | solute carrier family 5 (sodium/glucose cotransporter), member 1 | NM_000343 | 0.00557 |
| 204718_at | EPHB6 | EPH receptor B6 | NM_004445 | 0.00562 |
| 216245_at | IL1RN | interleukin 1 receptor antagonist | BE563442 | 0.00564 |
| 212438_at | RY1 | putative nucleic acid binding protein RY-1 | BG252325 | 0.00571 |
| 215342_s_at | RABGAP1L | RAB GTPase activating protein 1-like | AB019490 | 0.00574 |
| 206265_s_at | GPLD1 | glycosylphosphatidylinositol specific phospholipase D1 | NM_001503 | 0.00583 |
| 200646_s_at | NUCB1 | nucleobindin 1 | NM_006184 | 0.00589 |
| 201412_at | LRP10 | low density lipoprotein receptor-related protein 10 | NM_014045 | 0.00590 |
| 211922_s_at | CAT | catalase | AY028632 | 0.00591 |
| 203641_s_at | COBLL1 | COBL-like 1 | BF002844 | 0.00592 |
| 38149_at | ARHGAP25 | Rho GTPase activating protein 25 | D29642 | 0.00596 |
| 204702_s_at | NFE2L3 | nuclear factor (erythroid-derived 2)-like 3 | NM_004289 | 0.00596 |
| 213531_s_at | RAB3GAP1 | RAB3 GTPase activating protein subunit 1 (catalytic) | AI040009 | 0.00597 |
| 212326_at | VPS13D | vacuolar protein sorting 13 homolog D (S. cerevisiae) | AB007922 | 0.00597 |

FIG. 2J

| Affy ID | Gene Symbol | Title | Public ID | p |
|---|---|---|---|---|
| 204454_at | LDOC1 | leucine zipper, down-regulated in cancer 1 | NM_012317 | 0.00598 |
| 210954_s_at | TSC22D2 | TSC22 domain family, member 2 | AF201292 | 0.00616 |
| 204782_at | | | NM_022443 | 0.00624 |
| 212716_s_at | EIF3K | eukaryotic translation initiation factor 3, subunit K | AW083133 | 0.00632 |
| 216570_x_at | LOC646417 | similar to 60S ribosomal protein L29 (P23) | AL096829 | 0.00650 |
| 217954_s_at | PHF3 | PHD finger protein 3 | NM_015153 | 0.00655 |
| 213497_at | ABTB2 | ankyrin repeat and BTB (POZ) domain containing 2 | AL050374 | 0.00666 |
| 212738_at | ARHGAP19 | Rho GTPase activating protein 19 | AV717623 | 0.00669 |
| 213234_at | KIAA1467 | KIAA1467 | AB040900 | 0.00672 |
| 203364_s_at | KIAA0652 | KIAA0652 | NM_014741 | 0.00679 |
| 206555_s_at | THUMPD1 | THUMP domain containing 1 | NM_017736 | 0.00699 |
| 208656_s_at | CCNI | cyclin I | AF135162 | 0.00704 |
| 37577_at | ARHGAP19 | Rho GTPase activating protein 19 | U79256 | 0.00708 |
| 218494_s_at | SLC2A4RG | SLC2A4 regulator | NM_020062 | 0.00713 |
| 214289_at | PSMB1 | Proteasome (prosome, macropain) subunit, beta type, 1 | W86293 | 0.00714 |
| 218034_at | FIS1 | fission 1 (mitochondrial outer membrane) homolog (S. cerevisiae) | NM_016068 | 0.00716 |
| 202995_s_at | FBLN1 | fibulin 1 | NM_006486 | 0.00721 |
| 214719_at | SLC46A3 | solute carrier family 46, member 3 | AK026720 | 0.00741 |
| 217272_s_at | SERPINB13 | serpin peptidase inhibitor, clade B (ovalbumin), member 13 | AJ001698 | 0.00746 |
| 208577_at | HIST1H3C | histone cluster 1, H3c | NM_003531 | 0.00748 |
| 213552_at | GLCE | glucuronic acid epimerase | W87398 | 0.00749 |
| 206076_at | LRRC23 | leucine rich repeat containing 23 | NM_006992 | 0.00759 |
| 212434_at | GRPEL1 | GrpE-like 1, mitochondrial (E. coli) | AI984421 | 0.00769 |
| 203843_at | RPS6KA3 | ribosomal protein S6 kinase, 90kDa, polypeptide 3 | AA906056 | 0.00772 |
| 205121_at | SGCB | sarcoglycan, beta (43kDa dystrophin-associated glycoprotein) | NM_000232 | 0.00772 |
| 217485_x_at | PMS2L1 | postmeiotic segregation increased 2-like 1 | D38435 | 0.00775 |
| 214945_at | NY-REN-7 | NY-REN-7 antigen | AW514267 | 0.00777 |
| 202959_at | MUT | methylmalonyl Coenzyme A mutase | AI433712 | 0.00784 |
| 213446_s_at | IQGAP1 | IQ motif containing GTPase activating protein 1 | AI679073 | 0.00786 |
| 205898_at | CX3CR1 | chemokine (C-X3-C motif) receptor 1 | U20350 | 0.00791 |
| 207143_at | CDK6 | cyclin-dependent kinase 6 | NM_001259 | 0.00814 |
| 212376_s_at | EP400 | E1A binding protein p400 | BE880591 | 0.00822 |
| 215813_s_at | PTGS1 | prostaglandin-endoperoxide synthase 1 (prostaglandin G/H synthase and cyclooxygenase) | S36219 | 0.00827 |
| 218820_at | C14orf132 | chromosome 14 open reading frame 132 | NM_020215 | 0.00827 |
| 218495_at | UXT | ubiquitously-expressed transcript | NM_004182 | 0.00831 |
| 218736_s_at | PALMD | palmdelphin | NM_017734 | 0.00858 |
| 212106_at | UBXD8 | UBX domain containing 8 | BF116183 | 0.00863 |
| 218266_s_at | FREQ | frequenin homolog (Drosophila) | NM_014286 | 0.00864 |
| 212135_s_at | ATP2B4 | ATPase, Ca++ transporting, plasma membrane 4 | AW517686 | 0.00869 |
| 212468_at | SPAG9 | sperm associated antigen 9 | AK023512 | 0.00888 |
| 203721_s_at | UTP18 | UTP18, small subunit (SSU) processome component, homolog (yeast) | NM_016001 | 0.00890 |

FIG. 2K

| Affy ID | Gene Symbol | Title | Public ID | p |
|---|---|---|---|---|
| 210790_s_at | SAR1A | SAR1 gene homolog A (S. cerevisiae) | BC003658 | 0.00894 |
| 203687_at | CX3CL1 | chemokine (C-X3-C motif) ligand 1 | NM_002996 | 0.00896 |
| 212649_at | DHX29 | DEAH (Asp-Glu-Ala-His) box polypeptide 29 | AL079292 | 0.00903 |
| 210418_s_at | IDH3B | isocitrate dehydrogenase 3 (NAD+) beta | AF023265 | 0.00918 |
| 212568_s_at | DLAT | dihydrolipoamide S-acetyltransferase (E2 component of pyruvate dehydrogenase complex) | BF978872 | 0.00924 |
| 218061_at | MEA1 | male-enhanced antigen 1 | NM_014623 | 0.00927 |
| 203045_at | NINJ1 | ninjurin 1 | NM_004148 | 0.00940 |
| 202675_at | SDHB | succinate dehydrogenase complex, subunit B, iron sulfur (Ip) | NM_003000 | 0.00943 |
| 211862_x_at | CFLAR | CASP8 and FADD-like apoptosis regulator | AF015451 | 0.00946 |
| 205538_at | CORO2A | coronin, actin binding protein, 2A | NM_003389 | 0.00979 |
| 200920_s_at | BTG1 | B-cell translocation gene 1, anti-proliferative | AL535380 | 0.00986 |
| 203236_s_at | LGALS9 | lectin, galactoside-binding, soluble, 9 (galectin 9) | NM_009587 | 0.00988 |
| 200657_at | SLC25A5 | solute carrier family 25 (mitochondrial carrier; adenine nucleotide translocator), member 5 | NM_001152 | 0.00990 |
| 208066_s_at | GTF2B | general transcription factor IIB | NM_001514 | 0.00994 |
| 210555_s_at | NFATC3 | nuclear factor of activated T-cells, cytoplasmic, calcineurin-dependent 3 | U85430 | 0.00998 |
| 218143_s_at | SCAMP2 | secretory carrier membrane protein 2 | NM_005697 | 0.01000 |
| 211596_s_at | LRIG1 | leucine-rich repeats and immunoglobulin-like domains 1 | AB050468 | 0.01001 |
| 203989_x_at | F2R | coagulation factor II (thrombin) receptor | NM_001992 | 0.01012 |
| 213455_at | FAM114A1 | family with sequence similarity 114, member A1 | W87466 | 0.01032 |
| 207018_s_at | RAB27B | RAB27B, member RAS oncogene family | NM_004163 | 0.01035 |
| 209877_at | SNCG | synuclein, gamma (breast cancer-specific protein 1) | AF010126 | 0.01039 |
| 210785_s_at | C1orf38 | chromosome 1 open reading frame 38 | AB035482 | 0.01046 |
| 200816_s_at | PAFAH1B1 | platelet-activating factor acetylhydrolase, isoform Ib, alpha subunit 45kDa | NM_000430 | 0.0107 |
| 202992_at | C7 | complement component 7 | NM_000587 | 0.01081 |
| 221787_at | C6orf120 | chromosome 6 open reading frame 120 | BF431618 | 0.01082 |
| 219010_at | C1orf106 | chromosome 1 open reading frame 106 | NM_018265 | 0.01107 |
| 204109_s_at | NFYA | nuclear transcription factor Y, alpha | NM_002505 | 0.01109 |
| 217833_at | SYNCRIP | synaptotagmin binding, cytoplasmic RNA interacting protein | AL520908 | 0.01109 |
| 203608_at | ALDH5A1 | aldehyde dehydrogenase 5 family, member A1 (succinate-semialdehyde dehydrogenase) | AL031230 | 0.01110 |
| 218807_at | VAV3 | vav 3 guanine nucleotide exchange factor | NM_006113 | 0.01111 |
| 204612_at | PKIA | protein kinase (cAMP-dependent, catalytic) inhibitor alpha | NM_006823 | 0.01123 |
| 208996_s_at | POLR2C | polymerase (RNA) II (DNA directed) polypeptide C, 33kDa | BC000409 | 0.01129 |
| 205220_at | GPR109B | G protein-coupled receptor 109B | NM_006018 | 0.01134 |
| 215393_s_at | COBLL1 | COBL-like 1 | AK002054 | 0.01136 |
| 204359_at | FLRT2 | fibronectin leucine rich transmembrane protein 2 | NM_013231 | 0.01143 |
| 203798_s_at | VSNL1 | visinin-like 1 | NM_003385 | 0.01148 |
| 202861_at | PER1 | period homolog 1 (Drosophila) | NM_002616 | 0.01182 |
| 201988_s_at | CREBL2 | cAMP responsive element binding protein-like 2 | BF438056 | 0.01183 |

FIG. 2L

| Affy ID | Gene Symbol | Title | Public ID | p |
|---|---|---|---|---|
| 203675_at | NUCB2 | nucleobindin 2 | NM_005013 | 0.01200 |
| 203934_at | KDR | kinase insert domain receptor (a type III receptor tyrosine kinase) | NM_002253 | 0.01203 |
| 212931_at | TCF20 | transcription factor 20 (AR1) | AB006630 | 0.01211 |
| 213400_s_at | TBL1X | transducin (beta)-like 1X-linked | AV753028 | 0.01216 |
| 213386_at | C9orf125 | chromosome 9 open reading frame 125 | AV726900 | 0.01216 |
| 209580_s_at | MBD4 | methyl-CpG binding domain protein 4 | AF114784 | 0.01221 |
| 202429_s_at | PPP3CA | protein phosphatase 3 (formerly 2B), catalytic subunit, alpha isoform | AL353950 | 0.01222 |
| 220797_at | METT10D | methyltransferase 10 domain containing | NM_024086 | 0.01223 |
| 215416_s_at | STOML2 | stomatin (EPB72)-like 2 | AC004472 | 0.01224 |
| 220413_at | SLC39A2 | solute carrier family 39 (zinc transporter), member 2 | NM_014579 | 0.01230 |
| 205349_at | GNA15 | guanine nucleotide binding protein (G protein), alpha 15 (Gq class) | NM_002068 | 0.01238 |
| 210260_s_at | TNFAIP8 | tumor necrosis factor, alpha-induced protein 8 | BC005352 | 0.01243 |
| 221527_s_at | PARD3 | par-3 partitioning defective 3 homolog (C. elegans) | AF196185 | 0.01244 |
| 208771_s_at | LTA4H | leukotriene A4 hydrolase | J02959 | 0.01262 |
| 218251_at | MID1IP1 | MID1 interacting protein 1 (gastrulation specific G12 homolog (zebrafish)) | NM_021242 | 0.01262 |
| 202022_at | ALDOC | aldolase C, fructose-bisphosphate | NM_005165 | 0.01265 |
| 207178_s_at | FRK | fyn-related kinase | NM_002031 | 0.01277 |
| 203240_at | FCGBP | Fc fragment of IgG binding protein | NM_003890 | 0.01280 |

FIG. 10A

Table D: Hexamidine Benchmark Signature: 100 up-regulated

| Affy ID | Gene Symbol | Title | Public ID | p |
|---|---|---|---|---|
| 217873_at | CAB39 | calcium binding protein 39 | NM_016289 | 0 |
| 201689_s_at | TPD52 | tumor protein D52 | BE974098 | 0.0 |
| 203370_s_at | PDLIM7 | PDZ and LIM domain 7 (enigma) | NM_005451 | 0.0 |
| 205281_s_at | PIGA | phosphatidylinositol glycan anchor biosynthesis, class A (paroxysmal nocturnal hemoglobinuria) | NM_002641 | 0.0 |
| 209939_x_at | CFLAR | CASP8 and FADD-like apoptosis regulator | AF005775 | 0.0 |
| 208651_x_at | CD24 | CD24 molecule | M58664 | 0.0 |
| 204214_s_at | RAB32 | RAB32, member RAS oncogene family | NM_006834 | 0.0 |
| 202672_s_at | ATF3 | activating transcription factor 3 | NM_001674 | 0.0 |
| 201466_s_at | JUN | jun oncogene | NM_002228 | 0.00001 |
| 202529_at | PRPSAP1 | phosphoribosyl pyrophosphate synthetase-associated protein 1 | NM_002766 | 0.00002 |
| 201617_x_at | CALD1 | caldesmon 1 | NM_004342 | 0.00002 |
| 209091_s_at | SH3GLB1 | SH3-domain GRB2-like endophilin B1 | AF263293 | 0.00003 |
| 201690_s_at | TPD52 | tumor protein D52 | AA524023 | 0.00003 |
| 209344_at | TPM4 | tropomyosin 4 | BC002827 | 0.00005 |
| 209210_s_at | PLEKHC1 | pleckstrin homology domain containing, family C (with FERM domain) member 1 | Z24725 | 0.00005 |
| 202324_s_at | ACBD3 | acyl-Coenzyme A binding domain containing 3 | NM_022735 | 0.00005 |
| 220327_at | VGLL3 | vestigial like 3 (Drosophila) | NM_016206 | 0.00006 |
| 205525_at | CALD1 | caldesmon 1 | NM_018495 | 0.00007 |
| 210945_at | COL4A6 | collagen, type IV, alpha 6 | BC005305 | 0.00008 |
| 205992_s_at | IL15 | interleukin 15 | NM_000585 | 0.00009 |
| 209566_at | INSIG2 | insulin induced gene 2 | AL080184 | 0.00009 |
| 212222_at | PSME4 | proteasome (prosome, macropain) activator subunit 4 | AU143855 | 0.00009 |
| 203741_s_at | ADCY7 | adenylate cyclase 7 | NM_001114 | 0.00010 |
| 204346_s_at | RASSF1 | Ras association (RalGDS/AF-6) domain family 1 | NM_007182 | 0.00011 |
| 200800_s_at | HSPA1B | heat shock 70kDa protein 1B | NM_005345 | 0.00011 |
| 200800_s_at | HSPA1A | heat shock 70kDa protein 1A | NM_005345 | 0.00011 |
| 204751_x_at | DSC2 | desmocollin 2 | NM_004949 | 0.00014 |
| 221994_at | PDLIM5 | PDZ and LIM domain 5 | AA196325 | 0.00015 |
| 209028_s_at | ABI1 | abl-interactor 1 | AF006516 | 0.00016 |
| 202147_s_at | IFRD1 | interferon-related developmental regulator 1 | NM_001550 | 0.00017 |
| 212112_s_at | STX12 | syntaxin 12 | AI816243 | 0.00017 |
| 202581_at | HSPA1B | heat shock 70kDa protein 1B | NM_005346 | 0.00020 |
| 201058_s_at | MYL9 | myosin, light chain 9, regulatory | NM_006097 | 0.00020 |
| 205020_s_at | ARL4A | ADP-ribosylation factor-like 4A | NM_005738 | 0.00022 |
| 220021_at | TMC7 | transmembrane channel-like 7 | NM_024847 | 0.00022 |
| 208960_s_at | KLF6 | Kruppel-like factor 6 | BE675435 | 0.00022 |
| 218303_x_at | KRCC1 | lysine-rich coiled-coil 1 | NM_016618 | 0.00023 |
| 207517_at | LAMC2 | laminin, gamma 2 | NM_018891 | 0.00025 |
| 211676_s_at | IFNGR1 | interferon gamma receptor 1 | AF056979 | 0.00026 |
| 212373_at | FEM1B | fem-1 homolog b (C. elegans) | AW139179 | 0.00031 |

FIG. 10B

| Affy ID | Gene Symbol | Title | Public ID | p |
|---|---|---|---|---|
| 212647_at | RRAS | related RAS viral (r-ras) oncogene homolog | NM_006270 | 0.00035 |
| 213281_at | JUN | Jun oncogene | BE327172 | 0.00036 |
| 218290_at | PLEKHJ1 | pleckstrin homology domain containing, family J member 1 | NM_018049 | 0.00036 |
| 203303_at | DYNLT3 | dynein, light chain, Tctex-type 3 | NM_006520 | 0.00038 |
| 202146_at | IFRD1 | interferon-related developmental regulator 1 | AA747426 | 0.00040 |
| 221269_s_at | SH3BGRL3 | SH3 domain binding glutamic acid-rich protein like 3 | NM_031286 | 0.00043 |
| 204091_at | PDE6D | phosphodiesterase 6D, cGMP-specific, rod, delta | NM_002601 | 0.00047 |
| 207574_s_at | GADD45B | growth arrest and DNA-damage-inducible, beta | NM_015675 | 0.00049 |
| 202552_s_at | CRIM1 | cysteine rich transmembrane BMP regulator 1 (chordin-like) | NM_016441 | 0.00049 |
| 219290_x_at | DAPP1 | dual adaptor of phosphotyrosine and 3-phosphoinositides | NM_014395 | 0.0005 |
| 204485_s_at | TOM1L1 | target of myb1 (chicken)-like 1 | NM_005486 | 0.00056 |
| 212099_at | RHOB | ras homolog gene family, member B | AI263909 | 0.00057 |
| 208394_x_at | ESM1 | endothelial cell-specific molecule 1 | NM_007036 | 0.00058 |
| 212763_at | CAMSAP1L1 | calmodulin regulated spectrin-associated protein 1-like 1 | AW593213 | 0.00059 |
| 202375_at | SEC24D | SEC24 related gene family, member D (S. cerevisiae) | NM_014822 | 0.00060 |
| 202538_s_at | CHMP2B | chromatin modifying protein 2B | NM_014043 | 0.00063 |
| 201669_s_at | MARCKS | myristoylated alanine-rich protein kinase C substrate | NM_002356 | 0.00066 |
| 202274_at | ACTG2 | actin, gamma 2, smooth muscle, enteric | NM_001615 | 0.00066 |
| 219988_s_at | C1orf164 | chromosome 1 open reading frame 164 | NM_018150 | 0.00069 |
| 213083_at | SLC35D2 | solute carrier family 35, member D2 | AJ005866 | 0.00078 |
| 208456_s_at | RRAS2 | related RAS viral (r-ras) oncogene homolog 2 | NM_012250 | 0.00083 |
| 203855_at | WDR47 | WD repeat domain 47 | NM_014969 | 0.00084 |
| 204094_s_at | TSC22D2 | TSC22 domain family, member 2 | NM_014779 | 0.00086 |
| 213102_at | ACTR3 | ARP3 actin-related protein 3 homolog (yeast) | Z78330 | 0.00087 |
| 208407_s_at | CTNND1 | catenin (cadherin-associated protein), delta 1 | NM_001331 | 0.00089 |
| 208865_at | CSNK1A1 | casein kinase 1, alpha 1 | BG534245 | 0.00091 |
| 200996_at | ACTR3 | ARP3 actin-related protein 3 homolog (yeast) | NM_005721 | 0.00095 |
| 210306_at | L3MBTL | l(3)mbt-like (Drosophila) | U89358 | 0.00095 |
| 218556_at | ORMDL2 | ORM1-like 2 (S. cerevisiae) | NM_014182 | 0.00103 |
| 219929_s_at | ZFYVE21 | zinc finger, FYVE domain containing 21 | NM_024071 | 0.00104 |
| 52164_at | C11orf24 | chromosome 11 open reading frame 24 | AA065185 | 0.00105 |
| 202619_s_at | PLOD2 | procollagen-lysine, 2-oxoglutarate 5-dioxygenase 2 | AI754404 | 0.00109 |
| 214085_x_at | GLIPR1 | GLI pathogenesis-related 1 (glioma) | AI912583 | 0.00111 |
| 201980_s_at | RSU1 | Ras suppressor protein 1 | NM_012425 | 0.00112 |
| 218501_at | ARHGEF3 | Rho guanine nucleotide exchange factor (GEF) 3 | NM_019555 | 0.00113 |
| 218260_at | C19orf58 | chromosome 19 open reading frame 58 | NM_024050 | 0.00113 |
| 202334_s_at | UBE2B | ubiquitin-conjugating enzyme E2B (RAD6 homolog) | AI768723 | 0.00125 |
| 215209_at | SEC24D | SEC24 related gene family, member D (S. cerevisiae) | AU143984 | 0.00127 |
| 218463_s_at | MUS81 | MUS81 endonuclease homolog (S. cerevisiae) | NM_025128 | 0.00128 |
| 202695_s_at | STK17A | serine/threonine kinase 17a | NM_004760 | 0.00137 |
| 202381_at | ADAM9 | ADAM metallopeptidase domain 9 (meltrin gamma) | NM_003816 | 0.00143 |
| 209379_s_at | KIAA1128 | KIAA1128 | AF241785 | 0.00168 |
| 205659_at | HDAC9 | histone deacetylase 9 | NM_014707 | 0.00175 |

FIG. 10C

| Affy ID | Gene Symbol | Title | Public ID | p |
|---|---|---|---|---|
| 200985_s_at | CD59 | CD59 molecule, complement regulatory protein | NM_000611 | 0.00178 |
| 218088_s_at | RRAGC | Ras-related GTP binding C | NM_022157 | 0.00179 |
| 36920_at | MTM1 | myotubularin 1 | U46024 | 0.00181 |
| 201328_at | ETS2 | v-ets erythroblastosis virus E26 oncogene homolog 2 (avian) | AL575509 | 0.00186 |
| 202627_s_at | SERPINE1 | serpin peptidase inhibitor, clade E (nexin, plasminogen activator inhibitor type 1), member 1 | AL574210 | 0.00193 |
| 201688_s_at | TPD52 | tumor protein D52 | BG389015 | 0.00201 |
| 205181_at | ZNF193 | zinc finger protein 193 | NM_006299 | 0.00208 |
| 211862_x_at | CFLAR | CASP8 and FADD-like apoptosis regulator | AF015451 | 0.00208 |
| 202269_x_at | GBP1 | guanylate binding protein 1, interferon-inducible, 67kDa | BC002666 | 0.00214 |
| 221803_s_at | NRBF2 | nuclear receptor binding factor 2 | AA883074 | 0.00221 |
| 218677_at | S100A14 | S100 calcium binding protein A14 | NM_020672 | 0.00222 |
| 208961_s_at | KLF6 | Kruppel-like factor 6 | AB017493 | 0.00224 |
| 205726_at | DIAPH2 | diaphanous homolog 2 (Drosophila) | NM_006729 | 0.00240 |
| 202822_at | LPP | LIM domain containing preferred translocation partner in lipoma | BF221852 | 0.00241 |
| 206504_at | CYP24A1 | cytochrome P450, family 24, subfamily A, polypeptide 1 | NM_000782 | 0.00263 |
| 211316_x_at | CFLAR | CASP8 and FADD-like apoptosis regulator | AF009616 | 0.00263 |
| 211984_at | CALM1 | calmodulin 1 (phosphorylase kinase, delta) | AI653730 | 0.00271 |
| 204017_at | KDELR3 | KDEL (Lys-Asp-Glu-Leu) endoplasmic reticulum protein retention receptor 3 | NM_006855 | 0.00273 |

FIG. 11A

Table E: Hexamidine Benchmark Signature; 100 top down-regulated

| Affy ID | Gene Symbol | Title | Public ID | p |
|---|---|---|---|---|
| 212242_at | TUBA4A | tubulin, alpha 4a | AL565074 | 0 |
| 212320_at | TUBB | tubulin, beta | BC001002 | 0.0 |
| 211714_x_at | TUBB | tubulin, beta | BC005838 | 0.0 |
| 208977_x_at | TUBB2C | tubulin, beta 2C | BC004188 | 0.0 |
| 209421_at | MSH2 | mutS homolog 2, colon cancer, nonpolyposis type 1 (E. coli) | U04045 | 0.0 |
| 213476_x_at | TUBB3 | tubulin, beta 3 | AL565749 | 0.00001 |
| 213476_x_at | MC1R | melanocortin 1 receptor (alpha melanocyte stimulating hormone receptor) | AL565749 | 0.00001 |
| 204254_s_at | VDR | vitamin D (1,25- dihydroxyvitamin D3) receptor | NM_000376 | 0.00002 |
| 213762_x_at | RBMX | RNA binding motif protein, X-linked | AI452524 | 0.00002 |
| 204255_s_at | VDR | vitamin D (1,25- dihydroxyvitamin D3) receptor | AA772285 | 0.00003 |
| 205677_s_at | DLEU1 | deleted in lymphocytic leukemia, 1 | NM_005887 | 0.00004 |
| 206157_at | PTX3 | pentraxin-related gene, rapidly induced by IL-1 beta | NM_002852 | 0.00005 |
| 201371_s_at | CUL3 | cullin 3 | AF062537 | 0.00006 |
| 218263_s_at | ZBED5 | zinc finger, BED-type containing 5 | NM_021211 | 0.00006 |
| 201376_s_at | HNRPF | heterogeneous nuclear ribonucleoprotein F | AI591354 | 0.00008 |
| 219885_at | SLFN12 | schlafen family member 12 | NM_018042 | 0.00008 |
| 208966_x_at | IFI16 | interferon, gamma-inducible protein 16 | AF208043 | 0.00013 |
| 211750_x_at | TUBA1C | tubulin, alpha 1c | BC005946 | 0.00013 |
| 204359_at | FLRT2 | fibronectin leucine rich transmembrane protein 2 | NM_013231 | 0.00014 |
| 211711_s_at | PTEN | phosphatase and tensin homolog (mutated in multiple advanced cancers 1) | BC005821 | 0.00016 |
| 208985_s_at | EIF3J | eukaryotic translation initiation factor 3, subunit J | BC002719 | 0.00016 |
| 218782_s_at | ATAD2 | ATPase family, AAA domain containing 2 | NM_014109 | 0.00017 |
| 209905_at | HOXA9 | homeobox A9 | AI246769 | 0.00017 |
| 218653_at | SLC25A15 | solute carrier family 25 (mitochondrial carrier; ornithine transporter) member 15 | NM_014252 | 0.00017 |
| 202690_s_at | SNRPD1 | small nuclear ribonucleoprotein D1 polypeptide 16kDa | BC001721 | 0.00018 |
| 218093_s_at | ANKRD10 | ankyrin repeat domain 10 | NM_017664 | 0.00018 |
| 209165_at | AATF | apoptosis antagonizing transcription factor | AF083208 | 0.00019 |
| 217990_at | GMPR2 | guanosine monophosphate reductase 2 | NM_016576 | 0.00020 |
| 209191_at | TUBB6 | tubulin, beta 6 | BC002654 | 0.00020 |
| 209251_x_at | TUBA1C | tubulin, alpha 1c | BC004949 | 0.00021 |
| 214651_s_at | HOXA9 | homeobox A9 | U41813 | 0.00021 |
| 204159_at | CDKN2C | cyclin-dependent kinase inhibitor 2C (p18, inhibits CDK4) | NM_001262 | 0.00023 |
| 205014_at | FGFBP1 | fibroblast growth factor binding protein 1 | NM_005130 | 0.00026 |
| 219198_at | GTF3C4 | general transcription factor IIIC, polypeptide 4, 90kDa | NM_012204 | 0.00027 |
| 220840_s_at | C1orf112 | chromosome 1 open reading frame 112 | NM_018186 | 0.00028 |
| 210110_x_at | HNRPH3 | heterogeneous nuclear ribonucleoprotein H3 (2H9) | AF132363 | 0.00028 |
| 204566_at | PPM1D | protein phosphatase 1D magnesium-dependent, delta isoform | NM_003620 | 0.00031 |
| 214431_at | GMPS | guanine monphosphate synthetase | NM_003875 | 0.00032 |

FIG. 11B

| Affy ID | Gene Symbol | Title | Public ID | p |
|---|---|---|---|---|
| 219015_s_at | ALG13 | asparagine-linked glycosylation 13 homolog (S. cerevisiae) | NM_018466 | 0.00033 |
| 216212_s_at | DKC1 | dyskeratosis congenita 1, dyskerin | AJ010395 | 0.00039 |
| 204544_at | HPS5 | Hermansky-Pudlak syndrome 5 | NM_007216 | 0.00043 |
| 205284_at | KIAA0133 | KIAA0133 | NM_014777 | 0.00043 |
| 202633_at | TOPBP1 | topoisomerase (DNA) II binding protein 1 | NM_007027 | 0.00044 |
| 212774_at | ZNF238 | zinc finger protein 238 | AJ223321 | 0.00046 |
| 202453_s_at | GTF2H1 | general transcription factor IIH, polypeptide 1, 62kDa | NM_005316 | 0.00046 |
| 211951_at | NOLC1 | nucleolar and coiled-body phosphoprotein 1 | D21262 | 0.00047 |
| 217850_at | GNL3 | guanine nucleotide binding protein-like 3 (nucleolar) | NM_014366 | 0.00053 |
| 202170_s_at | AASDHPPT | aminoadipate-semialdehyde dehydrogenase-phosphopantetheinyl transferase | AF151057 | 0.00053 |
| 217919_s_at | MRPL42 | mitochondrial ribosomal protein L42 | BE782148 | 0.00056 |
| 202469_s_at | CPSF6 | cleavage and polyadenylation specific factor 6, 68kDa | AU149367 | 0.00057 |
| 206332_s_at | IFI16 | interferon, gamma-inducible protein 16 | NM_005531 | 0.00058 |
| 212639_x_at | TUBA1B | tubulin, alpha 1b | AL581768 | 0.00058 |
| 208891_at | DUSP6 | dual specificity phosphatase 6 | BC003143 | 0.00059 |
| 31826_at | FKBP15 | FK506 binding protein 15, 133kDa | AB014574 | 0.00060 |
| 213859_x_at | SMARCA5 | SWI/SNF related, matrix associated, actin dependent regulator of chromatin, subfamily a, member 5 | AI652586 | 0.00060 |
| 205061_s_at | EXOSC9 | exosome component 9 | NM_005033 | 0.00061 |
| 211072_x_at | TUBA1B | tubulin, alpha 1b | BC006481 | 0.00062 |
| 211953_s_at | RANBP5 | RAN binding protein 5 | AU148466 | 0.00064 |
| 204772_s_at | TTF1 | transcription termination factor, RNA polymerase I | NM_007344 | 0.00065 |
| 212721_at | SFRS12 | splicing factor, arginine/serine-rich 12 | AI810380 | 0.00065 |
| 204084_s_at | CLN5 | ceroid-lipofuscinosis, neuronal 5 | AI911687 | 0.00066 |
| 201586_s_at | SFPQ | splicing factor proline/glutamine-rich (polypyrimidine tract binding protein associated) | NM_005066 | 0.00066 |
| 202983_at | HLTF | helicase-like transcription factor | AI760760 | 0.00067 |
| 202658_at | PEX11B | peroxisomal biogenesis factor 11B | NM_003846 | 0.00067 |
| 210793_s_at | NUP98 | nucleoporin 98kDa | U41815 | 0.00068 |
| 203284_s_at | HS2ST1 | heparan sulfate 2-O-sulfotransferase 1 | AW151887 | 0.00070 |
| 201274_at | PSMA5 | proteasome (prosome, macropain) subunit, alpha type, 5 | NM_002790 | 0.00072 |
| 208892_s_at | DUSP6 | dual specificity phosphatase 6 | BC003143 | 0.00076 |
| 203436_at | RPP30 | ribonuclease P/MRP 30kDa subunit | NM_006413 | 0.00077 |
| 218133_s_at | NIF3L1 | NIF3 NGG1 interacting factor 3-like 1 (S. pombe) | NM_021824 | 0.00079 |
| 218842_at | RPAP3 | RNA polymerase II associated protein 3 | NM_024604 | 0.00079 |
| 209773_s_at | RRM2 | ribonucleotide reductase M2 polypeptide | BC001886 | 0.00085 |
| 215813_s_at | PTGS1 | prostaglandin-endoperoxide synthase 1 (prostaglandin G/H synthase and cyclooxygenase) | S36219 | 0.00090 |
| 206104_at | ISL1 | ISL LIM homeobox 1 | NM_002202 | 0.0009 |
| 203689_s_at | FMR1 | fragile X mental retardation 1 | AI743037 | 0.00093 |
| 204662_at | CP110 | CP110 protein | NM_014711 | 0.00097 |
| 219862_s_at | NARF | nuclear prelamin A recognition factor | NM_012336 | 0.00097 |

FIG. 11C

| Affy ID | Gene Symbol | Title | Public ID | p |
|---|---|---|---|---|
| 201505_at | LAMB1 | laminin, beta 1 | NM_002291 | 0.00098 |
| 208840_s_at | G3BP2 | GTPase activating protein (SH3 domain) binding protein 2 | AU149503 | 0.00098 |
| 209384_at | PROSC | proline synthetase co-transcribed homolog (bacterial) | AA176833 | 0.00100 |
| 201386_s_at | DHX15 | DEAH (Asp-Glu-Ala-His) box polypeptide 15 | AF279891 | 0.00100 |
| 218564_at | RFWD3 | ring finger and WD repeat domain 3 | BC002574 | 0.00102 |
| 213133_s_at | GCSH | glycine cleavage system protein H (aminomethyl carrier) | AW237404 | 0.00106 |
| 211367_s_at | CASP1 | caspase 1, apoptosis-related cysteine peptidase (interleukin 1, beta, convertase) | U13699 | 0.00108 |
| 219987_at | LOC728193 | Hypothetical protein LOC728193 | NM_024534 | 0.00118 |
| 208801_at | SRP72 | signal recognition particle 72kDa | BE856385 | 0.00120 |
| 212515_s_at | DDX3X | DEAD (Asp-Glu-Ala-Asp) box polypeptide 3, X-linked | BG492602 | 0.00122 |
| 208863_s_at | SFRS1 | splicing factor, arginine/serine-rich 1 (splicing factor 2, alternate splicing factor) | M72709 | 0.00126 |
| 220651_s_at | MCM10 | minichromosome maintenance complex component 10 | NM_018518 | 0.00128 |
| 213294_at | | Full-length cDNA clone CS0DK002YF13 of HeLa cells Cot 25-normalized of Homo sapiens (human) | AV755522 | 0.00133 |
| 209585_s_at | MINPP1 | multiple inositol polyphosphate histidine phosphatase, 1 | AF084943 | 0.00133 |
| 203566_s_at | AGL | amylo-1, 6-glucosidase, 4-alpha-glucanotransferase (glycogen debranching enzyme, glycogen storage disease type III) | NM_000645 | 0.00135 |
| 218423_x_at | VPS54 | vacuolar protein sorting 54 homolog (S. cerevisiae) | NM_016516 | 0.00139 |
| 210460_s_at | PSMD4 | proteasome (prosome, macropain) 26S subunit, non-ATPase, 4 | AB033605 | 0.00139 |
| 213852_at | RBM8A | RNA binding motif protein 8A | BG289199 | 0.00139 |
| 212896_at | SKIV2L2 | superkiller viralicidic activity 2-like 2 (S. cerevisiae) | D29641 | 0.00142 |
| 219307_at | PDSS2 | prenyl (decaprenyl) diphosphate synthase, subunit 2 | NM_020381 | 0.00143 |
| 202486_at | AFG3L2 | AFG3 ATPase family gene 3-like 2 (yeast) | NM_006796 | 0.00144 |
| 218829_s_at | CHD7 | chromodomain helicase DNA binding protein 7 | NM_017780 | 0.00145 |
| 206122_at | SOX15 | SRY (sex determining region Y)-box 15 | NM_006942 | 0.00146 |
| 219178_at | QTRTD1 | queuine tRNA-ribosyltransferase domain containing 1 | NM_024638 | 0.00152 |

FIG. 12A

Table F: NAG Benchmark Signature; 39 significantly up-regulated

| Affy ID | Gene Symbol | Title | Public ID | p |
|---|---|---|---|---|
| 217212_s_at | IL9R | interleukin 9 receptor | Z84723 | 0.00190 |
| 210679_x_at | | | BC002629 | 0.00632 |
| 211316_x_at | CFLAR | CASP8 and FADD-like apoptosis regulator | AF009616 | 0.0073 |
| 211092_s_at | NF2 | neurofibromin 2 (bilateral acoustic neuroma) | AF122827 | 0.00977 |
| 219122_s_at | THG1L | tRNA-histidine guanylyltransferase 1-like (S. cerevisiae) | NM_017872 | 0.00990 |
| 201652_at | COPS5 | COP9 constitutive photomorphogenic homolog subunit 5 (Arabidopsis) | NM_006837 | 0.01071 |
| 209885_at | RHOD | ras homolog gene family, member D | BC001338 | 0.01148 |
| 205637_s_at | SH3GL3 | SH3-domain GRB2-like 3 | NM_003027 | 0.01236 |
| 208291_s_at | TH | tyrosine hydroxylase | NM_000360 | 0.01272 |
| 221355_at | CHRNG | cholinergic receptor, nicotinic, gamma | NM_005199 | 0.01519 |
| 218260_at | C19orf58 | chromosome 19 open reading frame 58 | NM_024050 | 0.01708 |
| 209438_at | PHKA2 | phosphorylase kinase, alpha 2 (liver) | AL096700 | 0.01768 |
| 209329_x_at | HIGD2A | HIG1 domain family, member 2A | BC000587 | 0.01925 |
| 217340_at | LOC645452 | similar to 60S ribosomal protein L21 | AL024509 | 0.02000 |
| 212885_at | MPHOSPH10 | M-phase phosphoprotein 10 (U3 small nucleolar ribonucleoprotein) | AL545921 | 0.02001 |
| 211538_s_at | HSPA2 | heat shock 70kDa protein 2 | U56725 | 0.02060 |
| 211842_s_at | SLC24A1 | solute carrier family 24 (sodium/potassium/calcium exchanger), member 1 | AF026132 | 0.02110 |
| 205215_at | RNF2 | ring finger protein 2 | NM_007212 | 0.02194 |
| 210685_s_at | UBE4B | ubiquitination factor E4B (UFD2 homolog, yeast) | AB028839 | 0.02333 |
| 213051_at | ZC3HAV1 | zinc finger CCCH-type, antiviral 1 | AI133727 | 0.02350 |
| 219759_at | LRAP | leukocyte-derived arginine aminopeptidase | NM_022350 | 0.02536 |
| 209099_x_at | JAG1 | jagged 1 (Alagille syndrome) | U73936 | 0.02560 |
| 213679_at | TTC30A | tetratricopeptide repeat domain 30A | AL049329 | 0.02639 |
| 219706_at | C20orf29 | chromosome 20 open reading frame 29 | NM_018347 | 0.02751 |
| 212396_s_at | KIAA0090 | KIAA0090 | AI143233 | 0.02888 |
| 200098_s_at | ANAPC5 | anaphase promoting complex subunit 5 | T33068 | 0.03148 |
| 218057_x_at | COX4NB | COX4 neighbor | NM_006067 | 0.03157 |
| 203936_s_at | MMP9 | matrix metallopeptidase 9 (gelatinase B, 92kDa gelatinase, 92kDa type IV collagenase) | NM_004994 | 0.03322 |
| 219406_at | C1orf50 | chromosome 1 open reading frame 50 | NM_024097 | 0.03424 |
| 212274_at | LPIN1 | lipin 1 | AV705559 | 0.03430 |
| 218807_at | VAV3 | vav 3 guanine nucleotide exchange factor | NM_006113 | 0.03548 |
| 206257_at | CCDC9 | coiled-coil domain containing 9 | NM_015603 | 0.03771 |
| 205232_s_at | PAFAH2 | platelet-activating factor acetylhydrolase 2, 40kDa | U89386 | 0.03778 |
| 200972_at | TSPAN3 | tetraspanin 3 | BC000704 | 0.03807 |
| 212608_s_at | | AF034176 Human mRNA (Tripodis and Ragoussis) Homo sapiens cDNA clone ntcon5 contig | W85912 | 0.03931 |

FIG. 12B

| Affy ID | Gene Symbol | Title | Public ID | p |
|---|---|---|---|---|
| 201600_at | PHB2 | prohibitin 2 | NM_007273 | 0.04080 |
| 218609_s_at | NUDT2 | nudix (nucleoside diphosphate linked moiety X)-type motif 2 | NM_001161 | 0.04750 |
| 214861_at | JMJD2C | jumonji domain containing 2C | AI341811 | 0.04757 |
| 213302_at | PFAS | phosphoribosylformylglycinamidine synthase (FGAR amidotransferase) | AL044326 | 0.04928 |

FIG. 13A

Table G: NAG Benchmark Signature, most significantly down-regulated

| Affy ID | Gene Symbol | Title | Public ID | p |
|---|---|---|---|---|
| 210735_s_at | CA12 | carbonic anhydrase XII | BC000278 | 0.00039 |
| 218686_s_at | RHBDF1 | rhomboid 5 homolog 1 (Drosophila) | NM_022450 | 0.00118 |
| 211487_x_at | RPS17 | ribosomal protein S17 | BC004886 | 0.00235 |
| 218176_at | MAGEF1 | melanoma antigen family F, 1 | NM_022149 | 0.00467 |
| 219885_at | SLFN12 | schlafen family member 12 | NM_018042 | 0.00508 |
| 202066_at | PPFIA1 | protein tyrosine phosphatase, receptor type, f polypeptide (PTPRF), interacting protein (liprin), alpha 1 | AA195259 | 0.00932 |
| 218871_x_at | GALNACT-2 | chondroitin sulfate GalNAcT-2 | NM_018590 | 0.00936 |
| 201375_s_at | PPP2CB | protein phosphatase 2 (formerly 2A), catalytic subunit, beta isoform | NM_004156 | 0.01239 |
| 212215_at | PREPL | prolyl endopeptidase-like | AB007896 | 0.01314 |
| 203537_at | PRPSAP2 | phosphoribosyl pyrophosphate synthetase-associated protein 2 | NM_002767 | 0.01544 |
| 204084_s_at | CLN5 | ceroid-lipofuscinosis, neuronal 5 | AI911687 | 0.01545 |
| 217310_s_at | FOXJ3 | forkhead box J3 | AK027075 | 0.01644 |
| 205457_at | C6orf106 | chromosome 6 open reading frame 106 | NM_024294 | 0.01816 |
| 214657_s_at | TncRNA | Trophoblast-derived noncoding RNA | AU134977 | 0.01950 |
| 201761_at | MTHFD2 | methylenetetrahydrofolate dehydrogenase (NADP+ dependent) 2, methenyltetrahydrofolate cyclohydrolase | NM_006636 | 0.01993 |
| 217783_s_at | YPEL5 | yippee-like 5 (Drosophila) | NM_016061 | 0.02115 |
| 217975_at | WBP5 | WW domain binding protein 5 | NM_016303 | 0.02119 |
| 217922_at | MAN1A2 | mannosidase, alpha, class 1A, member 2 | AL157902 | 0.02156 |
| 212644_s_at | C14orf32 | chromosome 14 open reading frame 32 | AJ671747 | 0.02257 |
| 212585_at | OSBPL8 | oxysterol binding protein-like 8 | BF970829 | 0.02269 |
| 218128_at | NFYB | nuclear transcription factor Y, beta | AU151875 | 0.02283 |
| 213027_at | TROVE2 | TROVE domain family, member 2 | AU146655 | 0.02388 |
| 209806_at | HIST1H2BK | histone cluster 1, H2bk | BC000893 | 0.02512 |
| 202014_at | PPP1R15A | protein phosphatase 1, regulatory (inhibitor) subunit 15A | NM_014330 | 0.02517 |
| 206662_at | GLRX | glutaredoxin (thioltransferase) | NM_002064 | 0.02560 |
| 219307_at | PDSS2 | prenyl (decaprenyl) diphosphate synthase, subunit 2 | NM_020381 | 0.02648 |
| 203103_s_at | PRPF19 | PRP19/PSO4 pre-mRNA processing factor 19 homolog (S. cerevisiae) | NM_014502 | 0.02765 |
| 211297_s_at | CDK7 | cyclin-dependent kinase 7 (MO15 homolog, Xenopus laevis, cdk-activating kinase) | L20320 | 0.02926 |
| 221471_at | SERINC3 | serine incorporator 3 | AW173623 | 0.02984 |
| 222162_s_at | ADAMTS1 | ADAM metallopeptidase with thrombospondin type 1 motif, 1 | AK023795 | 0.03078 |
| 218423_x_at | VPS54 | vacuolar protein sorting 54 homolog (S. cerevisiae) | NM_016516 | 0.03205 |
| 217803_at | GOLPH3 | golgi phosphoprotein 3 (coat-protein) | NM_022130 | 0.03452 |
| 203735_x_at | PPFIBP1 | PTPRF interacting protein, binding protein 1 (liprin beta 1) | N35896 | 0.03609 |
| 210608_s_at | FUT2 | fucosyltransferase 2 (secretor status included) | BC001899 | 0.03768 |
| 201453_x_at | RHEB | Ras homolog enriched in brain | NM_005614 | 0.03922 |
| 212450_at | KIAA0256 | KIAA0256 gene product | D87445 | 0.04008 |

FIG. 13B

| Affx_ID | Gene Symbol | Title | Public ID | p |
|---|---|---|---|---|
| 207524_at | ST7 | suppression of tumorigenicity 7 | NM_021908 | 0.04164 |
| 218068_s_at | ZNF672 | zinc finger protein 672 | NM_024836 | 0.04170 |
| 221864_at | ORAI3 | ORAI calcium release-activated calcium modulator 3 | AW517464 | 0.04438 |
| 211697_x_at | PNO1 | partner of NOB1 homolog (S. cerevisiae) | AF349314 | 0.04561 |
| 207826_s_at | ID3 | inhibitor of DNA binding 3, dominant negative helix-loop-helix protein | NM_002167 | 0.0457 |
| 204622_x_at | NR4A2 | nuclear receptor subfamily 4, group A, member 2 | NM_006186 | 0.04685 |
| 212688_at | PIK3CB | phosphoinositide-3-kinase, catalytic, beta polypeptide | BC003393 | 0.04925 |

FIG. 14A

Table H: Niacinamide Benchmark Signature, 100 top up-regulated

| Affy ID | Gene Symbol | Title | Public ID | P |
|---|---|---|---|---|
| 208025_s_at | HMGA2 | high mobility group AT-hook 2 | NM_003483 | 0.0 |
| 201129_at | SFRS7 | splicing factor, arginine/serine-rich 7, 35kDa | NM_006276 | 0.00002 |
| 210463_x_at | TRMT1 | TRM1 tRNA methyltransferase 1 homolog (S. cerevisiae) | BC002492 | 0.00003 |
| 202393_s_at | KLF10 | Kruppel-like factor 10 | NM_005655 | 0.00003 |
| 207618_s_at | BCS1L | BCS1-like (yeast) | NM_004328 | 0.00004 |
| 212099_at | RHOB | ras homolog gene family, member B | AI263909 | 0.00004 |
| 202672_s_at | ATF3 | activating transcription factor 3 | NM_001674 | 0.00005 |
| 200800_s_at | HSPA1A | heat shock 70kDa protein 1A | NM_005345 | 0.00006 |
| 200800_s_at | HSPA1B | heat shock 70kDa protein 1B | NM_005345 | 0.00006 |
| 202207_at | ARL4C | ADP-ribosylation factor-like 4C | BG435404 | 0.00009 |
| 216237_s_at | MCM5 | minichromosome maintenance complex component 5 | AA807529 | 0.00014 |
| 205466_s_at | HS3ST1 | heparan sulfate (glucosamine) 3-O-sulfotransferase 1 | NM_005114 | 0.00018 |
| 208083_s_at | ITGB6 | integrin, beta 6 | NM_000888 | 0.00023 |
| 211538_s_at | HSPA2 | heat shock 70kDa protein 2 | U56725 | 0.00025 |
| 205525_at | CALD1 | caldesmon 1 | NM_018495 | 0.00026 |
| 49329_at | KLHL22 | kelch-like 22 (Drosophila) | N38751 | 0.00027 |
| 200749_at | RAN | RAN, member RAS oncogene family | BF112006 | 0.00030 |
| 210511_s_at | INHBA | inhibin, beta A | M13436 | 0.00035 |
| 204610_s_at | CCDC85B | coiled-coil domain containing 85B | NM_006848 | 0.00036 |
| 215199_at | CALD1 | caldesmon 1 | AU147402 | 0.00043 |
| 36936_at | TSTA3 | tissue specific transplantation antigen P35B | U58766 | 0.00043 |
| 209344_at | TPM4 | tropomyosin 4 | BC002827 | 0.00050 |
| 204017_at | KDELR3 | KDEL (Lys-Asp-Glu-Leu) endoplasmic reticulum protein retention receptor 3 | NM_006855 | 0.00050 |
| 211060_x_at | GPAA1 | glycosylphosphatidylinositol anchor attachment protein 1 homolog (yeast) | BC006383 | 0.00050 |
| 207574_s_at | GADD45B | growth arrest and DNA-damage-inducible, beta | NM_015675 | 0.00053 |
| 207517_at | LAMC2 | laminin, gamma 2 | NM_018891 | 0.00063 |
| 209068_at | HNRPDL | heterogeneous nuclear ribonucleoprotein D-like | D89678 | 0.00065 |
| 204686_at | IRS1 | insulin receptor substrate 1 | NM_005544 | 0.00070 |
| 209099_x_at | JAG1 | jagged 1 (Alagille syndrome) | U73936 | 0.00071 |
| 200874_s_at | NOL5A | nucleolar protein 5A (56kDa with KKE/D repeat) | BE796327 | 0.00085 |
| 202016_at | MEST | mesoderm specific transcript homolog (mouse) | NM_002402 | 0.00086 |
| 219066_at | PPCDC | phosphopantothenoylcysteine decarboxylase | NM_021823 | 0.00093 |
| 204505_s_at | EPB49 | erythrocyte membrane protein band 4.9 (dematin) | NM_001978 | 0.00100 |
| 209067_s_at | HNRPDL | heterogeneous nuclear ribonucleoprotein D-like | D89092 | 0.00104 |
| 205020_s_at | ARL4A | ADP-ribosylation factor-like 4A | NM_005738 | 0.00111 |
| 205796_at | TCP11L1 | t-complex 11 (mouse)-like 1 | NM_018393 | 0.00126 |
| 202269_x_at | GBP1 | guanylate binding protein 1, interferon-inducible, 67kDa | BC002666 | 0.00129 |
| 207382_at | TP63 | tumor protein p63 | NM_003722 | 0.00133 |
| 212535_at | MEF2A | myocyte enhancer factor 2A | AA142929 | 0.00139 |

FIG. 14B

| Affy ID | Gene Symbol | Title | Public ID | P |
|---|---|---|---|---|
| 208990_s_at | HNRPH3 | heterogeneous nuclear ribonucleoprotein H3 (2H9) | AF132362 | 0.00143 |
| 212461_at | AZIN1 | antizyme inhibitor 1 | BF793951 | 0.00145 |
| 209210_s_at | PLEKHC1 | pleckstrin homology domain containing, family C (with FERM domain) member 1 | Z24725 | 0.00157 |
| 202246_s_at | CDK4 | cyclin-dependent kinase 4 | NM_000075 | 0.00160 |
| 218719_s_at | GINS3 | GINS complex subunit 3 (Psf3 homolog) | NM_022770 | 0.00168 |
| 211275_s_at | GYG1 | glycogenin 1 | AF087942 | 0.00177 |
| 52164_at | C11orf24 | chromosome 11 open reading frame 24 | AA065185 | 0.00178 |
| 41858_at | FRAG1 | FGF receptor activating protein 1 | AL049261 | 0.00179 |
| 220232_at | SCD5 | stearoyl-CoA desaturase 5 | NM_024906 | 0.0018 |
| 208960_s_at | KLF6 | Kruppel-like factor 6 | BE675435 | 0.00193 |
| 218809_at | PANK2 | pantothenate kinase 2 (Hallervorden-Spatz syndrome) | NM_024960 | 0.00196 |
| 219802_at | PYROXD1 | pyridine nucleotide-disulphide oxidoreductase domain 1 | NM_024854 | 0.00198 |
| 221009_s_at | ANGPTL4 | angiopoietin-like 4 | NM_016109 | 0.00204 |
| 218146_at | GLT8D1 | glycosyltransferase 8 domain containing 1 | NM_018446 | 0.00212 |
| 218652_s_at | PIGG | phosphatidylinositol glycan anchor biosynthesis, class G | NM_017733 | 0.00212 |
| 218616_at | INTS12 | integrator complex subunit 12 | NM_020395 | 0.00218 |
| 221703_at | BRIP1 | BRCA1 interacting protein C-terminal helicase 1 | AF360549 | 0.00225 |
| 218156_s_at | TSR1 | TSR1, 20S rRNA accumulation, homolog (S. cerevisiae) | NM_018128 | 0.0024 |
| 218167_at | AMZ2 | archaemetzincins-2 | NM_016627 | 0.00249 |
| 217873_at | CAB39 | calcium binding protein 39 | NM_016289 | 0.00264 |
| 216870_x_at | DLEU2 | deleted in lymphocytic leukemia, 2 | AF264787 | 0.00271 |
| 215766_at | GSTA1 | Glutathione S-transferase A1 | AL096729 | 0.00278 |
| 204346_s_at | RASSF1 | Ras association (RalGDS/AF-6) domain family 1 | NM_007182 | 0.00292 |
| 207850_at | CXCL3 | chemokine (C-X-C motif) ligand 3 | NM_002090 | 0.00296 |
| 202857_at | TMEM4 | transmembrane protein 4 | NM_014255 | 0.00308 |
| 215209_at | SEC24D | SEC24 related gene family, member D (S. cerevisiae) | AU143984 | 0.00311 |
| 218027_at | MRPL15 | mitochondrial ribosomal protein L15 | NM_014175 | 0.00312 |
| 200055_at | TAF10 | TAF10 RNA polymerase II, TATA box binding protein (TBP)-associated factor, 30kDa | NM_006284 | 0.00321 |
| 212829_at | PIP4K2A | phosphatidylinositol-5-phosphate 4-kinase, type II, alpha | BE878277 | 0.00327 |
| 214240_at | GAL | galanin | AL556409 | 0.00328 |
| 205659_at | HDAC9 | histone deacetylase 9 | NM_014707 | 0.00336 |
| 202581_at | HSPA1B | heat shock 70kDa protein 1B | NM_005346 | 0.00345 |
| 218358_at | CRELD2 | cysteine-rich with EGF-like domains 2 | NM_024324 | 0.00358 |
| 215532_x_at | ZNF492 | zinc finger protein 492 | AB040906 | 0.00367 |
| 204295_at | SURF1 | surfeit 1 | NM_003172 | 0.00395 |
| 212225_at | EIF1 | eukaryotic translation initiation factor 1 | AL516854 | 0.00397 |
| 221994_at | PDLIM5 | PDZ and LIM domain 5 | AA196325 | 0.00413 |
| 33736_at | STOML1 | stomatin (EPB72)-like 1 | Y16522 | 0.00414 |
| 206351_s_at | PEX10 | peroxisome biogenesis factor 10 | NM_002617 | 0.00418 |
| 201181_at | GNAI3 | guanine nucleotide binding protein (G protein), alpha inhibiting activity polypeptide 3 | NM_006496 | 0.00438 |

FIG. 14C

| Affy ID | Gene Symbol | Title | Public ID | P |
|---|---|---|---|---|
| 217150_s_at | NF2 | neurofibromin 2 (bilateral acoustic neuroma) | S73854 | 0.00442 |
| 201303_at | EIF4A3 | eukaryotic translation initiation factor 4A, isoform 3 | NM_014740 | 0.00451 |
| 209161_at | PRPF4 | PRP4 pre-mRNA processing factor 4 homolog (yeast) | AI184802 | 0.00452 |
| 218303_x_at | KRCC1 | lysine-rich coiled-coil 1 | NM_016618 | 0.00459 |
| 202208_s_at | ARL4C | ADP-ribosylation factor-like 4C | BC001051 | 0.00474 |
| 203370_s_at | PDLIM7 | PDZ and LIM domain 7 (enigma) | NM_005451 | 0.00476 |
| 202695_s_at | STK17A | serine/threonine kinase 17a | NM_004760 | 0.00486 |
| 220690_s_at | DHRS7B | dehydrogenase/reductase (SDR family) member 7B | NM_015510 | 0.00506 |
| 210034_s_at | RPL5 | ribosomal protein L5 | AA582460 | 0.00535 |
| 202726_at | LIG1 | ligase I, DNA, ATP-dependent | NM_000234 | 0.00550 |
| 211984_at | CALM1 | calmodulin 1 (phosphorylase kinase, delta) | AI653730 | 0.00561 |
| 213262_at | SACS | spastic ataxia of Charlevoix-Saguenay (sacsin) | AI932370 | 0.00562 |
| 219495_s_at | ZNF180 | zinc finger protein 180 | NM_013256 | 0.00566 |
| 213104_at | C16orf42 | chromosome 16 open reading frame 42 | AI799802 | 0.00574 |
| 221543_s_at | ERLIN2 | ER lipid raft associated 2 | AL442077 | 0.00578 |
| 201362_at | IVNS1ABP | influenza virus NS1A binding protein | AF205218 | 0.00589 |
| 220327_at | VGLL3 | vestigial like 3 (Drosophila) | NM_016206 | 0.00608 |
| 208961_s_at | KLF6 | Kruppel-like factor 6 | AB017493 | 0.00614 |
| 205584_at | CXorf45 | chromosome X open reading frame 45 | NM_024810 | 0.00614 |
| 218187_s_at | C8orf33 | chromosome 8 open reading frame 33 | NM_023080 | 0.00623 |
| 213984_at | PDS5A | PDS5, regulator of cohesion maintenance, homolog A (S. cerevisiae) | AW991219 | 0.00628 |
| 202787_s_at | MAPKAPK3 | mitogen-activated protein kinase-activated protein kinase 3 | U43784 | 0.00632 |

FIG. 15A

Table I: Niacinamide Benchmark Signature, 100 top down-regulated

| Affy ID | Gene Symbol | Title | Public ID | p |
|---|---|---|---|---|
| 212276_at | LPIN1 | lipin 1 | D80010 | 0 |
| 209146_at | SC4MOL | sterol-C4-methyl oxidase-like | AV704962 | 0.0 |
| 209218_at | SQLE | squalene epoxidase | AF098865 | 0.0 |
| 208881_x_at | IDI1 | isopentenyl-diphosphate delta isomerase 1 | BC005247 | 0.0 |
| 201626_at | INSIG1 | insulin induced gene 1 | BG292233 | 0.0 |
| 201170_s_at | BHLHB2 | basic helix-loop-helix domain containing, class B, 2 | NM_003670 | 0.0 |
| 219181_at | LIPG | lipase, endothelial | NM_006033 | 0.0 |
| 205014_at | FGFBP1 | fibroblast growth factor binding protein 1 | NM_005130 | 0.00001 |
| 201627_s_at | INSIG1 | insulin induced gene 1 | NM_005542 | 0.00001 |
| 219836_at | ZBED2 | zinc finger, BED-type containing 2 | NM_024508 | 0.00002 |
| 213359_at | HNRPD | Heterogeneous nuclear ribonucleoprotein D (AU-rich element RNA binding protein 1, 37kDa) | W74620 | 0.00002 |
| 205822_s_at | HMGCS1 | 3-hydroxy-3-methylglutaryl-Coenzyme A synthase 1 (soluble) | NM_002130 | 0.00003 |
| 202679_at | NPC1 | Niemann-Pick disease, type C1 | NM_000271 | 0.00005 |
| 209674_at | CRY1 | cryptochrome 1 (photolyase-like) | D83702 | 0.00005 |
| 208796_s_at | CCNG1 | cyclin G1 | BC000196 | 0.00006 |
| 202068_s_at | LDLR | low density lipoprotein receptor (familial hypercholesterolemia) | NM_000527 | 0.00006 |
| 202769_at | CCNG2 | cyclin G2 | AW134535 | 0.00007 |
| 219885_at | SLFN12 | schlafen family member 12 | NM_018042 | 0.00011 |
| 213562_s_at | SQLE | squalene epoxidase | BF979497 | 0.00012 |
| 222209_s_at | TMEM135 | transmembrane protein 135 | AK000684 | 0.00012 |
| 205282_at | LRP8 | low density lipoprotein receptor-related protein 8, apolipoprotein e receptor | NM_004631 | 0.00012 |
| 211559_s_at | CCNG2 | cyclin G2 | L49506 | 0.00013 |
| 218686_s_at | RHBDF1 | rhomboid 5 homolog 1 (Drosophila) | NM_022450 | 0.00014 |
| 206861_s_at | CGGBP1 | CGG triplet repeat binding protein 1 | NM_003663 | 0.00014 |
| 217783_s_at | YPEL5 | yippee-like 5 (Drosophila) | NM_016061 | 0.00015 |
| 209921_at | SLC7A11 | solute carrier family 7, (cationic amino acid transporter, y+ system) member 11 | AB040875 | 0.00016 |
| 201625_s_at | INSIG1 | insulin induced gene 1 | BE300521 | 0.00016 |
| 202220_at | KIAA0907 | KIAA0907 | NM_014949 | 0.00017 |
| 217993_s_at | MAT2B | methionine adenosyltransferase II, beta | NM_013283 | 0.00018 |
| 210950_s_at | FDFT1 | farnesyl-diphosphate farnesyltransferase 1 | BC003573 | 0.00019 |
| 221751_at | SLC2A3P1 | Solute carrier family 2 (facilitated glucose transporter), member 3 pseudogene 1 | AL565516 | 0.00025 |
| 203910_at | ARHGAP29 | Rho GTPase activating protein 29 | NM_004815 | 0.00027 |
| 213017_at | ABHD3 | abhydrolase domain containing 3 | AL534702 | 0.00029 |
| 217775_s_at | RDH11 | retinol dehydrogenase 11 (all-trans/9-cis/11-cis) | NM_016026 | 0.00029 |
| 208433_s_at | LRP8 | low density lipoprotein receptor-related protein 8, apolipoprotein e receptor | NM_017522 | 0.00037 |

FIG. 15B

| Affy ID | Gene Symbol | Title | Public ID | p |
|---|---|---|---|---|
| 209279_s_at | NSDHL | NAD(P) dependent steroid dehydrogenase-like | BC000245 | 0.00039 |
| 206247_at | MICB | MHC class I polypeptide-related sequence B | NM_005931 | 0.00042 |
| 212622_at | TMEM41B | transmembrane protein 41B | N64760 | 0.00043 |
| 209363_s_at | MED21 | mediator complex subunit 21 | U46837 | 0.00049 |
| 201790_s_at | DHCR7 | 7-dehydrocholesterol reductase | AW150953 | 0.00053 |
| 219129_s_at | SAP30L | SAP30-like | NM_024632 | 0.00058 |
| 219936_s_at | GPR87 | G protein-coupled receptor 87 | NM_023915 | 0.00061 |
| 217776_at | RDH11 | retinol dehydrogenase 11 (all-trans/9-cis/11-cis) | AF167438 | 0.00065 |
| 213094_at | GPR126 | G protein-coupled receptor 126 | AL033377 | 0.00072 |
| 205788_s_at | ZC3H11A | zinc finger CCCH-type containing 11A | NM_014827 | 0.00074 |
| 205904_at | MICA | MHC class I polypeptide-related sequence A | NM_000247 | 0.0008 |
| 218093_s_at | ANKRD10 | ankyrin repeat domain 10 | NM_017664 | 0.00090 |
| 212623_at | TMEM41B | transmembrane protein 41B | AU153138 | 0.00094 |
| 200832_s_at | SCD | stearoyl-CoA desaturase (delta-9-desaturase) | AB032261 | 0.00098 |
| 218842_at | RPAP3 | RNA polymerase II associated protein 3 | NM_024604 | 0.00114 |
| 209362_at | MED21 | mediator complex subunit 21 | AI688580 | 0.00120 |
| 216607_s_at | CYP51A1 | cytochrome P450, family 51, subfamily A, polypeptide 1 | U40053 | 0.00122 |
| 208647_at | FDFT1 | farnesyl-diphosphate farnesyltransferase 1 | AA872727 | 0.00122 |
| 217678_at | SLC7A11 | solute carrier family 7, (cationic amino acid transporter, y+ system) member 11 | AA488687 | 0.00128 |
| 201346_at | ADIPOR2 | adiponectin receptor 2 | NM_024551 | 0.00135 |
| 221582_at | HIST3H2A | histone cluster 3, H2a | BC001193 | 0.00135 |
| 218395_at | ACTR6 | ARP6 actin-related protein 6 homolog (yeast) | NM_022496 | 0.00137 |
| 210592_s_at | SAT1 | spermidine/spermine N1-acetyltransferase 1 | M55580 | 0.00141 |
| 203455_s_at | SAT1 | spermidine/spermine N1-acetyltransferase 1 | NM_002970 | 0.00142 |
| 218263_s_at | ZBED5 | zinc finger, BED-type containing 5 | NM_021211 | 0.00147 |
| 222262_s_at | ETNK1 | ethanolamine kinase 1 | AL137750 | 0.00153 |
| 216060_s_at | DAAM1 | dishevelled associated activator of morphogenesis 1 | AK021890 | 0.00159 |
| 219045_at | RHOF | ras homolog gene family, member F (in filopodia) | NM_019034 | 0.00174 |
| 208861_s_at | ATRX | alpha thalassemia/mental retardation syndrome X-linked (RAD54 homolog, S. cerevisiae) | U72937 | 0.00185 |
| 208964_s_at | FADS1 | fatty acid desaturase 1 | AL512760 | 0.00193 |
| 201276_at | RAB5B | RAB5B, member RAS oncogene family | AF267863 | 0.00201 |
| 209389_x_at | DBI | diazepam binding inhibitor (GABA receptor modulator, acyl-Coenzyme A binding protein) | M15887 | 0.00216 |
| 202604_x_at | ADAM10 | ADAM metallopeptidase domain 10 | NM_001110 | 0.00230 |
| 218258_at | POLR1D | polymerase (RNA) I polypeptide D, 16kDa | NM_015972 | 0.00253 |
| 201005_at | CD9 | CD9 molecule | NM_001769 | 0.00259 |
| 209681_at | SLC19A2 | solute carrier family 19 (thiamine transporter), member 2 | AF153330 | 0.00270 |
| 221255_s_at | TMEM93 | transmembrane protein 93 | NM_031298 | 0.00315 |
| 200863_s_at | RAB11A | RAB11A, member RAS oncogene family | AI215102 | 0.00334 |
| 213988_s_at | SAT1 | spermidine/spermine N1-acetyltransferase 1 | BE971383 | 0.00335 |
| 210290_at | ZNF174 | zinc finger protein 174 | BC001161 | 0.00345 |

FIG. 15C

| Affy ID | Gene Symbol | Title | Public ID | p |
|---|---|---|---|---|
| 210868_s_at | ELOVL6 | ELOVL family member 6, elongation of long chain fatty acids (FEN1/Elo2, SUR4/Elo3-like, yeast) | BC001305 | 0.00359 |
| 203925_at | GCLM | glutamate-cysteine ligase, modifier subunit | NM_002061 | 0.00363 |
| 204119_s_at | ADK | adenosine kinase | U90339 | 0.00378 |
| 203367_at | DUSP14 | dual specificity phosphatase 14 | NM_007026 | 0.00402 |
| 217975_at | WBP5 | WW domain binding protein 5 | NM_016303 | 0.00408 |
| 200620_at | TMEM59 | transmembrane protein 59 | NM_004872 | 0.00433 |
| 205376_at | INPP4B | inositol polyphosphate-4-phosphatase, type II, 105kDa | NM_003866 | 0.00436 |
| 212192_at | KCTD12 | potassium channel tetramerisation domain containing 12 | AI718937 | 0.00439 |
| 202067_s_at | LDLR | low density lipoprotein receptor (familial hypercholesterolemia) | AI861942 | 0.00457 |
| 221864_at | ORAI3 | ORAI calcium release-activated calcium modulator 3 | AW517464 | 0.00460 |
| 204044_at | QPRT | quinolinate phosphoribosyltransferase (nicotinate-nucleotide pyrophosphorylase (carboxylating)) | NM_014298 | 0.00481 |
| 215093_at | NSDHL | NAD(P) dependent steroid dehydrogenase-like | U82671 | 0.00492 |
| 209142_s_at | UBE2G1 | ubiquitin-conjugating enzyme E2G 1 (UBC7 homolog, yeast) | BC002775 | 0.00507 |
| 212602_at | WDFY3 | WD repeat and FYVE domain containing 3 | AI806395 | 0.00518 |
| 201928_at | PKP4 | plakophilin 4 | AA194254 | 0.00521 |
| 204342_at | SLC25A24 | solute carrier family 25 (mitochondrial carrier; phosphate carrier), member 24 | NM_013386 | 0.00527 |
| 202284_s_at | CDKN1A | cyclin-dependent kinase inhibitor 1A (p21, Cip1) | NM_000389 | 0.00535 |
| 201807_at | VPS26A | vacuolar protein sorting 26 homolog A (S. pombe) | NM_004896 | 0.00546 |
| 205000_at | DDX3Y | DEAD (Asp-Glu-Ala-Asp) box polypeptide 3, Y-linked | NM_004660 | 0.00559 |
| 201955_at | CCNC | cyclin C | AL137784 | 0.00563 |
| 202536_at | CHMP2B | chromatin modifying protein 2B | AK002165 | 0.00577 |
| 212589_at | RRAS2 | related RAS viral (r-ras) oncogene homolog 2 | AI753792 | 0.00581 |
| 206662_at | GLRX | glutaredoxin (thioltransferase) | NM_002064 | 0.00585 |
| 217127_at | CTH | cystathionase (cystathionine gamma-lyase) | AL354872 | 0.00590 |
| 210266_s_at | TRIM33 | tripartite motif-containing 33 | AF220137 | 0.00598 |

FIG. 16A

Table J: Sepiwhite Benchmark Signature; 100 top up-regulated

| Affy ID | Gene Symbol | Title | Public ID | p |
|---|---|---|---|---|
| 202708_s_at | HIST2H2BE | histone cluster 2, H2be | NM_003528 | 0.0 |
| 217528_at | CLCA2 | chloride channel, calcium activated, family member 2 | BF003134 | 0.0 |
| 202489_s_at | FXYD3 | FXYD domain containing ion transport regulator 3 | BC005238 | 0.00001 |
| 210609_s_at | TP53I3 | tumor protein p53 inducible protein 3 | BC000474 | 0.00001 |
| 208651_x_at | CD24 | CD24 molecule | M58664 | 0.00002 |
| 221922_at | GPSM2 | G-protein signaling modulator 2 (AGS3-like, C. elegans) | AW195581 | 0.00003 |
| 221211_s_at | C21orf7 | chromosome 21 open reading frame 7 | NM_020152 | 0.00005 |
| 210065_s_at | UPK1B | uroplakin 1B | AB002155 | 0.00006 |
| 201010_s_at | TXNIP | thioredoxin interacting protein | NM_006472 | 0.00006 |
| 217869_at | HSD17B12 | hydroxysteroid (17-beta) dehydrogenase 12 | NM_016142 | 0.00007 |
| 218983_at | C1RL | complement component 1, r subcomponent-like | NM_016546 | 0.00008 |
| 213725_x_at | XYLT1 | xylosyltransferase I | AI693140 | 0.00010 |
| 214702_at | FN1 | fibronectin 1 | AJ276395 | 0.00012 |
| 208025_s_at | HMGA2 | high mobility group AT-hook 2 | NM_003483 | 0.00016 |
| 204464_s_at | EDNRA | endothelin receptor type A | NM_001957 | 0.00017 |
| 78047_s_at | LOC729580 | hypothetical protein LOC729580 | AW001777 | 0.00019 |
| 219410_at | TMEM45A | transmembrane protein 45A | NM_018004 | 0.00019 |
| 203882_at | ISGF3G | interferon-stimulated transcription factor 3, gamma 48kDa | NM_006084 | 0.00021 |
| 219655_at | C7orf10 | chromosome 7 open reading frame 10 | NM_024728 | 0.00031 |
| 201312_s_at | SH3BGRL | SH3 domain binding glutamic acid-rich protein like | NM_003022 | 0.00036 |
| 218990_s_at | SPRR3 | small proline-rich protein 3 | NM_005416 | 0.00036 |
| 201916_s_at | SEC63 | SEC63 homolog (S. cerevisiae) | NM_007214 | 0.00044 |
| 200887_s_at | STAT1 | signal transducer and activator of transcription 1, 91kDa | NM_007315 | 0.00046 |
| 220945_x_at | MANSC1 | MANSC domain containing 1 | NM_018050 | 0.00048 |
| 220800_s_at | TMOD3 | tropomodulin 3 (ubiquitous) | NM_014547 | 0.00049 |
| 204469_at | PTPRZ1 | protein tyrosine phosphatase, receptor-type, Z polypeptide 1 | NM_002851 | 0.00050 |
| 212406_s_at | PCMTD2 | protein-L-isoaspartate (D-aspartate) O-methyltransferase domain containing 2 | AB028973 | 0.00053 |
| 215318_at | CG012 | hypothetical gene CG012 | AL049782 | 0.00054 |
| 202562_s_at | C14orf1 | chromosome 14 open reading frame 1 | AL136658 | 0.00056 |
| 205064_at | SPRR1A | small proline-rich protein 1A | NM_003125 | 0.00057 |
| 205064_at | SPRR1B | small proline-rich protein 1B (cornifin) | NM_003125 | 0.00057 |
| 222316_at | | Transcribed locus | AW973253 | 0.00057 |
| 211423_s_at | SC5DL | sterol-C5-desaturase (ERG3 delta-5-desaturase homolog, S. cerevisiae)-like | D85181 | 0.00084 |
| 221958_s_at | GPR177 | G protein-coupled receptor 177 | AA775681 | 0.00085 |
| 218432_at | FBXO3 | F-box protein 3 | NM_012175 | 0.00093 |
| 217188_s_at | C14orf1 | chromosome 14 open reading frame 1 | AC007182 | 0.00093 |
| 215729_s_at | VGLL1 | vestigial like 1 (Drosophila) | BE542323 | 0.00106 |
| 221208_s_at | C11orf61 | chromosome 11 open reading frame 61 | NM_024631 | 0.00116 |

FIG. 16B

| Affy ID | Gene Symbol | Title | Public ID | p |
|---|---|---|---|---|
| 208950_s_at | ALDH7A1 | aldehyde dehydrogenase 7 family, member A1 | BC002515 | 0.00116 |
| 218097_s_at | CUEDC2 | CUE domain containing 2 | NM_024040 | 0.00119 |
| 201814_at | TBC1D5 | TBC1 domain family, member 5 | AI300084 | 0.00121 |
| 218644_at | PLEK2 | pleckstrin 2 | NM_016445 | 0.00130 |
| 202480_s_at | DEDD | death effector domain containing | NM_004216 | 0.00130 |
| 213796_at | SPRR1A | small proline-rich protein 1A | AI923984 | 0.00132 |
| 218280_x_at | HIST2H2AA4 | histone cluster 2, H2aa4 | NM_003516 | 0.00137 |
| 218280_x_at | HIST2H2AA3 | histone cluster 2, H2aa3 | NM_003516 | 0.00137 |
| 209463_s_at | TAF12 | TAF12 RNA polymerase II, TATA box binding protein (TBP)-associated factor, 20kDa | D50544 | 0.00147 |
| 209576_at | GNAI1 | guanine nucleotide binding protein (G protein), alpha inhibiting activity polypeptide 1 | AL049933 | 0.00161 |
| 204967_at | SHROOM2 | shroom family member 2 | NM_001649 | 0.00163 |
| 209264_s_at | TSPAN4 | tetraspanin 4 | AF054841 | 0.00185 |
| 32069_at | N4BP1 | Nedd4 binding protein 1 | AB014515 | 0.00192 |
| 214720_x_at | 10-Sep | septin 10 | BF981643 | 0.00196 |
| 219494_at | RAD54B | RAD54 homolog B (S. cerevisiae) | NM_012415 | 0.002 |
| 218739_at | ABHD5 | abhydrolase domain containing 5 | NM_016006 | 0.00202 |
| 203691_at | PI3 | peptidase inhibitor 3, skin-derived (SKALP) | NM_002638 | 0.00204 |
| 204388_s_at | MAOA | monoamine oxidase A | NM_000240 | 0.00204 |
| 212282_at | TMEM97 | transmembrane protein 97 | BF038366 | 0.00206 |
| 203936_s_at | MMP9 | matrix metallopeptidase 9 (gelatinase B, 92kDa gelatinase, 92kDa type IV collagenase) | NM_004994 | 0.00211 |
| 217988_at | CCNB1IP1 | cyclin B1 interacting protein 1 | NM_021178 | 0.00213 |
| 213459_at | RPL37A | ribosomal protein L37a | AU155515 | 0.00215 |
| 201302_at | ANXA4 | annexin A4 | NM_001153 | 0.00230 |
| 200821_at | LAMP2 | lysosomal-associated membrane protein 2 | NM_013995 | 0.00240 |
| 221787_at | C6orf120 | chromosome 6 open reading frame 120 | BF431618 | 0.00244 |
| 203344_s_at | RBBP8 | retinoblastoma binding protein 8 | NM_002894 | 0.00247 |
| 219969_at | CXorf15 | chromosome X open reading frame 15 | NM_018360 | 0.00257 |
| 218138_at | MKKS | McKusick-Kaufman syndrome | NM_018848 | 0.00270 |
| 201469_s_at | SHC1 | SHC (Src homology 2 domain containing) transforming protein 1 | AI809967 | 0.00278 |
| 205659_at | HDAC9 | histone deacetylase 9 | NM_014707 | 0.00285 |
| 209885_at | RHOD | ras homolog gene family, member D | BC001338 | 0.00303 |
| 214290_s_at | HIST2H2AA3 | histone cluster 2, H2aa3 | AI313324 | 0.00312 |
| 214290_s_at | HIST2H2AA4 | histone cluster 2, H2aa4 | AI313324 | 0.00312 |
| 219929_s_at | ZFYVE21 | zinc finger, FYVE domain containing 21 | NM_024071 | 0.00321 |
| 203164_at | SLC33A1 | solute carrier family 33 (acetyl-CoA transporter), member 1 | BE464756 | 0.00326 |
| 205760_s_at | OGG1 | 8-oxoguanine DNA glycosylase | NM_016821 | 0.00340 |
| 201008_s_at | TXNIP | thioredoxin interacting protein | AA812232 | 0.00344 |
| 208951_at | ALDH7A1 | aldehyde dehydrogenase 7 family, member A1 | BC002515 | 0.00349 |
| 60474_at | C20orf42 | chromosome 20 open reading frame 42 | AA469071 | 0.00380 |
| 213787_s_at | EBP | emopamil binding protein (sterol isomerase) | AV702405 | 0.00385 |

FIG. 16C

| Affy ID | Gene Symbol | Title | Public ID | p |
|---|---|---|---|---|
| 203720_s_at | ERCC1 | excision repair cross-complementing rodent repair deficiency, complementation group 1 (includes overlapping antisense sequence) | NM_001983 | 0.00388 |
| 219979_s_at | C11orf73 | chromosome 11 open reading frame 73 | NM_016401 | 0.00408 |
| 204955_at | SRPX | sushi-repeat-containing protein, X-linked | NM_006307 | 0.00419 |
| 207785_s_at | RBPJ | recombination signal binding protein for immunoglobulin kappa J region | NM_015874 | 0.00425 |
| 217826_s_at | UBE2J1 | ubiquitin-conjugating enzyme E2, J1 (UBC6 homolog, yeast) | NM_016021 | 0.00431 |
| 218490_s_at | ZNF302 | zinc finger protein 302 | NM_018443 | 0.00432 |
| 215719_x_at | FAS | Fas (TNF receptor superfamily, member 6) | X83493 | 0.00442 |
| 218801_at | UGCGL2 | UDP-glucose ceramide glucosyltransferase-like 2 | NM_020121 | 0.00452 |
| 212672_at | ATM | ataxia telangiectasia mutated | U82828 | 0.00454 |
| 201009_s_at | TXNIP | thioredoxin interacting protein | AI439556 | 0.00455 |
| 212936_at | C5orf21 | chromosome 5 open reading frame 21 | AI927701 | 0.00455 |
| 201308_s_at | 11-Sep | septin 11 | NM_018243 | 0.00472 |
| 209608_s_at | ACAT2 | acetyl-Coenzyme A acetyltransferase 2 (acetoacetyl Coenzyme A thiolase) | BC000408 | 0.00480 |
| 219122_s_at | THG1L | tRNA-histidine guanylyltransferase 1-like (S. cerevisiae) | NM_017872 | 0.00491 |
| 218119_at | TIMM23B | translocase of inner mitochondrial membrane 23 homolog B (yeast) | NM_006327 | 0.00497 |
| 218119_at | TIMM23 | translocase of inner mitochondrial membrane 23 homolog (yeast) | NM_006327 | 0.00497 |
| 210317_s_at | YWHAE | tyrosine 3-monooxygenase/tryptophan 5-monooxygenase activation protein, epsilon polypeptide | U28936 | 0.00515 |
| 205667_at | WRN | Werner syndrome | NM_000553 | 0.00524 |
| 219763_at | DENND1A | DENN/MADD domain containing 1A | NM_024820 | 0.00524 |
| 218677_at | S100A14 | S100 calcium binding protein A14 | NM_020672 | 0.00540 |
| 219543_at | PBLD | phenazine biosynthesis-like protein domain containing | NM_022129 | 0.00573 |
| 201617_x_at | CALD1 | caldesmon 1 | NM_004342 | 0.00590 |
| 201185_at | HTRA1 | HtrA serine peptidase 1 | NM_002775 | 0.00603 |
| 203729_at | EMP3 | epithelial membrane protein 3 | NM_001425 | 0.00643 |
| 211801_x_at | MFN1 | mitofusin 1 | AF329637 | 0.00650 |
| 202321_at | GGPS1 | geranylgeranyl diphosphate synthase 1 | AW299507 | 0.00668 |

FIG. 17A

Table K: Sepiwhite Benchmark Signature; 100 top down-regulated

| Affy ID | Gene Symbol | Title | Public ID | p |
|---|---|---|---|---|
| 217767_at | LOC653879 | similar to Complement C3 precursor | NM_000064 | 0 |
| 208002_s_at | ACOT7 | acyl-CoA thioesterase 7 | NM_007274 | 0.00001 |
| 212501_at | CEBPB | CCAAT/enhancer binding protein (C/EBP), beta | AL564683 | 0.00002 |
| 209774_x_at | CXCL2 | chemokine (C-X-C motif) ligand 2 | M57731 | 0.00002 |
| 203925_at | GCLM | glutamate-cysteine ligase, modifier subunit | NM_002061 | 0.00002 |
| 201426_s_at | VIM | Vimentin | AI922599 | 0.00005 |
| 206343_s_at | NRG1 | neuregulin 1 | NM_013959 | 0.00005 |
| 204470_at | CXCL1 | chemokine (C-X-C motif) ligand 1 (melanoma growth stimulating activity, alpha) | NM_001511 | 0.00005 |
| 201491_at | AHSA1 | AHA1, activator of heat shock 90kDa protein ATPase homolog 1 (yeast) | NM_012111 | 0.00013 |
| 211940_x_at | H3F3A | H3 histone, family 3A | BE869922 | 0.00016 |
| 201839_s_at | TACSTD1 | tumor-associated calcium signal transducer 1 | NM_002354 | 0.00022 |
| 206157_at | PTX3 | pentraxin-related gene, rapidly induced by IL-1 beta | NM_002852 | 0.00029 |
| 209674_at | CRY1 | cryptochrome 1 (photolyase-like) | D83702 | 0.00031 |
| 204948_s_at | FST | follistatin | NM_013409 | 0.00041 |
| 201289_at | CYR61 | cysteine-rich, angiogenic inducer, 61 | NM_001554 | 0.00046 |
| 201381_x_at | CACYBP | calcyclin binding protein | AF057356 | 0.00047 |
| 204151_x_at | AKR1C1 | aldo-keto reductase family 1, member C1 (dihydrodiol dehydrogenase 1; 20-alpha (3-alpha)-hydroxysteroid dehydrogenase) | NM_001353 | 0.00057 |
| 201843_s_at | EFEMP1 | EGF-containing fibulin-like extracellular matrix protein 1 | NM_004105 | 0.00063 |
| 205067_at | IL1B | interleukin 1, beta | NM_000576 | 0.00068 |
| 200738_s_at | PGK1 | phosphoglycerate kinase 1 | NM_000291 | 0.00080 |
| 203667_at | TBCA | tubulin folding cofactor A | NM_004607 | 0.00081 |
| 201153_s_at | MBNL1 | muscleblind-like (Drosophila) | NM_021038 | 0.00103 |
| 200072_s_at | HNRPM | heterogeneous nuclear ribonucleoprotein M | AF061832 | 0.00112 |
| 201272_at | AKR1B1 | aldo-keto reductase family 1, member B1 (aldose reductase) | NM_001628 | 0.00130 |
| 209514_s_at | RAB27A | RAB27A, member RAS oncogene family | BE502030 | 0.00145 |
| 205476_at | CCL20 | chemokine (C-C motif) ligand 20 | NM_004591 | 0.00151 |
| 201338_x_at | GTF3A | general transcription factor IIIA | NM_002097 | 0.00159 |
| 218309_at | CAMK2N1 | calcium/calmodulin-dependent protein kinase II inhibitor 1 | NM_018584 | 0.00167 |
| 205774_at | F12 | coagulation factor XII (Hageman factor) | NM_000505 | 0.00211 |
| 204181_s_at | ZBTB43 | zinc finger and BTB domain containing 43 | T90308 | 0.00214 |
| 204078_at | SC65 | synaptonemal complex protein SC65 | NM_006455 | 0.00227 |
| 201463_s_at | TALDO1 | transaldolase 1 | NM_006755 | 0.00227 |
| 208746_x_at | ATP5L | ATP synthase, H+ transporting, mitochondrial F0 complex, subunit G | AF070655 | 0.00231 |
| 208700_s_at | TKT | transketolase (Wernicke-Korsakoff syndrome) | L12711 | 0.00237 |
| 200852_x_at | GNB2 | guanine nucleotide binding protein (G protein), beta polypeptide 2 | NM_005273 | 0.00240 |

FIG. 17B

| Affy ID | Gene Symbol | Title | Public ID | p |
|---|---|---|---|---|
| 201274_at | PSMA5 | proteasome (prosome, macropain) subunit, alpha type, 5 | NM_002790 | 0.00246 |
| 219017_at | ETNK1 | ethanolamine kinase 1 | NM_018638 | 0.00246 |
| 206247_at | MICB | MHC class I polypeptide-related sequence B | NM_005931 | 0.00267 |
| 208934_s_at | LGALS8 | lectin, galactoside-binding, soluble, 8 (galectin 8) | AF342815 | 0.00268 |
| 207345_at | FST | follistatin | NM_006350 | 0.00295 |
| 217997_at | PHLDA1 | pleckstrin homology-like domain, family A, member 1 | AI795908 | 0.00314 |
| 211668_s_at | PLAU | plasminogen activator, urokinase | K03226 | 0.00320 |
| 219933_at | GLRX2 | glutaredoxin 2 | NM_016066 | 0.00338 |
| 202066_at | PPFIA1 | protein tyrosine phosphatase, receptor type, f polypeptide (PTPRF), interacting protein (liprin), alpha 1 | AA195259 | 0.00343 |
| 210825_s_at | PEBP1 | phosphatidylethanolamine binding protein 1 | AF130103 | 0.00344 |
| 200039_s_at | PSMB2 | proteasome (prosome, macropain) subunit, beta type, 2 | NM_002794 | 0.00345 |
| 200971_s_at | SERP1 | stress-associated endoplasmic reticulum protein 1 | NM_014445 | 0.00347 |
| 212644_s_at | C14orf32 | chromosome 14 open reading frame 32 | AI671747 | 0.00351 |
| 201596_x_at | KRT18 | keratin 18 | NM_000224 | 0.00356 |
| 200048_s_at | JTB | jumping translocation breakpoint | NM_006694 | 0.00357 |
| 204341_at | TRIM16 | tripartite motif-containing 16 | NM_006470 | 0.00362 |
| 204341_at | TRIM16L | tripartite motif-containing 16-like | NM_006470 | 0.00362 |
| 221563_at | DUSP10 | dual specificity phosphatase 10 | N36770 | 0.00381 |
| 203234_at | UPP1 | uridine phosphorylase 1 | NM_003364 | 0.00389 |
| 207507_s_at | ATP5G3 | ATP synthase, H+ transporting, mitochondrial F0 complex, subunit C3 (subunit 9) | NM_001689 | 0.00410 |
| 204326_x_at | MT1X | metallothionein 1X | NM_002450 | 0.00426 |
| 208821_at | SNRPB | small nuclear ribonucleoprotein polypeptides B and B1 | J04564 | 0.00440 |
| 218026_at | CCDC56 | coiled-coil domain containing 56 | NM_014019 | 0.00459 |
| 202644_s_at | TNFAIP3 | tumor necrosis factor, alpha-induced protein 3 | NM_006290 | 0.00461 |
| 201631_s_at | IER3 | immediate early response 3 | NM_003897 | 0.00469 |
| 218566_s_at | CHORDC1 | cysteine and histidine-rich domain (CHORD)-containing 1 | NM_012124 | 0.00476 |
| 222162_s_at | ADAMTS1 | ADAM metallopeptidase with thrombospondin type 1 motif, 1 | AK023795 | 0.00483 |
| 218737_at | SBNO1 | strawberry notch homolog 1 (Drosophila) | NM_018183 | 0.00558 |
| 208812_x_at | HLA-C | major histocompatibility complex, class I, C | BC004489 | 0.00571 |
| 200014_s_at | HNRNPC | heterogeneous nuclear ribonucleoprotein C (C1/C2) | NM_004500 | 0.00577 |
| 207332_s_at | TFRC | transferrin receptor (p90, CD71) | NM_003234 | 0.00577 |
| 205449_at | SAC3D1 | SAC3 domain containing 1 | NM_013299 | 0.00644 |
| 210434_x_at | JTB | jumping translocation breakpoint | AF151056 | 0.00645 |
| 213133_s_at | GCSH | glycine cleavage system protein H (aminomethyl carrier) | AW237404 | 0.00656 |
| 220091_at | SLC2A6 | solute carrier family 2 (facilitated glucose transporter), member 6 | NM_017585 | 0.00673 |
| 203343_at | UGDH | UDP-glucose dehydrogenase | NM_003359 | 0.00693 |
| 205292_s_at | HNRNPA2B1 | heterogeneous nuclear ribonucleoprotein A2/B1 | NM_002137 | 0.00721 |
| 202252_at | RAB13 | RAB13, member RAS oncogene family | NM_002870 | 0.00797 |
| 214866_at | PLAUR | plasminogen activator, urokinase receptor | X74039 | 0.00802 |
| 210758_at | PSIP1 | PC4 and SFRS1 interacting protein 1 | AF098482 | 0.00810 |
| 222062_at | IL27RA | interleukin 27 receptor, alpha | AI983115 | 0.00816 |
| 201243_s_at | ATP1B1 | ATPase, Na+/K+ transporting, beta 1 polypeptide | NM_001677 | 0.00818 |

FIG. 17C

| Affy ID | Gene Symbol | Title | Public ID | p |
|---|---|---|---|---|
| 205128_x_at | PTGS1 | prostaglandin-endoperoxide synthase 1 (prostaglandin G/H synthase and cyclooxygenase) | NM_000962 | 0.00822 |
| 201231_s_at | ENO1 | enolase 1, (alpha) | NM_001428 | 0.00843 |
| 204616_at | UCHL3 | ubiquitin carboxyl-terminal esterase L3 (ubiquitin thiolesterase) | NM_006002 | 0.00849 |
| 200024_at | RPS5 | ribosomal protein S5 | NM_001009 | 0.00907 |
| 217753_s_at | RPS26 | ribosomal protein S26 | NM_001029 | 0.00972 |
| 201152_s_at | MBNL1 | muscleblind-like (Drosophila) | N31913 | 0.00976 |
| 36711_at | MAFF | v-maf musculoaponeurotic fibrosarcoma oncogene homolog F (avian) | AL021977 | 0.01018 |
| 211558_s_at | DHPS | deoxyhypusine synthase | U26266 | 0.01058 |
| 204279_at | PSMB9 | proteasome (prosome, macropain) subunit, beta type, 9 (large multifunctional peptidase 2) | NM_002800 | 0.01073 |
| 219697_at | HS3ST2 | heparan sulfate (glucosamine) 3-O-sulfotransferase 2 | NM_006043 | 0.01150 |
| 202120_x_at | AP2S1 | adaptor-related protein complex 2, sigma 1 subunit | NM_004069 | 0.01161 |
| 208784_s_at | KLHDC3 | kelch domain containing 3 | BC001793 | 0.01167 |
| 207180_s_at | HTATIP2 | HIV-1 Tat interactive protein 2, 30kDa | NM_006410 | 0.01188 |
| 213554_s_at | CDV3 | CDV3 homolog (mouse) | AI928407 | 0.01194 |
| 204422_s_at | FGF2 | fibroblast growth factor 2 (basic) | NM_002006 | 0.01194 |
| 215313_x_at | HLA-A | major histocompatibility complex, class I, A | AA573862 | 0.01204 |
| 202014_at | PPP1R15A | protein phosphatase 1, regulatory (inhibitor) subunit 15A | NM_014330 | 0.01235 |
| 208607_s_at | SAA2 | serum amyloid A2 | NM_030754 | 0.01253 |
| 208607_s_at | SAA1 | serum amyloid A1 | NM_030754 | 0.01253 |
| 210538_s_at | BIRC3 | baculoviral IAP repeat containing 3 | U37546 | 0.01258 |
| 212296_at | PSMD14 | proteasome (prosome, macropain) 26S subunit, non-ATPase, 14 | NM_005805 | 0.01281 |
| 202859_x_at | IL8 | interleukin 8 | NM_000584 | 0.01283 |
| 211714_x_at | TUBB | tubulin, beta | BC005838 | 0.01295 |
| 201266_at | TXNRD1 | thioredoxin reductase 1 | NM_003330 | 0.01310 |
| 201483_s_at | SUPT4H1 | suppressor of Ty 4 homolog 1 (S. cerevisiae) | BC002802 | 0.01319 |

FIG. 18A

Table L: Composite "Skin Tone" Benchmark Signature; approximately 40 up-regulated + 58 down-regulated

| Affy ID | Gene Symbol | Title | Public ID | AvgSignal Control | AvgSignalTreated | AvgFC |
|---|---|---|---|---|---|---|
| 201160_s_at | CSDA | cold shock domain protein A | AL556190 | 15588 | 16710 | 1.1 |
| 201216_at | ERP29 | endoplasmic reticulum protein 29 | NM_006817 | 5837 | 6813 | 1.1 |
| 201694_s_at | EGR1 | early growth response 1 | NM_001964 | 5136 | 7069 | 1.37 |
| 201749_at | ECE1 | Endothelin converting enzyme 1 | BF969352 | 286 | 386 | 1.34 |
| 202730_s_at | PDCD4 | programmed cell death 4 (neoplastic transformation inhibitor) | NM_014456 | 2054 | 2352 | 1.18 |
| 203304_at | BAMBI | BMP and activin membrane-bound inhibitor homolog (Xenopus laevis) | NM_012342 | 338 | 499 | 1.49 |
| 203597_s_at | WBP4 | WW domain binding protein 4 (formin binding protein 21) | AI734228 | 888 | 1098 | 1.19 |
| 203831_at | R3HDM2 | R3H domain containing 2 | NM_014925 | 999 | 1206 | 1.23 |
| 204352_at | TRAF5 | TNF receptor-associated factor 5 | NM_004619 | 182 | 201 | 1.33 |
| 205205_at | RELB | v-rel reticuloendotheliosis viral oncogene homolog B, nuclear factor of kappa light polypeptide gene enhancer in B-cells 3 (avian) | NM_006509 | 307 | 435 | 1.34 |
| 207624_s_at | RPGR | retinitis pigmentosa GTPase regulator | NM_000328 | 271 | 312 | 1.27 |
| 209885_at | RHOD | ras homolog gene family, member D | BC001338 | 3659 | 4531 | 1.22 |
| 210886_x_at | TP53AP1 | TP53 activated protein 1 | AB007457 | 977 | 1167 | 1.14 |
| 211123_at | SLC5A5 | solute carrier family 5 (sodium iodide symporter), member 5 | D87920 | 292 | 402 | 1.26 |
| 211950_at | UBR4 | ubiquitin protein ligase E3 component n-recognin 4 | AB007931 | 1421 | 1785 | 1.35 |
| 212044_s_at | RPL27A | Ribosomal protein L27a | BE737027 | 1275 | 1692 | 1.25 |
| 213281_at | JUN | Jun oncogene | BE327172 | 791 | 1011 | 1.29 |
| 213560_at | GADD45B | Growth arrest and DNA-damage-inducible, beta | AV658684 | 291 | 375 | 1.3 |
| 213932_x_at | HLA-A | major histocompatibility complex, class I, A | AI923492 | 10893 | 13553 | 1.13 |
| 213936_x_at | SFTPB | surfactant, pulmonary-associated protein B | AW276646 | 323 | 390 | 1.3 |

FIG. 18B

| | | | | | | |
|---|---|---|---|---|---|---|
| 214317_x_at | RPS9 | ribosomal protein S9 | BE348997 | 23563 | 29560 | 1.22 |
| 214395_x_at | | CDNA clone IMAGE:4838699 | AI335509 | 484 | 646 | 1.28 |
| 215016_x_at | DST | dystonin | BC004912 | 2500 | 2590 | 1.09 |
| 215450_at | | | W87901 | 5859 | 7132 | 1.16 |
| 216609_at | TXN | Thioredoxin | AF065241 | 3354 | 4269 | 1.2 |
| 217903_at | STRN4 | striatin, calmodulin binding protein 4 | NM_013403 | 330 | 430 | 1.31 |
| 218151_x_at | GPR172A | G protein-coupled receptor 172A | NM_024531 | 2345 | 2765 | 1.16 |
| 218388_at | PGLS | 6-phosphogluconolactonase | NM_012088 | 2785 | 3513 | 1.14 |
| 218420_s_at | C13orf23 | chromosome 13 open reading frame 23 | NM_025138 | 508 | 567 | 1.2 |
| 218435_at | DNAJC15 | DnaJ (Hsp40) homolog, subfamily C, member 15 | NM_013238 | 127 | 242 | 2.28 |
| 218931_at | RAB17 | RAB17, member RAS oncogene family | NM_022449 | 578 | 678 | 1.12 |
| 219254_at | FLJ22222 | hypothetical protein FLJ22222 | NM_024648 | 248 | 341 | 1.21 |
| 219916_s_at | RNF39 | ring finger protein 39 | NM_025236 | 363 | 489 | 1.29 |
| 220219_s_at | LRRC37A | leucine rich repeat containing 37A | NM_018001 | 166 | 209 | 1.53 |
| 220219_s_at | LRRC37A2 | leucine rich repeat containing 37, member A2 | NM_018001 | 166 | 209 | 1.53 |
| 220219_s_at | LRRC37A3 | leucine rich repeat containing 37, member A3 | NM_018001 | 166 | 209 | 1.53 |
| 220387_s_at | HHLA3 | HERV-H LTR-associating 3 | NM_007071 | 410 | 484 | 1.13 |
| 221269_s_at | SH3BGRL3 | SH3 domain binding glutamic acid-rich protein like 3 | NM_031286 | 9634 | 11906 | 1.16 |
| 221865_at | C9orf91 | chromosome 9 open reading frame 91 | BF969986 | 432 | 528 | 1.3 |
| 221943_x_at | RPL38 | Ribosomal protein L38 | AW303136 | 4435 | 5176 | 1.13 |
| 222094_at | SULT1A3 | sulfotransferase family, cytosolic, 1A, phenol-preferring, member 3 | AI580112 | 186 | 286 | 1.6 |
| 222094_at | SULT1A4 | sulfotransferase family, cytosolic, 1A, phenol-preferring, member 4 | AI580112 | 186 | 286 | 1.6 |
| 36553_at | ASMTL | acetylserotonin O-methyltransferase-like | AA669799 | 750 | 863 | 1.16 |
| | | 58 down-regulated below. | | | | |

FIG. 18C

| Affy ID | Gene Symbol | Title | Public ID | AvgSignalControl | AvgSignalTreated | AvgFC |
|---|---|---|---|---|---|---|
| 201017_at | EIF1AX | eukaryotic translation initiation factor 1A, X-linked | BG149698 | 2960 | 2165 | 1.3 |
| 201437_s_at | EIF4E | eukaryotic translation initiation factor 4E | NM_001968 | 5628 | 4499 | 1.09 |
| 201534_s_at | UBL3 | ubiquitin-like 3 | AF044221 | 921 | 703 | 1.34 |
| 201634_s_at | CYB5B | cytochrome b5 type B (outer mitochondrial membrane) | NM_030579 | 6244 | 5584 | 1.09 |
| 201652_at | COPS5 | COP9 constitutive photomorphogenic homolog subunit 5 (Arabidopsis) | NM_006837 | 7929 | 7453 | 1.05 |
| 201669_s_at | MARCKS | myristoylated alanine-rich protein kinase C substrate | NM_002356 | 4402 | 3864 | 1.1 |
| 201678_s_at | C3orf37 | chromosome 3 open reading frame 37 | NM_020187 | 2061 | 1776 | 1.17 |
| 202524_s_at | SPOCK2 | sparc/osteonectin, cwcv and kazal-like domains proteoglycan (testican) 2 | NM_014767 | 232 | 205 | 1.26 |
| 203008_x_at | TXNDC9 | thioredoxin domain containing 9 | NM_005783 | 12747 | 11685 | 1.1 |
| 203635_at | DSCR3 | Down syndrome critical region gene 3 | NM_006052 | 878 | 748 | 1.22 |
| 203812_at | | CDNA clone IMAGE:5922621 | AB011538 | 209 | 137 | 1.74 |
| 204700_x_at | C1orf107 | chromosome 1 open reading frame 107 | NM_014388 | 1665 | 1455 | 1.13 |
| 204804_at | TRIM21 | tripartite motif-containing 21 | NM_003141 | 1107 | 939 | 1.23 |
| 204825_at | MELK | maternal embryonic leucine zipper kinase | NM_014791 | 8469 | 8178 | 1.05 |
| 205115_s_at | RBM19 | RNA binding motif protein 19 | NM_016196 | 407 | 371 | 1.12 |
| 206533_at | CHRNA5 | cholinergic receptor, nicotinic, alpha 5 | NM_000745 | 725 | 654 | 1.19 |
| 208112_x_at | EHD1 | EH-domain containing 1 | NM_006795 | 1306 | 1146 | 1.27 |
| 208873_s_at | REEP5 | receptor accessory protein 5 | BC000232 | 4454 | 3790 | 1.17 |
| 210218_s_at | SP100 | SP100 nuclear antigen | U36501 | 507 | 408 | 1.25 |
| 210242_x_at | ST20 | suppressor of tumorigenicity 20 | AF249277 | 1019 | 995 | 1.15 |
| 210933_s_at | FSCN1 | fascin homolog 1, actin-bundling protein (Strongylocentrotus purpuratus) | BC004908 | 3865 | 2769 | 1.21 |

FIG. 18D

| | | | | | | |
|---|---|---|---|---|---|---|
| 211078_s_at | STK3 | serine/threonine kinase 3 (STE20 homolog, yeast) | Z25422 | 580 | 393 | 1.29 |
| 212092_at | PEG10 | paternally expressed 10 | BE858180 | 817 | 611 | 1.35 |
| 212432_at | GRPEL1 | GrpE-like 1, mitochondrial (E. coli) | AL542571 | 5747 | 5223 | 1.1 |
| 212485_at | GPATCH8 | G patch domain containing 8 | AU146596 | 1243 | 1053 | 1.18 |
| 212490_at | DNAJC8 | DnaJ (Hsp40) homolog, subfamily C, member 8 | AA843895 | 549 | 452 | 1.22 |
| 212599_at | AUTS2 | autism susceptibility candidate 2 | AK025298 | 223 | 205 | 1.15 |
| 212751_at | UBE2N | ubiquitin-conjugating enzyme E2N (UBC13 homolog, yeast) | BG290646 | 3625 | 3133 | 1.18 |
| 212836_at | POLD3 | polymerase (DNA-directed), delta 3, accessory subunit | D26018 | 1696 | 1409 | 1.23 |
| 216545_at | LOC645538 | similar to Aspartate aminotransferase, mitochondrial precursor (Transaminase A) (Glutamate oxaloacetate transaminase 2) | AL049710 | 228 | 178 | 1.51 |
| 216993_s_at | COL11A2 | collagen, type XI, alpha 2 | U32169 | 340 | 285 | 1.24 |
| 217717_s_at | YWHAB | tyrosine 3-monooxygenase/tryptophan 5-monooxygenase activation protein, beta polypeptide | BF246499 | 15355 | 14219 | 1.12 |
| 217724_at | SERBP1 | SERPINE1 mRNA binding protein 1 | AF131807 | 17928 | 15265 | 1.22 |
| 217808_s_at | MAPKAP1 | mitogen-activated protein kinase associated protein 1 | NM_024117 | 2575 | 2180 | 1.32 |
| 217853_at | TNS3 | tensin 3 | NM_022748 | 815 | 670 | 1.24 |
| 217864_s_at | PIAS1 | protein inhibitor of activated STAT, 1 | NM_016166 | 1093 | 932 | 1.14 |
| 217981_s_at | FXC1 | fracture callus 1 homolog (rat) | NM_012192 | 1532 | 1240 | 1.17 |
| 218187_s_at | C8orf33 | chromosome 8 open reading frame 33 | NM_023080 | 1408 | 1175 | 1.19 |
| 218294_s_at | NUP50 | nucleoporin 50kDa | AF267865 | 2921 | 2128 | 1.22 |
| 218309_at | CAMK2N1 | calcium/calmodulin-dependent protein kinase II inhibitor 1 | NM_018584 | 3953 | 3755 | 1.1 |
| 218480_at | AGBL5 | ATP/GTP binding protein-like 5 | NM_021831 | 428 | 346 | 1.29 |
| 218488_at | EIF2B3 | eukaryotic translation initiation factor 2B, subunit 3 gamma, 58kDa | NM_020365 | 2633 | 2481 | 1.1 |
| 218514_at | C17orf71 | chromosome 17 open | NM_018149 | 2192 | 1739 | 1.37 |

FIG. 18E

| | | | | | | |
|---|---|---|---|---|---|---|
| | | reading frame 71 | | | | |
| 218650_at | DGCR8 | DiGeorge syndrome critical region gene 8 | NM_022775 | 573 | 487 | 1.28 |
| 218926_at | MYNN | myoneurin | NM_018657 | 1199 | 998 | 1.18 |
| 218929_at | CDKN2AIP | CDKN2A interacting protein | NM_017632 | 1636 | 1271 | 1.2 |
| 219008_at | C2orf43 | chromosome 2 open reading frame 43 | NM_021925 | 900 | 785 | 1.19 |
| 219207_at | EDC3 | enhancer of mRNA decapping 3 homolog (S. cerevisiae) | NM_025083 | 534 | 513 | 1.1 |
| 219522_at | FJX1 | four jointed box 1 (Drosophila) | NM_014344 | 3894 | 3252 | 1.17 |
| 219539_at | GEMIN6 | gem (nuclear organelle) associated protein 6 | NM_024775 | 3831 | 3555 | 1.19 |
| 220038_at | SGK3 | serum/glucocorticoid regulated kinase family, member 3 | NM_013257 | 779 | 628 | 1.19 |
| 221502_at | KPNA3 | karyopherin alpha 3 (importin alpha 4) | AL120704 | 5124 | 4241 | 1.23 |
| 221514_at | UTP14A | UTP14, U3 small nucleolar ribonucleoprotein, homolog A (yeast) | BC001149 | 1776 | 1527 | 1.12 |
| 221549_at | GRWD1 | glutamate-rich WD repeat containing 1 | AF337808 | 1385 | 1152 | 1.17 |
| 221650_s_at | MED18 | mediator complex subunit 18 | BC002694 | 880 | 744 | 1.34 |
| 221823_at | C5orf30 | chromosome 5 open reading frame 30 | AL565741 | 766 | 640 | 1.25 |
| 222105_s_at | NKIRAS2 | NFKB inhibitor interacting Ras-like 2 | AA452565 | 594 | 546 | 1.18 |
| 44702_at | SYDE1 | synapse defective 1, Rho GTPase, homolog 1 (C. elegans) | R77097 | 1066 | 919 | 1.1 |

FIG. 19A

Table M: RA benchmark signature in tKC cell – 200 upregulated

| Rank | Probe set ID | Acronym | NetAffx Title | Log 2 Fold Change tRA to DMSO |
|---|---|---|---|---|
| 1 | 201661_s_at | ACSL3 | acyl-CoA synthetase long-chain family member 3 | 0.8195 |
| 2 | 203504_s_at | ABCA1 | ATP-binding cassette, sub-family A (ABC1), member 1 | 0.9653 |
| 3 | 221009_s_at | ANGPTL4 | angiopoietin-like 4 | 2.2685 |
| 4 | 38037_at | HBEGF | heparin-binding EGF-like growth factor | 1.7187 |
| 5 | 205067_at | IL1B | interleukin 1, beta | 1.798 |
| 6 | 202481_at | DHRS3 | dehydrogenase/reductase (SDR family) member 3 | 5.5512 |
| 7 | 200666_s_at | DNAJB1 | DnaJ (Hsp40) homolog, subfamily B, member 1 | 0.5046 |
| 8 | 219634_at | CHST11 | carbohydrate (chondroitin 4) sulfotransferase 11 | 0.8533 |
| 9 | 205220_at | GPR109B | niacin receptor 2 | 2.9468 |
| 10 | 203234_at | UPP1 | uridine phosphorylase 1 | 0.9404 |
| 11 | 39402_at | IL1B | interleukin 1, beta | 1.6479 |
| 12 | 202936_s_at | SOX9 | SRY (sex determining region Y)-box 9 | 0.4558 |
| 13 | 201417_at | SOX4 | SRY (sex determining region Y)-box 4 | 0.734 |
| 14 | 209278_s_at | TFPI2 | tissue factor pathway inhibitor 2 | 0.6745 |
| 15 | 210001_s_at | SOCS1 | suppressor of cytokine signaling 1 | 0.7299 |
| 16 | 201609_x_at | ICMT | isoprenylcysteine carboxyl methyltransferase | 0.3434 |
| 17 | 206074_s_at | HMGA1 | high mobility group AT-hook 1 | 0.4707 |
| 18 | 202998_s_at | LOXL2 | lysyl oxidase-like 2 | 1.968 |
| 19 | 202795_x_at | TRIOBP | TRIO and F-actin binding protein | 0.5995 |
| 20 | 202393_s_at | KLF10 | Kruppel-like factor 10 | 0.7119 |
| 21 | 204908_s_at | BCL3 | B-cell CLL/lymphoma 3 | 1.5751 |
| 22 | 39248_at | AQP3 | aquaporin 3 (Gill blood group) | 1.6837 |
| 23 | 203373_at | SOCS2 | suppressor of cytokine signaling 2 | 0.3762 |
| 24 | 201660_at | ACSL3 | Acyl-CoA synthetase long-chain family member 3 | 0.7564 |
| 25 | 210762_s_at | DLC1 | deleted in liver cancer 1 | 0.7581 |
| 26 | 200664_s_at | DNAJB1 | DnaJ (Hsp40) homolog, subfamily B, member 1 | 0.6956 |
| 27 | 218627_at | DRAM1 | DNA-damage regulated autophagy modulator 1 | 0.6939 |
| 28 | 209744_x_at | ITCH | itchy E3 ubiquitin protein ligase homolog (mouse) | 0.3175 |
| 29 | 201242_s_at | ATP1B1 | ATPase, Na+/K+ transporting, beta 1 polypeptide | 0.3709 |
| 30 | 202052_s_at | RAI14 | retinoic acid induced 14 | 0.7514 |
| 31 | 206432_at | HAS2 | hyaluronan synthase 2 | 2.4838 |
| 32 | 212099_at | RHOB | ras homolog gene family, member B | 0.97 |
| 33 | 202207_at | ARL4C | ADP-ribosylation factor-like 4C | 0.7433 |
| 34 | 208394_x_at | ESM1 | endothelial cell-specific molecule 1 | 2.3689 |
| 35 | 218980_at | FHOD3 | formin homology 2 domain containing 3 | 1.6996 |
| 36 | 209277_at | TFPI2 | tissue factor pathway inhibitor 2 | 0.691 |
| 37 | 208937_s_at | ID1 | inhibitor of DNA binding 1, dominant negative helix-loop-helix protein | 0.8465 |
| 38 | 206632_s_at | APOBEC3B | apolipoprotein B mRNA editing enzyme, catalytic polypeptide-like 3B | 1.6078 |

FIG. 19B

| A | B | C | D | E |
|---|---|---|---|---|
| 39 | 210095_s_at | IGFBP3 | insulin-like growth factor binding protein 3 | 3.7739 |
| 40 | 202599_s_at | NRIP1 | nuclear receptor interacting protein 1 | 1.0795 |
| 41 | 212444_at | null | null | 0.8478 |
| 42 | 208960_s_at | KLF6 | Kruppel-like factor 6 | 0.5209 |
| 43 | 202638_s_at | ICAM1 | intercellular adhesion molecule 1 | 0.8976 |
| 44 | 203505_at | ABCA1 | ATP-binding cassette, sub-family A (ABC1), member 1 | 1.378 |
| 45 | 208963_x_at | FADS1 | fatty acid desaturase 1 | 0.4765 |
| 46 | 212268_at | SERPINB1 | serpin peptidase inhibitor, clade B (ovalbumin), member 1 | 0.4586 |
| 47 | 204541_at | SEC14L2 | SEC14-like 2 (S. cerevisiae) | 1.4385 |
| 48 | 217739_s_at | NAMPT | nicotinamide phosphoribosyltransferase | 0.3674 |
| 49 | 218376_s_at | MICAL1 | microtubule associated monoxygenase, calponin and LIM domain containing 1 | 0.4038 |
| 50 | 211668_s_at | PLAU | plasminogen activator, urokinase | 0.8499 |
| 51 | 217997_at | PHLDA1 | pleckstrin homology-like domain, family A, member 1 | 0.4622 |
| 52 | 204264_at | CPT2 | carnitine palmitoyltransferase 2 | 0.4167 |
| 53 | 217992_s_at | EFHD2 | EF-hand domain family, member D2 | 1.0462 |
| 54 | 218309_at | CAMK2N1 | calcium/calmodulin-dependent protein kinase II inhibitor 1 | 0.4016 |
| 55 | 209955_s_at | FAP | fibroblast activation protein, alpha | 0.8682 |
| 56 | 202384_s_at | TCOF1 | Treacher Collins-Franceschetti syndrome 1 | 0.5772 |
| 57 | 214783_s_at | ANXA11 | annexin A11 | 0.4334 |
| 58 | 219239_s_at | ZNF654 | zinc finger protein 654 | 0.2745 |
| 59 | 211361_s_at | SERPINB13 | serpin peptidase inhibitor, clade B (ovalbumin), member 13 | 1.1086 |
| 60 | 218181_s_at | MAP4K4 | mitogen-activated protein kinase kinase kinase kinase 4 | 0.5099 |
| 61 | 203658_at | SLC25A20 | solute carrier family 25 (carnitine/acylcarnitine translocase), member 20 | 0.4415 |
| 62 | 202637_s_at | ICAM1 | intercellular adhesion molecule 1 | 0.9545 |
| 63 | 212143_s_at | IGFBP3 | insulin-like growth factor binding protein 3 | 5.4511 |
| 64 | 211538_s_at | HSPA2 | heat shock 70kDa protein 2 | 0.5254 |
| 65 | 201889_at | FAM3C | family with sequence similarity 3, member C | 0.4021 |
| 66 | 205479_s_at | PLAU | plasminogen activator, urokinase | 0.6382 |
| 67 | 201830_s_at | NET1 | neuroepithelial cell transforming 1 | 0.4115 |
| 68 | 208961_s_at | KLF6 | Kruppel-like factor 6 | 0.4575 |
| 69 | 201860_s_at | PLAT | plasminogen activator, tissue | 0.4962 |
| 70 | 207196_s_at | TNIP1 | TNFAIP3 interacting protein 1 | 0.4522 |
| 71 | 200880_at | DNAJA1 | DnaJ (Hsp40) homolog, subfamily A, member 1 | 0.2984 |
| 72 | 205780_at | BIK | BCL2-interacting killer (apoptosis-inducing) | 1.1541 |
| 73 | 203180_at | ALDH1A3 | aldehyde dehydrogenase 1 family, member A3 | 1.5097 |
| 74 | 202208_s_at | ARL4C | ADP-ribosylation factor-like 4C | 0.6776 |
| 75 | 219257_s_at | SPHK1 | sphingosine kinase 1 | 0.6771 |
| 76 | 218888_s_at | NETO2 | neuropilin (NRP) and tolloid (TLL)-like 2 | 0.2811 |
| 77 | 218205_s_at | MKNK2 | MAP kinase interacting serine/threonine kinase 2 | 0.4336 |
| 78 | 203821_at | HBEGF | heparin-binding EGF-like growth factor | 1.5091 |
| 79 | 216899_s_at | SKAP2 | src kinase associated phosphoprotein 2 | 0.5631 |
| 80 | 203936_s_at | MMP9 | matrix metallopeptidase 9 (gelatinase B, 92kDa gelatinase, | 0.7523 |

FIG. 19C

| A | B | C | D | E |
|---|---|---|---|---|
|  |  |  | 92kDa type IV collagenase) |  |
| 81 | 215001_s_at | GLUL | glutamate-ammonia ligase (glutamine synthetase) | 0.3824 |
| 82 | 213603_s_at | RAC2 | ras-related C3 botulinum toxin substrate 2 (rho family, small GTP binding protein Rac2) | 0.4568 |
| 83 | 202600_s_at | NRIP1 | nuclear receptor interacting protein 1 | 1.2916 |
| 84 | 202786_at | STK39 | serine threonine kinase 39 (STE20/SPS1 homolog, yeast) | 0.528 |
| 85 | 206200_s_at | ANXA11 | annexin A11 | 0.3154 |
| 86 | 218284_at | SMAD3 | SMAD family member 3 | 0.4483 |
| 87 | 208083_s_at | ITGB6 | integrin, beta 6 | 0.997 |
| 88 | 201041_s_at | DUSP1 | dual specificity phosphatase 1 | 0.8132 |
| 89 | 221884_at | MECOM | MDS1 and EVI1 complex locus | 0.69 |
| 90 | 203372_s_at | SOCS2 | suppressor of cytokine signaling 2 | 0.4148 |
| 91 | 213288_at | MBOAT2 | membrane bound O-acyltransferase domain containing 2 | 0.5254 |
| 92 | 201170_s_at | BHLHE40 | basic helix-loop-helix family, member e40 | 0.3954 |
| 93 | 216945_x_at | PASK | PAS domain containing serine/threonine kinase | 0.3592 |
| 94 | 202037_s_at | SFRP1 | secreted frizzled-related protein 1 | 0.3867 |
| 95 | 210817_s_at | CALCOCO2 | calcium binding and coiled-coil domain 2 | 0.3057 |
| 96 | 209108_at | TSPAN6 | tetraspanin 6 | 0.4523 |
| 97 | 220465_at | LOC80054 | hypothetical LOC80054 | 0.3631 |
| 98 | 208613_s_at | FLNB | filamin B, beta | 0.7171 |
| 99 | 211113_s_at | ABCG1 | ATP-binding cassette, sub-family G (WHITE), member 1 | 1.2379 |
| 100 | 210786_s_at | FLI1 | Friend leukemia virus integration 1 | 0.4757 |
| 101 | 204675_at | SRD5A1 | steroid-5-alpha-reductase, alpha polypeptide 1 (3-oxo-5 alpha-steroid delta 4-dehydrogenase alpha 1) | 0.3057 |
| 102 | 212026_s_at | EXOC7 | exocyst complex component 7 | 0.3415 |
| 103 | 213017_at | ABHD3 | abhydrolase domain containing 3 | 0.4608 |
| 104 | 219850_s_at | EHF | ets homologous factor | 1.0191 |
| 105 | 204105_s_at | NRCAM | neuronal cell adhesion molecule | 0.5845 |
| 106 | 221832_s_at | LUZP1 | leucine zipper protein 1 | 0.3487 |
| 107 | 219205_at | SRR | serine racemase | 0.3779 |
| 108 | 221509_at | DENR | density-regulated protein | 0.4454 |
| 109 | 203072_at | MYO1E | myosin IE | 0.4071 |
| 110 | 208084_at | ITGB6 | integrin, beta 6 | 0.9548 |
| 111 | 200800_s_at | HSPA1A | heat shock 70kDa protein 1A | 0.3251 |
| 112 | 217966_s_at | FAM129A | family with sequence similarity 129, member A | 0.4306 |
| 113 | 203108_at | GPRC5A | G protein-coupled receptor, family C, group 5, member A | 1.2073 |
| 114 | 37152_at | PPARD | peroxisome proliferator-activated receptor delta | 0.341 |
| 115 | 213361_at | TDRD7 | tudor domain containing 7 | 0.4056 |
| 116 | 202071_at | SDC4 | syndecan 4 | 0.3373 |
| 117 | 203062_s_at | MDC1 | mediator of DNA-damage checkpoint 1 | 0.2939 |
| 118 | 205122_at | TMEFF1 | transmembrane protein with EGF-like and two follistatin-like domains 1 | 0.6406 |
| 119 | 201669_s_at | MARCKS | myristoylated alanine-rich protein kinase C substrate | 0.4037 |
| 120 | 217967_s_at | FAM129A | family with sequence similarity 129, member A | 0.3821 |

FIG. 19D

| A | B | C | D | E |
|---|---|---|---|---|
| 121 | 218000_s_at | PHLDA1 | pleckstrin homology-like domain, family A, member 1 | 0.8773 |
| 122 | 201930_at | MCM6 | minichromosome maintenance complex component 6 | 0.2796 |
| 123 | 201834_at | PRKAB1 | protein kinase, AMP-activated, beta 1 non-catalytic subunit | 0.2963 |
| 124 | 202295_s_at | CTSH | cathepsin H | 0.6305 |
| 125 | 217996_at | PHLDA1 | pleckstrin homology-like domain, family A, member 1 | 0.4136 |
| 126 | 204639_at | ADA | adenosine deaminase | 0.7075 |
| 127 | 210276_s_at | TRIOBP | nucleolar protein 12 | 0.5498 |
| 128 | 216237_s_at | MCM5 | minichromosome maintenance complex component 5 | 0.4018 |
| 129 | 201466_s_at | JUN | jun oncogene | 0.4221 |
| 130 | 218136_s_at | SLC25A37 | solute carrier family 25, member 37 | 0.5147 |
| 131 | 213680_at | KRT6B | keratin 6B | 1.0629 |
| 132 | 202949_s_at | FHL2 | four and a half LIM domains 2 | 0.2984 |
| 133 | 209118_s_at | TUBA1A | tubulin, alpha 1a | 0.3153 |
| 134 | 212186_at | ACACA | acetyl-Coenzyme A carboxylase alpha | 0.4167 |
| 135 | 201147_s_at | TIMP3 | TIMP metallopeptidase inhibitor 3 | 0.7617 |
| 136 | 204361_s_at | SKAP2 | src kinase associated phosphoprotein 2 | 0.4332 |
| 137 | 218501_at | ARHGEF3 | Rho guanine nucleotide exchange factor (GEF) 3 | 0.2991 |
| 138 | 202859_x_at | IL8 | interleukin 8 | 1.4416 |
| 139 | 208862_s_at | CTNND1 | catenin (cadherin-associated protein), delta 1 | 0.2935 |
| 140 | 206971_at | GPR161 | G protein-coupled receptor 161 | 0.7233 |
| 141 | 211464_x_at | CASP6 | caspase 6, apoptosis-related cysteine peptidase | 0.4032 |
| 142 | 201662_s_at | ACSL3 | acyl-CoA synthetase long-chain family member 3 | 0.6678 |
| 143 | 202107_s_at | MCM2 | minichromosome maintenance complex component 2 | 0.2881 |
| 144 | 205032_at | ITGA2 | integrin, alpha 2 (CD49B, alpha 2 subunit of VLA-2 receptor) | 0.416 |
| 145 | 210229_s_at | CSF2 | colony stimulating factor 2 (granulocyte-macrophage) | 0.7148 |
| 146 | 218613_at | PSD3 | pleckstrin and Sec7 domain containing 3 | 0.5426 |
| 147 | 201416_at | SOX4 | SRY (sex determining region Y)-box 4 | 0.9743 |
| 148 | 217875_s_at | PMEPA1 | prostate transmembrane protein, androgen induced 1 | 0.5132 |
| 149 | 213916_at | ZNF20 | zinc finger protein 20 | 0.3369 |
| 150 | 219631_at | LRP12 | low density lipoprotein-related protein 12 | 0.3345 |
| 151 | 217272_s_at | SERPINB13 | serpin peptidase inhibitor, clade B (ovalbumin), member 13 | 0.6539 |
| 152 | 204567_s_at | ABCG1 | ATP-binding cassette, sub-family G (WHITE), member 1 | 1.6989 |
| 153 | 218273_s_at | PDP1 | pyruvate dehydrogenase phosphatase catalytic subunit 1 | 0.3194 |
| 154 | 204420_at | FOSL1 | FOS-like antigen 1 | 0.4833 |
| 155 | 218404_at | SNX10 | sorting nexin 10 | 0.3684 |
| 156 | 210517_s_at | AKAP12 | A kinase (PRKA) anchor protein 12 | 0.5333 |
| 157 | 213372_at | PAQR3 | progestin and adipoQ receptor family member III | 0.2703 |
| 158 | 204422_s_at | FGF2 | fibroblast growth factor 2 (basic) | 0.7506 |
| 159 | 207850_at | CXCL3 | chemokine (C-X-C motif) ligand 3 | 1.3552 |
| 160 | 210792_x_at | SIVA1 | SIVA1, apoptosis-inducing factor | 0.3258 |
| 161 | 202581_at | HSPA1A | heat shock 70kDa protein 1A | 0.3325 |
| 162 | 212298_at | NRP1 | neuropilin 1 | 0.5757 |

FIG. 19E

| A | B | C | D | E |
|---|---|---|---|---|
| 163 | 212276_at | LPIN1 | lipin 1 | 0.368 |
| 164 | 207408_at | SLC22A14 | solute carrier family 22, member 14 | 0.7755 |
| 165 | 202529_at | PRPSAP1 | phosphoribosyl pyrophosphate synthetase-associated protein 1 | 0.3304 |
| 166 | 206460_at | AJAP1 | adherens junctions associated protein 1 | 0.3916 |
| 167 | 215017_s_at | FNBP1L | formin binding protein 1-like | 0.4485 |
| 168 | 219058_x_at | TINAGL1 | tubulointerstitial nephritis antigen-like 1 | 1.2721 |
| 169 | 202584_at | NFX1 | nuclear transcription factor, X-box binding 1 | 0.4668 |
| 170 | 217999_s_at | PHLDA1 | pleckstrin homology-like domain, family A, member 1 | 0.7862 |
| 171 | 202392_s_at | PISD | chromosome 22 open reading frame 30 | 0.7372 |
| 172 | 203991_s_at | KDM6A | lysine (K)-specific demethylase 6A | 0.3162 |
| 173 | 203837_at | MAP3K5 | mitogen-activated protein kinase kinase kinase 5 | 0.2845 |
| 174 | 202627_s_at | SERPINE1 | serpin peptidase inhibitor, clade E (nexin, plasminogen activator inhibitor type 1), member 1 | 0.4701 |
| 175 | 205115_s_at | RBM19 | RNA binding motif protein 19 | 0.2881 |
| 176 | 202206_at | ARL4C | ADP-ribosylation factor-like 4C | 0.7468 |
| 177 | 206972_s_at | GPR161 | G protein-coupled receptor 161 | 0.6719 |
| 178 | 210118_s_at | IL1A | interleukin 1, alpha | 0.4596 |
| 179 | 205847_at | PRSS22 | protease, serine, 22 | 0.8473 |
| 180 | 213392_at | IQCK | IQ motif containing K | 0.3576 |
| 181 | 204200_s_at | PDGFB | platelet-derived growth factor beta polypeptide (simian sarcoma viral (v-sis) oncogene homolog) | 2.2826 |
| 182 | 212274_at | LPIN1 | lipin 1 | 0.465 |
| 183 | 220311_at | N6AMT1 | N-6 adenine-specific DNA methyltransferase 1 (putative) | 0.4651 |
| 184 | 219210_s_at | RAB8B | RAB8B, member RAS oncogene family | 0.4009 |
| 185 | 209508_x_at | CFLAR | CASP8 and FADD-like apoptosis regulator | 0.4364 |
| 186 | 213053_at | HAUS5 | HAUS augmin-like complex, subunit 5 | 0.6235 |
| 187 | 203855_at | WDR47 | WD repeat domain 47 | 0.3422 |
| 188 | 203736_s_at | PPFIBP1 | PTPRF interacting protein, binding protein 1 (liprin beta 1) | 0.4981 |
| 189 | 218743_at | CHMP6 | chromatin modifying protein 6 | 0.4669 |
| 190 | 214119_s_at | FKBP1A | FK506 binding protein 1A, 12kDa | 0.2669 |
| 191 | 213419_at | APBB2 | amyloid beta (A4) precursor protein-binding, family B, member 2 | 0.3081 |
| 192 | 209706_at | NKX3-1 | NK3 homeobox 1 | 0.2874 |
| 193 | 220227_at | CDH4 | cadherin 4, type 1, R-cadherin (retinal) | 0.551 |
| 194 | 208705_s_at | EIF5 | eukaryotic translation initiation factor 5 | 0.3245 |
| 195 | 208779_x_at | DDR1 | discoidin domain receptor tyrosine kinase 1 | 0.4142 |
| 196 | 213572_s_at | SERPINB1 | serpin peptidase inhibitor, clade B (ovalbumin), member 1 | 0.3387 |
| 197 | 212729_at | DLG3 | discs, large homolog 3 (Drosophila) | 0.2851 |
| 198 | 204475_at | MMP1 | matrix metallopeptidase 1 (interstitial collagenase) | 0.9297 |
| 199 | 37117_at | ARHGAP8 | Rho GTPase activating protein 8 | 0.4329 |
| 200 | 217202_s_at | GLUL | glutamate-ammonia ligase (glutamine synthetase) | 0.5098 |

FIG. 20A

Table N: RA benchmark signature in tKC, 200 down-regulated

| Rank | Probe set ID | Gene Symbol | NetAffx Title | Log 2 fold change tRA to DMSO |
|---|---|---|---|---|
| 1 | 204455_at | DST | dystonin | -0.8928 |
| 2 | 219017_at | ETNK1 | ethanolamine kinase 1 | -0.2843 |
| 3 | 220924_s_at | SLC38A2 | solute carrier family 38, member 2 | -0.6422 |
| 4 | 214587_at | COL8A1 | collagen, type VIII, alpha 1 | -0.921 |
| 5 | 202708_s_at | HIST2H2BE | histone cluster 2, H2be | -0.6984 |
| 6 | 204653_at | TFAP2A | transcription factor AP-2 alpha (activating enhancer binding protein 2 alpha) | -0.3942 |
| 7 | 206170_at | ADRB2 | adrenergic, beta-2-, receptor, surface | -0.8128 |
| 8 | 219503_s_at | TMEM40 | transmembrane protein 40 | -0.793 |
| 9 | 219522_at | FJX1 | four jointed box 1 (Drosophila) | -0.3654 |
| 10 | 218041_x_at | SLC38A2 | solute carrier family 38, member 2 | -0.5812 |
| 11 | 212774_at | ZNF238 | zinc finger protein 238 | -0.3771 |
| 12 | 202769_at | CCNG2 | cyclin G2 | -0.4408 |
| 13 | 201108_s_at | THBS1 | thrombospondin 1 | -0.8449 |
| 14 | 217579_x_at | null | null | -0.6055 |
| 15 | 222162_s_at | ADAMTS1 | ADAM metallopeptidase with thrombospondin type 1 motif, 1 | -1.2573 |
| 16 | 221676_s_at | CORO1C | coronin, actin binding protein, 1C | -0.2678 |
| 17 | 1598_g_at | GAS6 | growth arrest-specific 6 | -0.2796 |
| 18 | 222108_at | AMIGO2 | adhesion molecule with Ig-like domain 2 | -0.3826 |
| 19 | 213506_at | F2RL1 | coagulation factor II (thrombin) receptor-like 1 | -0.3562 |
| 20 | 211559_s_at | CCNG2 | cyclin G2 | -0.6733 |
| 21 | 202619_s_at | PLOD2 | procollagen-lysine, 2-oxoglutarate 5-dioxygenase 2 | -0.2883 |
| 22 | 212992_at | AHNAK2 | AHNAK nucleoprotein 2 | -0.8134 |
| 23 | 204917_s_at | MLLT3 | myeloid/lymphoid or mixed-lineage leukemia (trithorax homolog, Drosophila); translocated to, 3 | -0.8992 |
| 24 | 205239_at | AREG | amphiregulin | -0.5567 |
| 25 | 218440_at | MCCC1 | methylcrotonoyl-Coenzyme A carboxylase 1 (alpha) | -0.36 |
| 26 | 201368_at | ZFP36L2 | zinc finger protein 36, C3H type-like 2 | -0.691 |
| 27 | 219836_at | ZBED2 | zinc finger, BED-type containing 2 | -0.6671 |
| 28 | 204602_at | DKK1 | dickkopf homolog 1 (Xenopus laevis) | -0.7933 |
| 29 | 201739_at | SGK1 | serum/glucocorticoid regulated kinase 1 | -0.7944 |
| 30 | 217678_at | SLC7A11 | solute carrier family 7, (cationic amino acid transporter, y+ system) member 11 | -1.0269 |
| 31 | 221563_at | DUSP10 | dual specificity phosphatase 10 | -1.1129 |
| 32 | 201109_s_at | THBS1 | thrombospondin 1 | -1.2465 |
| 33 | 218319_at | PELI1 | pellino homolog 1 (Drosophila) | -0.3831 |
| 34 | 215813_s_at | PTGS1 | prostaglandin-endoperoxide synthase 1 (prostaglandin G/H synthase and cyclooxygenase) | -0.6398 |

FIG. 20B

| A | B | C | D | E |
|---|---|---|---|---|
| 35 | 35666_at | SEMA3F | sema domain, immunoglobulin domain (Ig), short basic domain, secreted, (semaphorin) 3F | -0.5912 |
| 36 | 204359_at | FLRT2 | fibronectin leucine rich transmembrane protein 2 | -1.6162 |
| 37 | 209815_at | PTCH1 | patched homolog 1 (Drosophila) | -0.5571 |
| 38 | 209921_at | SLC7A11 | solute carrier family 7, (cationic amino acid transporter, y+ system) member 11 | -1.1625 |
| 39 | 205157_s_at | KRT17 | keratin 17 | -0.5199 |
| 40 | 203966_s_at | PPM1A | protein phosphatase 1A (formerly 2C), magnesium-dependent, alpha isoform | -0.3188 |
| 41 | 215071_s_at | HIST1H2AC | histone cluster 1, H2ac | -0.6911 |
| 42 | 203640_at | MBNL2 | muscleblind-like 2 (Drosophila) | 0.6882 |
| 43 | 202874_s_at | ATP6V1C1 | ATPase, H+ transporting, lysosomal 42kDa, V1 subunit C1 | -0.2719 |
| 44 | 213568_at | OSR2 | odd-skipped related 2 (Drosophila) | -0.5205 |
| 45 | 209674_at | CRY1 | cryptochrome 1 (photolyase-like) | -0.2881 |
| 46 | 203946_s_at | ARG2 | arginase, type II | -0.3651 |
| 47 | 203476_at | TPBG | trophoblast glycoprotein | -0.3313 |
| 48 | 201010_s_at | TXNIP | thioredoxin interacting protein | -0.484 |
| 49 | 203865_s_at | ADARB1 | adenosine deaminase, RNA-specific, B1 (RED1 homolog rat) | -0.6168 |
| 50 | 216092_s_at | SLC7A8 | solute carrier family 7 (cationic amino acid transporter, y+ system), member 8 | -0.6647 |
| 51 | 218093_s_at | ANKRD10 | ankyrin repeat domain 10 | -0.3321 |
| 52 | 218886_at | PAK1IP1 | PAK1 interacting protein 1 | -0.5373 |
| 53 | 209101_at | CTGF | connective tissue growth factor | -0.8726 |
| 54 | 218973_at | EFTUD1 | elongation factor Tu GTP binding domain containing 1 | -0.3512 |
| 55 | 219250_s_at | FLRT3 | fibronectin leucine rich transmembrane protein 3 | -0.511 |
| 56 | 219284_at | HSPBAP1 | HSPB (heat shock 27kDa) associated protein 1 | -0.4041 |
| 57 | 205128_x_at | PTGS1 | prostaglandin-endoperoxide synthase 1 (prostaglandin G/H synthase and cyclooxygenase) | -0.4617 |
| 58 | 209758_s_at | MFAP5 | microfibrillar associated protein 5 | -0.3115 |
| 59 | 212386_at | TCF4 | transcription factor 4 | -0.4044 |
| 60 | 215501_s_at | DUSP10 | dual specificity phosphatase 10 | -1.4966 |
| 61 | 202922_at | GCLC | glutamate-cysteine ligase, catalytic subunit | -0.5437 |
| 62 | 209383_at | NR1H3 | DNA-damage-inducible transcript 3 | -0.3681 |
| 63 | 201341_at | ENC1 | ectodermal-neural cortex (with BTB-like domain) | -0.2838 |
| 64 | 215564_at | AREG | Amphiregulin | -1.0259 |
| 65 | 209180_at | RABGGTB | Rab geranylgeranyltransferase, beta subunit | -0.2769 |
| 66 | 200962_at | RPL31 | ribosomal protein L31 | -0.2799 |
| 67 | 212640_at | PTPLB | protein tyrosine phosphatase-like (proline instead of catalytic arginine), member b | -0.337 |
| 68 | 209946_at | VEGFC | vascular endothelial growth factor C | 0.919 |
| 69 | 204930_s_at | BNIP1 | BCL2/adenovirus E1B 19kDa interacting protein 1 | -0.499 |
| 70 | 200790_at | ODC1 | ornithine decarboxylase 1 | -0.3817 |
| 71 | 219383_at | PRR5L | proline rich 5 like | -1.2386 |
| 72 | 213624_at | SMPDL3A | sphingomyelin phosphodiesterase, acid-like 3A | -0.373 |

FIG. 20C

| A | B | C | D | E |
|---|---|---|---|---|
| 73 | 203521_s_at | ZNF318 | zinc finger protein 318 | -0.3655 |
| 74 | 210053_at | TAF5 | TAF5 RNA polymerase II, TATA box binding protein (TBP)-associated factor, 100kDa | -0.3104 |
| 75 | 213394_at | MAPKBP1 | mitogen-activated protein kinase binding protein 1 | -0.5511 |
| 76 | 202220_at | KIAA0907 | KIAA0907 | -0.2967 |
| 77 | 206156_at | GJB5 | gap junction protein, beta 5, 31.1kDa | -0.3179 |
| 78 | 207574_s_at | GADD45B | growth arrest and DNA-damage-inducible, beta | -0.4058 |
| 79 | 212190_at | SERPINE2 | serpin peptidase inhibitor, clade E (nexin, plasminogen activator inhibitor type 1), member 2 | -0.3244 |
| 80 | 215177_s_at | ITGA6 | integrin, alpha 6 | -0.6274 |
| 81 | 212236_x_at | KRT17 | keratin 17 | -0.3506 |
| 82 | 206343_s_at | NRG1 | neuregulin 1 | -0.5538 |
| 83 | 214702_at | FN1 | fibronectin 1 | -0.4768 |
| 84 | 201925_s_at | CD55 | CD55 molecule, decay accelerating factor for complement (Cromer blood group) | -1.1921 |
| 85 | 220147_s_at | FAM60A | family with sequence similarity 60, member A | -0.2787 |
| 86 | 208782_at | FSTL1 | follistatin-like 1 | -0.328 |
| 87 | 220318_at | EPN3 | epsin 3 | -0.9021 |
| 88 | 216840_s_at | LAMA2 | laminin, alpha 2 | -0.7282 |
| 89 | 214169_at | UNC84A | chromosome 7 open reading frame 20 | -0.5441 |
| 90 | 212614_at | ARID5B | AT rich interactive domain 5B (MRF1-like) | -0.9359 |
| 91 | 203332_s_at | INPP5D | inositol polyphosphate-5-phosphatase, 145kDa | -0.2639 |
| 92 | 205534_at | PCDH7 | protocadherin 7 | -0.4189 |
| 93 | 209296_at | PPM1B | protein phosphatase 1B (formerly 2C), magnesium-dependent, beta isoform | -0.2956 |
| 94 | 209457_at | DUSP5 | dual specificity phosphatase 5 | -0.3584 |
| 95 | 202162_s_at | CNOT8 | CCR4-NOT transcription complex, subunit 8 | -0.3347 |
| 96 | 210253_at | HTATIP2 | HIV-1 Tat interactive protein 2, 30kDa | -0.42 |
| 97 | 210495_x_at | FN1 | fibronectin 1 | -0.2788 |
| 98 | 202971_s_at | DYRK2 | dual-specificity tyrosine-(Y)-phosphorylation regulated kinase 2 | -0.3726 |
| 99 | 203778_at | MANBA | mannosidase, beta A, lysosomal | -0.3569 |
| 100 | 206332_s_at | IFI16 | interferon, gamma-inducible protein 16 | -0.3091 |
| 101 | 201926_s_at | CD55 | CD55 molecule, decay accelerating factor for complement (Cromer blood group) | -0.6336 |
| 102 | 217312_s_at | COL7A1 | collagen, type VII, alpha 1 | -0.4592 |
| 103 | 204204_at | SLC31A2 | solute carrier family 31 (copper transporters), member 2 | -0.4201 |
| 104 | 219492_at | CHIC2 | cysteine-rich hydrophobic domain 2 | -0.3578 |
| 105 | 205000_at | DDX3Y | DEAD (Asp-Glu-Ala-Asp) box polypeptide 3, Y-linked | -0.3032 |
| 106 | 216268_s_at | JAG1 | jagged 1 (Alagille syndrome) | -0.4457 |
| 107 | 218681_s_at | SDF2L1 | stromal cell-derived factor 2-like 1 | -0.41 |
| 108 | 204686_at | IRS1 | insulin receptor substrate 1 | -0.6245 |
| 109 | 201266_at | TXNRD1 | thioredoxin reductase 1 | -0.3622 |
| 110 | 209185_s_at | IRS2 | insulin receptor substrate 2 | -0.493 |

FIG. 20D

| A | B | C | D | E |
|---|---|---|---|---|
| 111 | 212464_s_at | FN1 | fibronectin 1 | -0.286 |
| 112 | 207528_s_at | SLC7A11 | solute carrier family 7, (cationic amino acid transporter, y+ system) member 11 | -0.4941 |
| 113 | 203743_s_at | TDG | thymine-DNA glycosylase | -0.3342 |
| 114 | 202923_s_at | GCLC | glutamate-cysteine ligase, catalytic subunit | -0.4933 |
| 115 | 219410_at | TMEM45A | transmembrane protein 45A | -0.2646 |
| 116 | 219073_s_at | OSBPL10 | oxysterol binding protein-like 10 | -0.278 |
| 117 | 200906_s_at | PALLD | palladin, cytoskeletal associated protein | -0.2632 |
| 118 | 202934_at | HK2 | hexokinase 2 | -0.3476 |
| 119 | 208527_x_at | HIST1H2BE | histone cluster 1, H2be | -0.2712 |
| 120 | 207375_s_at | IL15RA | interleukin 15 receptor, alpha | -0.6771 |
| 121 | 208070_s_at | REV3L | REV3-like, catalytic subunit of DNA polymerase zeta (yeast) | -0.3068 |
| 122 | 217663_at | ZNF234 | zinc finger protein 234 | -0.9228 |
| 123 | 206295_at | IL18 | interleukin 18 (interferon-gamma-inducing factor) | -0.4901 |
| 124 | 202770_s_at | CCNG2 | cyclin G2 | -0.4783 |
| 125 | 219142_at | RASL11B | RAS-like, family 11, member B | -0.4129 |
| 126 | 202766_s_at | CD93 | fibrillin 1 | -0.5256 |
| 127 | 221486_at | ENSA | endosulfine alpha | 0.6233 |
| 128 | 218107_at | WDR26 | WD repeat domain 26 | -0.3095 |
| 129 | 221596_s_at | C7ORF64 | chromosome 7 open reading frame 64 | -0.3947 |
| 130 | 202686_s_at | AXL | AXL receptor tyrosine kinase | -0.2651 |
| 131 | 209317_at | POLR1C | polymerase (RNA) I polypeptide C, 30kDa | -0.2754 |
| 132 | 203945_at | ARG2 | arginase, type II | -0.5513 |
| 133 | 205014_at | FGFBP1 | fibroblast growth factor binding protein 1 | -0.5121 |
| 134 | 206237_s_at | NRG1 | neuregulin 1 | -0.6744 |
| 135 | 205116_at | LAMA2 | laminin, alpha 2 | -0.6495 |
| 136 | 217125_at | null | null | -0.3499 |
| 137 | 205097_at | SLC26A2 | solute carrier family 26 (sulfate transporter), member 2 | -0.4357 |
| 138 | 212765_at | CAMSAP1L1 | calmodulin regulated spectrin-associated protein 1-like 1 | -0.305 |
| 139 | 219610_at | RGNEF | Rho-guanine nucleotide exchange factor | -0.5202 |
| 140 | 218178_s_at | CHMP1B | chromatin modifying protein 1B | -0.3549 |
| 141 | 213807_x_at | MET | met proto-oncogene (hepatocyte growth factor receptor) | -0.316 |
| 142 | 207876_s_at | FLNC | filamin C, gamma | -0.3615 |
| 143 | 221276_s_at | SYNC | syncoilin, intermediate filament protein | -0.3407 |
| 144 | 219710_at | SH3TC2 | SH3 domain and tetratricopeptide repeats 2 | -0.3552 |
| 145 | 217127_at | CTH | cystathionase (cystathionine gamma-lyase) | -0.646 |
| 146 | 202876_s_at | PBX2 | pre-B-cell leukemia homeobox 2 | -0.7106 |
| 147 | 220979_s_at | ST6GALNAC5 | ST6 (alpha-N-acetyl-neuraminyl-2,3-beta-galactosyl-1,3)-N-acetylgalactosaminide alpha-2,6-sialyltransferase 5 | -0.8082 |
| 148 | 201906_s_at | CTDSPL | CTD (carboxy-terminal domain, RNA polymerase II, polypeptide A) small phosphatase-like | -0.3999 |
| 149 | 204068_at | STK3 | serine/threonine kinase 3 (STE20 homolog, yeast) | -0.3974 |
| 150 | 202364_at | MXI1 | MAX interactor 1 | -0.5136 |
| 151 | 204584_at | L1CAM | L1 cell adhesion molecule | -0.3066 |

FIG. 20E

| A | B | C | D | E |
|---|---|---|---|---|
| 152 | 222262_s_at | ETNK1 | ethanolamine kinase 1 | -0.3293 |
| 153 | 209099_x_at | JAG1 | jagged 1 (Alagille syndrome) | -0.3677 |
| 154 | 202342_s_at | TRIM2 | tripartite motif-containing 2 | -0.5202 |
| 155 | 212660_at | PHF15 | PHD finger protein 15 | -0.3879 |
| 156 | 221249_s_at | FAM117A | family with sequence similarity 117, member A | -0.5604 |
| 157 | 206032_at | DSC3 | desmocollin 3 | -0.3112 |
| 158 | 204532_x_at | UGT1A10 | UDP glucuronosyltransferase 1 family, polypeptide A1 | -0.5293 |
| 159 | 220262_s_at | DLK2 | delta-like 2 homolog (Drosophila) | -0.2829 |
| 160 | 217599_s_at | MDFIC | MyoD family inhibitor domain containing | -0.3258 |
| 161 | 219885_at | SLFN12 | schlafen family member 12 | -0.4383 |
| 162 | 216309_x_at | JRK | jerky homolog (mouse) | -0.6743 |
| 163 | 218358_at | CRELD2 | cysteine-rich with EGF-like domains 2 | -0.4017 |
| 164 | 210765_at | CSE1L | CSE1 chromosome segregation 1-like (yeast) | -0.4052 |
| 165 | 202730_s_at | PDCD4 | programmed cell death 4 (neoplastic transformation inhibitor) | -0.4477 |
| 166 | 214909_s_at | DDAH2 | dimethylarginine dimethylaminohydrolase 2 | -0.3615 |
| 167 | 202973_x_at | FAM13A | family with sequence similarity 13, member A | -0.3649 |
| 168 | 211986_at | AHNAK | AHNAK nucleoprotein | -0.3579 |
| 169 | 203612_at | BYSL | bystin-like | -0.2825 |
| 170 | 216918_s_at | DST | dystonin | -0.9163 |
| 171 | 219390_at | FKBP14 | FK506 binding protein 14, 22 kDa | -0.3488 |
| 172 | 220240_s_at | TMCO3 | transmembrane and coiled-coil domains 3 | -0.4286 |
| 173 | 205662_at | B9D1 | B9 protein domain 1 | -0.5494 |
| 174 | 209633_at | PPP2R3A | protein phosphatase 2 (formerly 2A), regulatory subunit B", alpha | -0.284 |
| 175 | 203889_at | SCG5 | secretogranin V (7B2 protein) | -1.2842 |
| 176 | 205535_s_at | PCDH7 | protocadherin 7 | -0.6199 |
| 177 | 219026_s_at | RASAL2 | RAS protein activator like 2 | -0.6331 |
| 178 | 205018_s_at | MBNL2 | muscleblind-like 2 (Drosophila) | -0.8339 |
| 179 | 201426_s_at | VIM | vimentin | -0.3397 |
| 180 | 214093_s_at | FUBP1 | far upstream element (FUSE) binding protein 1 | -0.2702 |
| 181 | 203637_s_at | MID1 | midline 1 (Opitz/BBB syndrome) | -0.3946 |
| 182 | 212667_at | SPARC | secreted protein, acidic, cysteine-rich (osteonectin) | -0.3021 |
| 183 | 207347_at | ERCC6 | excision repair cross-complementing rodent repair deficiency, complementation group 6 | -0.4751 |
| 184 | 205415_s_at | ATXN3 | ataxin 3 | -0.4155 |
| 185 | 215767_at | ZNF804A | zinc finger protein 804A | -0.449 |
| 186 | 219529_at | CLIC3 | chloride intracellular channel 3 | -0.4138 |
| 187 | 211974_x_at | RBPJ | recombination signal binding protein for immunoglobulin kappa J region | -0.2718 |
| 188 | 209900_s_at | SLC16A1 | solute carrier family 16, member 1 (monocarboxylic acid transporter 1) | -0.3323 |
| 189 | 209160_at | AKR1C3 | aldo-keto reductase family 1, member C3 (3-alpha hydroxysteroid dehydrogenase, type II) | -0.5025 |
| 190 | 204014_at | DUSP4 | dual specificity phosphatase 4 | -0.479 |

FIG. 20F

| A | B | C | D | E |
|---|---|---|---|---|
| 191 | 212124_at | ZMIZ1 | zinc finger, MIZ-type containing 1 | -0.3095 |
| 192 | 210220_at | FZD2 | frizzled homolog 2 (Drosophila) | -0.9973 |
| 193 | 203096_s_at | RAPGEF2 | Rap guanine nucleotide exchange factor (GEF) 2 | -0.4912 |
| 194 | 210105_s_at | FYN | FYN oncogene related to SRC, FGR, YES | -0.2872 |
| 195 | 202551_s_at | CRIM1 | cysteine rich transmembrane BMP regulator 1 (chordin-like) | -0.4053 |
| 196 | 205264_at | CD3EAP | CD3e molecule, epsilon associated protein | -0.3608 |
| 197 | 202267_at | LAMC2 | laminin, gamma 2 | -0.3922 |
| 198 | 204136_at | COL7A1 | collagen, type VII, alpha 1 | -0.5442 |
| 199 | 207147_at | DLX2 | distal-less homeobox 2 | -0.631 |
| 200 | 209699_x_at | AKR1C2 | aldo-keto reductase family 1, member C2 (dihydrodiol dehydrogenase 2; bile acid binding protein; 3-alpha hydroxysteroid dehydrogenase, type III) | -0.6079 |

FIG. 21A

Table O: RA Benchmark Signature in BJ fibroblasts, 200 up-regulated

| Rank | Probe set ID | Acronym | NetAffx Title | Log2FC tRA to DMSO |
|---|---|---|---|---|
| 1 | 203108_at | GPRC5A | G protein-coupled receptor, family C, group 5, member A | 1.3625 |
| 2 | 221541_at | CRISPLD2 | cysteine-rich secretory protein LCCL domain containing 2 | 0.9181 |
| 3 | 218729_at | LXN | latexin | 2.0417 |
| 4 | 201042_at | TGM2 | transglutaminase 2 (C polypeptide, protein-glutamine-gamma-glutamyltransferase) | 0.9431 |
| 5 | 216598_s_at | CCL2 | chemokine (C-C motif) ligand 2 | 1.8525 |
| 6 | 209955_s_at | FAP | fibroblast activation protein, alpha | 0.5744 |
| 7 | 203221_at | TLE1 | transducin-like enhancer of split 1 (E(sp1) homolog, Drosophila) | 0.748 |
| 8 | 219634_at | CHST11 | carbohydrate (chondroitin 4) sulfotransferase 11 | 1.5609 |
| 9 | 208394_x_at | ESM1 | endothelial cell-specific molecule 1 | 1.1629 |
| 10 | 212774_at | ZNF238 | zinc finger protein 238 | 0.7088 |
| 11 | 200832_s_at | SCD | stearoyl-CoA desaturase (delta-9-desaturase) | 0.4878 |
| 12 | 209505_at | NR2F1 | Nuclear receptor subfamily 2, group F, member 1 | 0.8618 |
| 13 | 203738_at | C5ORF22 | chromosome 5 open reading frame 22 | 0.4334 |
| 14 | 202071_at | SDC4 | syndecan 4 | 0.4633 |
| 15 | 210257_x_at | CUL4B | cullin 4B | 0.737 |
| 16 | 202037_s_at | SFRP1 | secreted frizzled-related protein 1 | 0.37 |
| 17 | 212183_at | NUDT4 | nudix (nucleoside diphosphate linked moiety X)-type motif 4 | 0.4346 |
| 18 | 220890_s_at | DDX47 | DEAD (Asp-Glu-Ala-Asp) box polypeptide 47 | 0.2821 |
| 19 | 217220_at | null | null | 0.2847 |
| 20 | 212771_at | FAM171A1 | family with sequence similarity 171, member A1 | 0.4845 |
| 21 | 205479_s_at | PLAU | plasminogen activator, urokinase | 0.5925 |
| 22 | 221872_at | RARRES1 | retinoic acid receptor responder (tazarotene induced) 1 | 1.6866 |
| 23 | 218627_at | DRAM1 | DNA-damage regulated autophagy modulator 1 | 0.7323 |
| 24 | 203372_s_at | SOCS2 | suppressor of cytokine signaling 2 | 0.5961 |
| 25 | 218284_at | SMAD3 | SMAD family member 3 | 0.7557 |
| 26 | 208868_s_at | GABARAPL1 | GABA(A) receptor-associated protein like 1 | 0.5311 |
| 27 | 202600_s_at | NRIP1 | nuclear receptor interacting protein 1 | 0.7979 |
| 28 | 209829_at | FAM65B | family with sequence similarity 65, member B | 1.3803 |
| 29 | 202388_at | RGS2 | regulator of G-protein signaling 2, 24kDa | 2.2025 |
| 30 | 209278_s_at | TFPI2 | tissue factor pathway inhibitor 2 | 0.4619 |
| 31 | 205870_at | BDKRB2 | bradykinin receptor B2 | 3.3064 |
| 32 | 202481_at | DHRS3 | dehydrogenase/reductase (SDR family) member 3 | 3.8459 |
| 33 | 208131_s_at | PTGIS | prostaglandin I2 (prostacyclin) synthase | 1.0664 |

FIG. 21B

| A | B | C | D | E |
|---|---|---|---|---|
| 34 | 205005_s_at | NMT2 | N-myristoyltransferase 2 | 0.5796 |
| 35 | 201829_at | NET1 | neuroepithelial cell transforming 1 | 0.4995 |
| 36 | 204597_x_at | STC1 | stanniocalcin 1 | 1.0786 |
| 37 | 212444_at | null | null | 1.7489 |
| 38 | 207510_at | BDKRB1 | bradykinin receptor B1 | 1.4604 |
| 39 | 212658_at | LHFPL2 | lipoma HMGIC fusion partner-like 2 | 1.0164 |
| 40 | 204326_x_at | MT1X | metallothionein 1X | 0.3536 |
| 41 | 202599_s_at | NRIP1 | nuclear receptor interacting protein 1 | 0.7276 |
| 42 | 202214_s_at | CUL4B | cullin 4B | 0.5003 |
| 43 | 201309_x_at | C5ORF13 | chromosome 5 open reading frame 13 | 0.288 |
| 44 | 208966_x_at | IFI16 | interferon, gamma-inducible protein 16 | 0.3841 |
| 45 | 204595_s_at | STC1 | stanniocalcin 1 | 0.921 |
| 46 | 202016_at | MEST | mesoderm specific transcript homolog (mouse) | 0.8671 |
| 47 | 202213_s_at | CUL4B | cullin 4B | 0.5771 |
| 48 | 202859_x_at | IL8 | interleukin 8 | 0.8788 |
| 49 | 39402_at | IL1B | interleukin 1, beta | 1.8726 |
| 50 | 201596_x_at | KRT18 | keratin 18 | 0.7929 |
| 51 | 212143_s_at | IGFBP3 | insulin-like growth factor binding protein 3 | 0.3455 |
| 52 | 205532_s_at | CDH6 | cadherin 6, type 2, K-cadherin (fetal kidney) | 1.3836 |
| 53 | 213497_at | ABTB2 | ankyrin repeat and BTB (POZ) domain containing 2 | 0.8881 |
| 54 | 202637_s_at | ICAM1 | intercellular adhesion molecule 1 | 0.3426 |
| 55 | 203373_at | SOCS2 | suppressor of cytokine signaling 2 | 0.5789 |
| 56 | 204254_s_at | VDR | vitamin D (1,25- dihydroxyvitamin D3) receptor | 1.0195 |
| 57 | 212624_s_at | CHN1 | chimerin (chimaerin) 1 | 0.5204 |
| 58 | 210002_at | GATA6 | GATA binding protein 6 | 1.9963 |
| 59 | 212859_x_at | MT1E | metallothionein 1E | 0.3369 |
| 60 | 218129_s_at | NFYB | nuclear transcription factor Y, beta | 0.4517 |
| 61 | 211668_s_at | PLAU | plasminogen activator, urokinase | 0.5471 |
| 62 | 205006_s_at | NMT2 | N-myristoyltransferase 2 | 0.8617 |
| 63 | 201150_s_at | TIMP3 | TIMP metallopeptidase inhibitor 3 | 0.8897 |
| 64 | 40148_at | APBB2 | amyloid beta (A4) precursor protein-binding, family B, member 2 | 0.6447 |
| 65 | 201310_s_at | C5ORF13 | chromosome 5 open reading frame 13 | 0.3366 |
| 66 | 212093_s_at | MTUS1 | mitochondrial tumor suppressor 1 | 0.9264 |
| 67 | 213419_at | APBB2 | amyloid beta (A4) precursor protein-binding, family B, member 2 | 0.6732 |
| 68 | 209488_s_at | RBPMS | RNA binding protein with multiple splicing | 0.3451 |
| 69 | 202949_s_at | FHL2 | four and a half LIM domains 2 | 0.5221 |
| 70 | 205990_s_at | WNT5A | wingless-type MMTV integration site family, member 5A | 0.3945 |
| 71 | 218189_s_at | NANS | N-acetylneuraminic acid synthase | 0.5318 |
| 72 | 218589_at | LPAR6 | lysophosphatidic acid receptor 6 | 0.4024 |
| 73 | 212793_at | DAAM2 | dishevelled associated activator of morphogenesis 2 | 0.3829 |
| 74 | 203140_at | BCL6 | B-cell CLL/lymphoma 6 | 0.2978 |

FIG. 21C

| A | B | C | D | E |
|---|---|---|---|---|
| 75 | 37433_at | PIAS2 | protein inhibitor of activated STAT, 2 | 0.3174 |
| 76 | 217165_x_at | MT1F | metallothionein 1F | 0.405 |
| 77 | 218211_s_at | MLPH | melanophilin | 0.5831 |
| 78 | 206707_x_at | FAM65B | family with sequence similarity 65, member B | 1.2142 |
| 79 | 202295_s_at | CTSH | cathepsin H | 0.9289 |
| 80 | 210517_s_at | AKAP12 | A kinase (PRKA) anchor protein 12 | 0.6146 |
| 81 | 201147_s_at | TIMP3 | TIMP metallopeptidase inhibitor 3 | 0.6231 |
| 82 | 205067_at | IL1B | interleukin 1, beta | 0.9873 |
| 83 | 209501_at | CDR2 | cerebellar degeneration-related protein 2, 62kDa | 0.3248 |
| 84 | 218739_at | ABHD5 | abhydrolase domain containing 5 | 0.3138 |
| 85 | 200878_at | EPAS1 | endothelial PAS domain protein 1 | 0.4131 |
| 86 | 210367_s_at | PTGES | prostaglandin E synthase | 1.1257 |
| 87 | 219509_at | MYOZ1 | myozenin 1 | 0.3852 |
| 88 | 209506_s_at | NR2F1 | nuclear receptor subfamily 2, group F, member 1 | 0.7604 |
| 89 | 218269_at | RNASEN | ribonuclease type III, nuclear | 0.3649 |
| 90 | 215997_s_at | CUL4B | cullin 4B | 0.7785 |
| 91 | 202446_s_at | PLSCR1 | phospholipid scramblase 1 | 0.345 |
| 92 | 219179_at | DACT1 | dapper, antagonist of beta-catenin, homolog 1 (Xenopus laevis) | 0.7865 |
| 93 | 205234_at | SLC16A4 | solute carrier family 16, member 4 (monocarboxylic acid transporter 5) | 0.8155 |
| 94 | 203153_at | IFIT1 | interferon-induced protein with tetratricopeptide repeats 1 | 0.3926 |
| 95 | 209487_at | RBPMS | RNA binding protein with multiple splicing | 0.3471 |
| 96 | 213661_at | PAMR1 | peptidase domain containing associated with muscle regeneration 1 | 0.302 |
| 97 | 204541_at | SEC14L2 | SEC14-like 2 (S. cerevisiae) | 0.9893 |
| 98 | 212224_at | ALDH1A1 | aldehyde dehydrogenase 1 family, member A1 | 0.4935 |
| 99 | 209723_at | SERPINB9 | serpin peptidase inhibitor, clade B (ovalbumin), member 9 | 0.7879 |
| 100 | 201416_at | SOX4 | SRY (sex determining region Y)-box 4 | 0.9518 |
| 101 | 207836_s_at | RBPMS | RNA binding protein with multiple splicing | 0.4986 |
| 102 | 218025_s_at | PECI | peroxisomal D3,D2-enoyl-CoA isomerase | 0.2676 |
| 103 | 204798_at | MYB | v-myb myeloblastosis viral oncogene homolog (avian) | 1.0438 |
| 104 | 205080_at | RARB | retinoic acid receptor, beta | 1.3424 |
| 105 | 212181_s_at | NUDT4 | nudix (nucleoside diphosphate linked moiety X)-type motif 4 | 0.3351 |
| 106 | 221582_at | HIST3H2A | histone cluster 3, H2a | 0.5044 |
| 107 | 221009_s_at | ANGPTL4 | angiopoietin-like 4 | 1.9519 |
| 108 | 214803_at | null | null | 0.7566 |
| 109 | 202575_at | CRABP2 | cellular retinoic acid binding protein 2 | 1.1069 |
| 110 | 212418_at | ELF1 | E74-like factor 1 (ets domain transcription factor) | 0.4226 |
| 111 | 203131_at | PDGFRA | platelet-derived growth factor receptor, alpha polypeptide | 0.5284 |

FIG. 21D

| A | B | C | D | E |
|---|---|---|---|---|
| 112 | 213502_x_at | LOC91316 | glucuronidase, beta/ immunoglobulin lambda-like polypeptide 1 pseudogene | 1.1581 |
| 113 | 202291_s_at | MGP | matrix Gla protein | 0.8472 |
| 114 | 206461_x_at | MT1H | metallothionein 1H | 0.3609 |
| 115 | 201939_at | PLK2 | polo-like kinase 2 (Drosophila) | 0.746 |
| 116 | 219691_at | SAMD9 | sterile alpha motif domain containing 9 | 1.6165 |
| 117 | 63825_at | ABHD2 | abhydrolase domain containing 2 | 0.5925 |
| 118 | 203234_at | UPP1 | uridine phosphorylase 1 | 0.5422 |
| 119 | 201830_s_at | NET1 | neuroepithelial cell transforming 1 | 0.447 |
| 120 | 219715_s_at | TDP1 | tyrosyl-DNA phosphodiesterase 1 | 0.2781 |
| 121 | 202288_at | MTOR | mechanistic target of rapamycin (serine/threonine kinase) | 0.4335 |
| 122 | 204255_s_at | VDR | vitamin D (1,25- dihydroxyvitamin D3) receptor | 0.6404 |
| 123 | 202036_s_at | SFRP1 | secreted frizzled-related protein 1 | 0.4429 |
| 124 | 216336_x_at | MT1E | metallothionein 1E | 0.2757 |
| 125 | 211456_x_at | MT1P2 | metallothionein 1 pseudogene 2 | 0.5672 |
| 126 | 221577_x_at | LOC100292463 | growth differentiation factor 15 | 0.7846 |
| 127 | 218292_s_at | PRKAG2 | protein kinase, AMP-activated, gamma 2 non-catalytic subunit | 0.6696 |
| 128 | 210195_s_at | PSG1 | pregnancy specific beta-1-glycoprotein 1 | 0.3147 |
| 129 | 213805_at | ABHD5 | abhydrolase domain containing 5 | 0.2828 |
| 130 | 206114_at | EPHA4 | EPH receptor A4 | 1.4513 |
| 131 | 221002_s_at | TSPAN14 | tetraspanin 14 | 0.3871 |
| 132 | 201669_s_at | MARCKS | myristoylated alanine-rich protein kinase C substrate | 0.2788 |
| 133 | 219749_at | SH2D4A | SH2 domain containing 4A | 0.6436 |
| 134 | 201417_at | SOX4 | SRY (sex determining region Y)-box 4 | 0.7638 |
| 135 | 206765_at | KCNJ2 | potassium inwardly-rectifying channel, subfamily J, member 2 | 0.9798 |
| 136 | 220161_s_at | EPB41L4B | erythrocyte membrane protein band 4.1 like 4B | 0.826 |
| 137 | 205027_s_at | MAP3K8 | mitogen-activated protein kinase kinase kinase 8 | 1.0325 |
| 138 | 207680_x_at | PAX3 | paired box 3 | 0.3762 |
| 139 | 202976_s_at | RHOBTB3 | Rho-related BTB domain containing 3 | 0.2701 |
| 140 | 207069_s_at | SMAD6 | SMAD family member 6 | 0.579 |
| 141 | 203629_s_at | COG5 | component of oligomeric golgi complex 5 | 0.2895 |
| 142 | 201148_s_at | TIMP3 | TIMP metallopeptidase inhibitor 3 | 0.3736 |
| 143 | 219283_at | C1GALT1C1 | C1GALT1-specific chaperone 1 | 0.3228 |
| 144 | 211711_s_at | PTEN | phosphatase and tensin homolog | 0.2652 |
| 145 | 214277_at | COX11 | COX11 homolog, cytochrome c oxidase assembly protein (yeast) | 0.2793 |
| 146 | 201662_s_at | ACSL3 | acyl-CoA synthetase long-chain family member 3 | 0.3182 |
| 147 | 205085_at | ORC1L | origin recognition complex, subunit 1-like (yeast) | 0.5129 |
| 148 | 213260_at | FOXC1 | forkhead box C1 | 0.5026 |
| 149 | 201860_s_at | PLAT | plasminogen activator, tissue | 0.5541 |
| 150 | 204146_at | RAD51AP1 | RAD51 associated protein 1 | 0.2781 |

FIG. 21E

| A | B | C | D | E |
|---|---|---|---|---|
| 151 | 204010_s_at | KRAS | v-Ki-ras2 Kirsten rat sarcoma viral oncogene homolog | 0.643 |
| 152 | 203656_at | FIG4 | FIG4 homolog (S. cerevisiae) | 0.2889 |
| 153 | 209409_at | GRB10 | growth factor receptor-bound protein 10 | 0.3779 |
| 154 | 203355_s_at | PSD3 | pleckstrin and Sec7 domain containing 3 | 0.87 |
| 155 | 202035_s_at | SFRP1 | secreted frizzled-related protein 1 | 0.5473 |
| 156 | 210095_s_at | IGFBP3 | insulin-like growth factor binding protein 3 | 0.324 |
| 157 | 214783_s_at | ANXA11 | annexin A11 | 0.3222 |
| 158 | 210612_s_at | SYNJ2 | synaptojanin 2 | 0.6355 |
| 159 | 200701_at | NPC2 | Niemann-Pick disease, type C2 | 0.2681 |
| 160 | 215774_s_at | null | null | 0.5239 |
| 161 | 210512_s_at | VEGFA | vascular endothelial growth factor A | 0.8526 |
| 162 | 215182_x_at | null | null | 0.4776 |
| 163 | 206240_s_at | ZNF136 | zinc finger protein 136 | 0.2861 |
| 164 | 208713_at | HNRNPUL1 | heterogeneous nuclear ribonucleoprotein U-like 1 | 0.2701 |
| 165 | 210802_s_at | DIMT1L | DIM1 dimethyladenosine transferase 1-like (S. cerevisiae) | 0.3021 |
| 166 | 206675_s_at | SKIL | SKI-like oncogene | 0.551 |
| 167 | 216180_s_at | SYNJ2 | synaptojanin 2 | 0.3531 |
| 168 | 221530_s_at | BHLHE41 | basic helix-loop-helix family, member e41 | 0.9186 |
| 169 | 209166_s_at | MAN2B1 | mannosidase, alpha, class 2B, member 1 | 0.4027 |
| 170 | 212268_at | SERPINB1 | serpin peptidase inhibitor, clade B (ovalbumin), member 1 | 0.4717 |
| 171 | 202094_at | BIRC5 | baculoviral IAP repeat-containing 5 | 0.2701 |
| 172 | 213425_at | WNT5A | wingless-type MMTV integration site family, member 5A | 0.507 |
| 173 | 218820_at | C14ORF132 | chromosome 14 open reading frame 132 | 0.597 |
| 174 | 218812_s_at | ORAI2 | ORAI calcium release-activated calcium modulator 2 | 0.5284 |
| 175 | 217853_at | TNS3 | tensin 3 | 0.4939 |
| 176 | 203394_s_at | HES1 | hairy and enhancer of split 1, (Drosophila) | 0.5153 |
| 177 | 218610_s_at | CPPED1 | calcineurin-like phosphoesterase domain containing 1 | 0.37 |
| 178 | 217783_s_at | YPEL5 | yippee-like 5 (Drosophila) | 0.2719 |
| 179 | 219166_at | C14ORF104 | chromosome 14 open reading frame 104 | 0.3152 |
| 180 | 202393_s_at | KLF10 | Kruppel-like factor 10 | 0.3119 |
| 181 | 217692_at | MAGOH2 | mago-nashi homolog 2, proliferation-associated (Drosophila) | 0.5192 |
| 182 | 209277_at | TFPI2 | tissue factor pathway inhibitor 2 | 0.4256 |
| 183 | 205174_s_at | QPCT | glutaminyl-peptide cyclotransferase | 0.3304 |
| 184 | 205398_s_at | SMAD3 | SMAD family member 3 | 0.6882 |
| 185 | 203851_at | IGFBP6 | insulin-like growth factor binding protein 6 | 0.4301 |
| 186 | 212786_at | CLEC16A | C-type lectin domain family 16, member A | 0.5266 |
| 187 | 206084_at | PTPRR | protein tyrosine phosphatase, receptor type, R | 0.7848 |
| 188 | 205743_at | STAC | SH3 and cysteine rich domain | 0.4111 |

FIG. 21F

| A | B | C | D | E |
|---|---|---|---|---|
| 189 | 206586_at | CNR2 | cannabinoid receptor 2 (macrophage) | 0.403 |
| 190 | 219901_at | FGD6 | FYVE, RhoGEF and PH domain containing 6 | 0.7331 |
| 191 | 221019_s_at | COLEC12 | collectin sub-family member 12 | 0.6698 |
| 192 | 212970_at | APBB2 | amyloid beta (A4) precursor protein-binding, family B, member 2 | 0.361 |
| 193 | 220186_s_at | PCDH24 | protocadherin 24 | 0.7735 |
| 194 | 212972_x_at | APBB2 | amyloid beta (A4) precursor protein-binding, family B, member 2 | 0.6666 |
| 195 | 203098_at | CDYL | chromodomain protein, Y-like | 0.357 |
| 196 | 51158_at | FAM174B | family with sequence similarity 174, member B | 0.751 |
| 197 | 219759_at | ERAP2 | endoplasmic reticulum aminopeptidase 2 | 0.561 |
| 198 | 203504_s_at | ABCA1 | ATP-binding cassette, sub-family A (ABC1), member 1 | 0.9099 |
| 199 | 205885_s_at | ITGA4 | integrin, alpha 4 (antigen CD49D, alpha 4 subunit of VLA-4 receptor) | 0.2878 |
| 200 | 201149_s_at | TIMP3 | TIMP metallopeptidase inhibitor 3 | 0.5748 |

FIG. 22A

Table P: RA Benchmark Signature in BJ fibroblast, 200 down-regulated

| A Rank | B Probe set ID | C Acronym | D NetAffx Title | E Log2FC tRA to DMSO |
|---|---|---|---|---|
| 1 | 210120_s_at | RANBP3 | RAN binding protein 3 | -0.4156 |
| 2 | 216236_s_at | SLC2A14 | solute carrier family 2 (facilitated glucose transporter), member 14 | -0.5463 |
| 3 | 206924_at | IL11 | interleukin 11 | -0.5997 |
| 4 | 204933_s_at | TNFRSF11B | tumor necrosis factor receptor superfamily, member 11b | -0.9241 |
| 5 | 213496_at | LPPR4 | plasticity related gene 1 | -0.4718 |
| 6 | 209288_s_at | CDC42EP3 | CDC42 effector protein (Rho GTPase binding) 3 | -0.3328 |
| 7 | 204011_at | SPRY2 | sprouty homolog 2 (Drosophila) | -0.6182 |
| 8 | 222162_s_at | ADAMTS1 | ADAM metallopeptidase with thrombospondin type 1 motif, 1 | -1.0195 |
| 9 | 201423_s_at | CUL4A | cullin 4A | -0.29 |
| 10 | 209386_at | TM4SF1 | transmembrane 4 L six family member 1 | -1.0503 |
| 11 | 204948_s_at | FST | follistatin | -0.7054 |
| 12 | 209841_s_at | LRRN3 | leucine rich repeat neuronal 3 | -1.3782 |
| 13 | 215034_s_at | TM4SF1 | transmembrane 4 L six family member 1 | -0.7015 |
| 14 | 213906_at | MYBL1 | v-myb myeloblastosis viral oncogene homolog (avian)-like 1 | -0.6493 |
| 15 | 215336_at | AKAP11 | A kinase (PRKA) anchor protein 11 | -0.7124 |
| 16 | 206157_at | PTX3 | pentraxin-related gene, rapidly induced by IL-1 beta | -0.7367 |
| 17 | 210310_s_at | FGF5 | fibroblast growth factor 5 | -0.3979 |
| 18 | 204014_at | DUSP4 | dual specificity phosphatase 4 | -0.7517 |
| 19 | 204872_at | TLE4 | transducin-like enhancer of split 4 (E(sp1) homolog, Drosophila) | -0.6695 |
| 20 | 221528_s_at | ELMO2 | engulfment and cell motility 2 | -0.5656 |
| 21 | 203794_at | CDC42BPA | CDC42 binding protein kinase alpha (DMPK-like) | -0.3263 |
| 22 | 212915_at | PDZRN3 | PDZ domain containing ring finger 3 | -0.5008 |
| 23 | 208961_s_at | KLF6 | Kruppel-like factor 6 | -0.5552 |
| 24 | 206814_at | NGF | nerve growth factor (beta polypeptide) | -0.374 |
| 25 | 212745_s_at | BBS4 | Bardet-Biedl syndrome 4 | -0.4494 |
| 26 | 203476_at | TPBG | trophoblast glycoprotein | -0.379 |
| 27 | 208025_s_at | HMGA2 | high mobility group AT-hook 2 | -0.6864 |
| 28 | 201363_s_at | IVNS1ABP | influenza virus NS1A binding protein | -0.2912 |
| 29 | 218706_s_at | GRAMD3 | GRAM domain containing 3 | -0.3717 |
| 30 | 212230_at | PPAP2B | phosphatidic acid phosphatase type 2B | -0.3096 |
| 31 | 201395_at | RBM5 | RNA binding motif protein 5 | -0.2941 |
| 32 | 209387_s_at | TM4SF1 | transmembrane 4 L six family member 1 | -0.6837 |
| 33 | 60474_at | FERMT1 | fermitin family homolog 1 (Drosophila) | -0.3397 |
| 34 | 202708_s_at | HIST2H2BE | histone cluster 2, H2be | -0.3994 |
| 35 | 220116_at | KCNN2 | potassium intermediate/small conductance calcium-activated channel, subfamily N, member 2 | -0.5252 |
| 36 | 221696_s_at | STYK1 | serine/threonine/tyrosine kinase 1 | -0.7139 |

FIG. 22B

| A | B | C | D | E |
|---|---|---|---|---|
| 37 | 212543_at | AIM1 | absent in melanoma 1 | -0.7158 |
| 38 | 207303_at | PDE1C | phosphodiesterase 1C, calmodulin-dependent 70kDa | -0.7434 |
| 39 | 222065_s_at | FLI1 | flightless I homolog (Drosophila) | -0.3338 |
| 40 | 209840_s_at | LRRN3 | leucine rich repeat neuronal 3 | -1.0104 |
| 41 | 205590_at | RASGRP1 | RAS guanyl releasing protein 1 (calcium and DAG-regulated) | -0.7491 |
| 42 | 208482_at | SSTR1 | somatostatin receptor 1 | -0.9081 |
| 43 | 219973_at | ARSJ | arylsulfatase family, member J | -0.3923 |
| 44 | 218469_at | GREM1 | gremlin 1, cysteine knot superfamily, homolog (Xenopus laevis) | -0.2983 |
| 45 | 204932_at | TNFRSF11B | tumor necrosis factor receptor superfamily, member 11b | -0.6024 |
| 46 | 203217_s_at | ST3GAL5 | ST3 beta-galactoside alpha-2,3-sialyltransferase 5 | -0.3615 |
| 47 | 208621_s_at | EZR | ezrin | -0.3911 |
| 48 | 203502_at | BPGM | 2,3-bisphosphoglycerate mutase | -0.4607 |
| 49 | 203708_at | PDE4B | phosphodiesterase 4B, cAMP-specific (phosphodiesterase E4 dunce homolog, Drosophila) | -0.6204 |
| 50 | 213103_at | STARD13 | StAR-related lipid transfer (START) domain containing 13 | -0.6942 |
| 51 | 203641_s_at | COBLL1 | COBL-like 1 | -0.5072 |
| 52 | 209286_at | CDC42EP3 | CDC42 effector protein (Rho GTPase binding) 3 | -0.4186 |
| 53 | 217678_at | SLC7A11 | solute carrier family 7, (cationic amino acid transporter, y+ system) member 11 | -0.7968 |
| 54 | 214002_at | null | null | -0.4733 |
| 55 | 212650_at | EHBP1 | EH domain binding protein 1 | -0.5593 |
| 56 | 204529_s_at | TOX | thymocyte selection-associated high mobility group box | -0.863 |
| 57 | 213684_s_at | PDLIM5 | PDZ and LIM domain 5 | -0.6056 |
| 58 | 213988_s_at | SAT1 | spermidine/spermine N1-acetyltransferase 1 | -0.48 |
| 59 | 205258_at | INHBB | inhibin, beta B | -0.5564 |
| 60 | 210261_at | KCNK2 | potassium channel, subfamily K, member 2 | -0.5251 |
| 61 | 213280_at | RAP1GAP2 | GTPase activating Rap/RanGAP domain-like 4 | -0.6691 |
| 62 | 203674_at | HELZ | helicase with zinc finger | -0.4658 |
| 63 | 210511_s_at | INHBA | inhibin, beta A | -0.7116 |
| 64 | 214438_at | HLX | H2.0-like homeobox | -0.4443 |
| 65 | 207980_s_at | CITED2 | Cbp/p300-interacting transactivator, with Glu/Asp-rich carboxy-terminal domain, 2 | -0.5567 |
| 66 | 215498_s_at | MAP2K3 | mitogen-activated protein kinase kinase 3 | -0.4196 |
| 67 | 208727_s_at | CDC42 | cell division cycle 42 (GTP binding protein, 25kDa) | -0.3156 |
| 68 | 221685_s_at | CCDC99 | coiled-coil domain containing 99 | -0.356 |
| 69 | 203404_at | ARMCX2 | armadillo repeat containing, X-linked 2 | -0.2636 |
| 70 | 202677_at | RASA1 | RAS p21 protein activator (GTPase activating protein) 1 | -0.3236 |
| 71 | 205880_at | PRKD1 | protein kinase D1 | -0.4913 |
| 72 | 203987_at | FZD6 | frizzled homolog 6 (Drosophila) | -0.2728 |
| 73 | 212539_at | CHD1L | chromodomain helicase DNA binding protein 1-like | -0.3093 |
| 74 | 201133_s_at | PJA2 | praja ring finger 2 | -0.3331 |
| 75 | 218376_s_at | MICAL1 | microtubule associated monoxygenase, calponin and LIM domain containing 1 | -0.2749 |

FIG. 22C

| A | B | C | D | E |
|---|---|---|---|---|
| 76 | 218468_s_at | GREM1 | gremlin 1, cysteine knot superfamily, homolog (Xenopus laevis) | -0.3159 |
| 77 | 211981_at | COL4A1 | collagen, type IV, alpha 1 | -0.4068 |
| 78 | 208960_s_at | KLF6 | Kruppel-like factor 6 | -0.8283 |
| 79 | 212614_at | ARID5B | AT rich interactive domain 5B (MRF1-like) | -0.4958 |
| 80 | 213256_at | 40240 | membrane-associated ring finger (C3HC4) 3 | -0.3128 |
| 81 | 209457_at | DUSP5 | dual specificity phosphatase 5 | -0.3411 |
| 82 | 200695_at | PPP2R1A | protein phosphatase 2 (formerly 2A), regulatory subunit A, alpha isoform | -0.2723 |
| 83 | 209721_s_at | IFFO1 | intermediate filament family orphan 1 | -0.4916 |
| 84 | 32062_at | LRRC14 | leucine rich repeat containing 14 | -0.8628 |
| 85 | 215629_s_at | DLEU2L | deleted in lymphocytic leukemia 2 (non-protein coding) | -0.3601 |
| 86 | 203666_at | CXCL12 | chemokine (C-X-C motif) ligand 12 (stromal cell-derived factor 1) | -0.5935 |
| 87 | 201693_s_at | EGR1 | early growth response 1 | -0.3389 |
| 88 | 219608_s_at | FBXO38 | F-box protein 38 | -0.3463 |
| 89 | 205410_s_at | ATP2B4 | ATPase, Ca++ transporting, plasma membrane 4 | -0.6678 |
| 90 | 212081_x_at | BAT2 | HLA-B associated transcript 2 | -0.3442 |
| 91 | 203820_s_at | IGF2BP3 | insulin-like growth factor 2 mRNA binding protein 3 | -0.2797 |
| 92 | 203525_s_at | APC | adenomatous polyposis coli | -0.4371 |
| 93 | 201278_at | DAB2 | disabled homolog 2, mitogen-responsive phosphoprotein (Drosophila) | -0.3846 |
| 94 | 210879_s_at | RAB11FIP5 | RAB11 family interacting protein 5 (class I) | -0.2738 |
| 95 | 215501_s_at | DUSP10 | dual specificity phosphatase 10 | -0.6162 |
| 96 | 204614_at | SERPINB2 | serpin peptidase inhibitor, clade B (ovalbumin), member 2 | -0.5061 |
| 97 | 202380_s_at | NKTR | natural killer-tumor recognition sequence | -0.4994 |
| 98 | 201279_s_at | DAB2 | disabled homolog 2, mitogen-responsive phosphoprotein (Drosophila) | -0.555 |
| 99 | 213931_at | ID2 | inhibitor of DNA binding 2, dominant negative helix-loop-helix protein | -1.0154 |
| 100 | 211040_x_at | GTSE1 | G-2 and S-phase expressed 1 | -0.6026 |
| 101 | 212073_at | CSNK2A1 | casein kinase 2, alpha 1 polypeptide | -0.3919 |
| 102 | 214682_at | LOC399491 | GPS, PLAT and transmembrane domain-containing protein | -0.6861 |
| 103 | 220606_s_at | C17ORF48 | chromosome 17 open reading frame 48 | -0.3041 |
| 104 | 220738_s_at | RPS6KA6 | ribosomal protein S6 kinase, 90kDa, polypeptide 6 | -0.6137 |
| 105 | 219696_at | DENND1B | DENN/MADD domain containing 1B | -0.4054 |
| 106 | 204004_at | PAWR | PRKC, apoptosis, WT1, regulator | -0.4389 |
| 107 | 215716_s_at | ATP2B1 | ATPase, Ca++ transporting, plasma membrane 1 | -0.482 |
| 108 | 203736_s_at | PPFIBP1 | PTPRF interacting protein, binding protein 1 (liprin beta 1) | -0.3131 |
| 109 | 214668_at | C13ORF1 | chromosome 13 open reading frame 1 | -0.758 |
| 110 | 200965_s_at | ABLIM1 | actin binding LIM protein 1 | -0.5547 |
| 111 | 222033_s_at | FLT1 | fms-related tyrosine kinase 1 (vascular endothelial growth factor/vascular permeability factor receptor) | -0.3405 |
| 112 | 209199_s_at | MEF2C | myocyte enhancer factor 2C | -0.5114 |
| 113 | 215780_s_at | SET | SET translocation (myeloid leukemia-associated) pseudogene | -0.2742 |

FIG. 22D

| A | B | C | D | E |
|---|---|---|---|---|
| 114 | 209427_at | SMTN | smoothelin | -0.4676 |
| 115 | 222034_at | GNB2L1 | Guanine nucleotide binding protein (G protein), beta polypeptide 2-like 1 | -0.3717 |
| 116 | 203642_s_at | COBLL1 | COBL-like 1 | -0.3489 |
| 117 | 210621_s_at | RASA1 | RAS p21 protein activator (GTPase activating protein) 1 | -0.3551 |
| 118 | 204823_at | NAV3 | neuron navigator 3 | -0.5686 |
| 119 | 219627_at | ZNF767 | zinc finger family member 767 | -0.4456 |
| 120 | 205437_at | ZNF211 | zinc finger protein 211 | -0.4734 |
| 121 | 217785_s_at | YKT6 | YKT6 v-SNARE homolog (S. cerevisiae) | -0.2935 |
| 122 | 210376_x_at | ELK1 | ELK1, member of ETS oncogene family | -0.4171 |
| 123 | 208378_x_at | FGF5 | fibroblast growth factor 5 | -0.5821 |
| 124 | 222088_s_at | SLC2A14 | solute carrier family 2 (facilitated glucose transporter), member 14 | -0.4656 |
| 125 | 212289_at | ANKRD12 | ankyrin repeat domain 12 | -0.3521 |
| 126 | 213526_s_at | LIN37 | lin-37 homolog (C. elegans) | -0.3241 |
| 127 | 201280_s_at | DAB2 | disabled homolog 2, mitogen-responsive phosphoprotein (Drosophila) | -0.5309 |
| 128 | 206700_s_at | KDM5D | lysine (K)-specific demethylase 5D | -0.2855 |
| 129 | 204361_s_at | SKAP2 | src kinase associated phosphoprotein 2 | -0.3653 |
| 130 | 202464_s_at | PFKFB3 | 6-phosphofructo-2-kinase/fructose-2,6-biphosphatase 3 | -0.3184 |
| 131 | 214321_at | NOV | nephroblastoma overexpressed gene | -0.3669 |
| 132 | 205991_s_at | PRRX1 | paired related homeobox 1 | -0.3255 |
| 133 | 219431_at | ARHGAP10 | Rho GTPase activating protein 10 | -0.3258 |
| 134 | 200727_s_at | ACTR2 | ARP2 actin-related protein 2 homolog (yeast) | -0.3133 |
| 135 | 214833_at | TMEM63A | transmembrane protein 63A | -0.7906 |
| 136 | 212089_at | LMNA | lamin A/C | -0.2649 |
| 137 | 222263_at | SLC35E1 | solute carrier family 35, member E1 | -0.4369 |
| 138 | 210287_s_at | FLT1 | fms-related tyrosine kinase 1 (vascular endothelial growth factor/vascular permeability factor receptor) | -0.4965 |
| 139 | 206026_s_at | TNFAIP6 | tumor necrosis factor, alpha-induced protein 6 | -0.3322 |
| 140 | 215236_s_at | PICALM | phosphatidylinositol binding clathrin assembly protein | -0.2886 |
| 141 | 212098_at | LOC151162 | hypothetical LOC151162 | -0.3029 |
| 142 | 212218_s_at | FASN | fatty acid synthase | -0.485 |
| 143 | 202080_s_at | TRAK1 | trafficking protein, kinesin binding 1 | -0.373 |
| 144 | 204318_s_at | GTSE1 | G-2 and S-phase expressed 1 | -0.3082 |
| 145 | 213543_at | SGCD | sarcoglycan, delta (35kDa dystrophin-associated glycoprotein) | -0.3622 |
| 146 | 208686_s_at | BRD2 | bromodomain containing 2 | -0.3547 |
| 147 | 219254_at | C17ORF101 | chromosome 17 open reading frame 101 | -0.638 |
| 148 | 222190_s_at | C16ORF58 | chromosome 16 open reading frame 58 | -0.3778 |
| 149 | 213939_s_at | RUFY3 | RUN and FYVE domain containing 3 | -0.5639 |
| 150 | 202948_at | IL1R1 | interleukin 1 receptor, type I | -0.3306 |
| 151 | 222108_at | AMIGO2 | adhesion molecule with Ig-like domain 2 | -0.4444 |
| 152 | 203387_s_at | TBC1D4 | TBC1 domain family, member 4 | -0.3451 |
| 153 | 219635_at | ZNF606 | zinc finger protein 606 | -0.2757 |

FIG. 22E

| A | B | C | D | E |
|---|---|---|---|---|
| 154 | 204720_s_at | DNAJC6 | DnaJ (Hsp40) homolog, subfamily C, member 6 | -0.3729 |
| 155 | 220305_at | MAVS | mitochondrial antiviral signaling protein | -0.3294 |
| 156 | 204506_at | PPP3R1 | protein phosphatase 3 (formerly 2B), regulatory subunit B, alpha isoform | -0.5595 |
| 157 | 218970_s_at | CUTC | cutC copper transporter homolog (E. coli) | -0.2703 |
| 158 | 210311_at | FGF5 | fibroblast growth factor 5 | -0.3899 |
| 159 | 209203_s_at | BICD2 | bicaudal D homolog 2 (Drosophila) | -0.3269 |
| 160 | 209209_s_at | FERMT2 | fermitin family homolog 2 (Drosophila) | -0.3959 |
| 161 | 203242_s_at | PDLIM5 | PDZ and LIM domain 5 | -0.4846 |
| 162 | 206237_s_at | NRG1 | neuregulin 1 | -0.2925 |
| 163 | 221959_at | FAM110B | family with sequence similarity 110, member B | -0.516 |
| 164 | 219563_at | C14ORF139 | chromosome 14 open reading frame 139 | -0.457 |
| 165 | 204190_at | USPL1 | ubiquitin specific peptidase like 1 | -0.2706 |
| 166 | 216933_x_at | APC | adenomatous polyposis coli | -0.7456 |
| 167 | 209946_at | VEGFC | vascular endothelial growth factor C | -0.2915 |
| 168 | 206307_s_at | FOXD1 | forkhead box D1 | -0.505 |
| 169 | 212365_at | MYO1B | myosin IB | -0.3412 |
| 170 | 215177_s_at | ITGA6 | integrin, alpha 6 | -0.3011 |
| 171 | 202342_s_at | TRIM2 | tripartite motif-containing 2 | -0.3317 |
| 172 | 203386_at | TBC1D4 | TBC1 domain family, member 4 | -0.3658 |
| 173 | 213672_at | MARS | methionyl-tRNA synthetase | -0.589 |
| 174 | 204916_at | RAMP1 | receptor (G protein-coupled) activity modifying protein 1 | -0.4961 |
| 175 | 203426_s_at | IGFBP5 | insulin-like growth factor binding protein 5 | -0.321 |
| 176 | 200796_s_at | MCL1 | myeloid cell leukemia sequence 1 (BCL2-related) | -0.3345 |
| 177 | 221841_s_at | KLF4 | Kruppel-like factor 4 (gut) | -0.5958 |
| 178 | 201925_s_at | CD55 | CD55 molecule, decay accelerating factor for complement (Cromer blood group) | -0.3644 |
| 179 | 211862_x_at | CFLAR | CASP8 and FADD-like apoptosis regulator | -0.2666 |
| 180 | 212364_at | MYO1B | myosin IB | -0.2759 |
| 181 | 205798_at | IL7R | interleukin 7 receptor | -0.5215 |
| 182 | 216997_x_at | TLE4 | transducin-like enhancer of split 4 (E(sp1) homolog, Drosophila) | -1.0198 |
| 183 | 204284_at | PPP1R3C | protein phosphatase 1, regulatory (inhibitor) subunit 3C | -0.4681 |
| 184 | 221276_s_at | SYNC | syncoilin, intermediate filament protein | -0.37 |
| 185 | 202674_s_at | LMO7 | LIM domain 7 | -0.5572 |
| 186 | 202647_s_at | NRAS | neuroblastoma RAS viral (v-ras) oncogene homolog | -0.2828 |
| 187 | 218151_x_at | GPR172A | G protein-coupled receptor 172A | -0.375 |
| 188 | 211760_s_at | VAMP4 | vesicle-associated membrane protein 4 | -0.4264 |
| 189 | 209287_s_at | CDC42EP3 | CDC42 effector protein (Rho GTPase binding) 3 | -0.2793 |
| 190 | 219923_at | TRIM45 | tripartite motif-containing 45 | -0.7815 |
| 191 | 207233_s_at | MITF | microphthalmia-associated transcription factor | -0.4299 |
| 192 | 220123_at | SLC35F5 | solute carrier family 35, member F5 | -0.577 |
| 193 | 203128_at | SPTLC2 | serine palmitoyltransferase, long chain base subunit 2 | -0.4163 |
| 194 | 214237_x_at | PAWR | PRKC, apoptosis, WT1, regulator | -0.527 |

FIG. 22F

| A | B | C | D | E |
|---|---|---|---|---|
| 195 | 219114_at | C3ORF18 | chromosome 3 open reading frame 18 | -0.5087 |
| 196 | 221657_s_at | ASB6 | ankyrin repeat and SOCS box-containing 6 | -0.4143 |
| 197 | 201604_s_at | PPP1R12A | protein phosphatase 1, regulatory (inhibitor) subunit 12A | -0.3374 |
| 198 | 211828_s_at | TNIK | TRAF2 and NCK interacting kinase | -0.5138 |
| 199 | 202432_at | PPP3CB | protein phosphatase 3 (formerly 2B), catalytic subunit, beta isoform | -0.3304 |
| 200 | 209655_s_at | TMEM47 | transmembrane protein 47 | -0.3293 |

FIG. 23

Table Q: Average CMap scores for some representative potential skin-lightening agents with the Retinoic Acid Keratinocyte RA_200 Signature

| Chemical | Cell Line | Concentration | Average CMap score |
|---|---|---|---|
| All-trans retinoic acid | tKC | 1 uM | 1.804 |
| Myo-inositol | tKC | 20 uM | 1.128 |
| Hexyldecanol | tKC | 0.10% | 0.611 |
| Chlorhexidine | tKC | 10 uM | 0.54 |

FIG. 24A

Table R:
Comparison of the predictiveness of different C-map signatures for predicting the activity of compounds in the mouse B16 melanoma cell melanogenesis assay

|  |  | Average C-map Score | | | | |
|---|---|---|---|---|---|---|
| Chemical | Type | Composite | Hexamidine | NAG | Niacinamide | Sepiwhite |
| Sepiwhite MSH | Benchmark | 1.26 | | | | 0.95 |
| Nicotinamide | Benchmark | 1.17 | | | 0.75 | |
| Hexamidine diisethionate | Benchmark | 0.93 | 0.32 | | | |
| N-acetyl-D-glucosamine | Benchmark | 0.69 | | 0.96 | | |
| Emodin | Inhibitor | 0.97 | | | | |
| chlorhexidine diacetate | Inhibitor | 0.9 | | | | 0.33 |
| Usnic Acid | Inhibitor | 0.9 | | | | |
| resveratrol | Inhibitor | 0.88 | | | | 0.32 |
| Tyrphostin AG 879 | Inhibitor | 0.88 | | | | 0.63 |
| Nordihydroguaiaretic acid from Larrea divaricata (creosote bush) | Inhibitor | 0.87 | | | | 0.75 |
| Tergitol NP 10 | Inhibitor | 0.87 | | | | 0.57 |
| 3,4,4'-Trichlorocarbanilide | Inhibitor | 0.86 | | | | |
| U-75302 | Inhibitor | 0.81 | 0.55 | | | 0.65 |
| AA-861 | Inhibitor | 0.8 | | | | 0.53 |
| Boswellin CG | Inhibitor | 0.76 | | | | |
| Ricinoleic acid | Inhibitor | 0.76 | | | | |
| Nw-Nitro-L-arginine methyl ester HCl | Inhibitor | 0.69 | | | | |
| SB 218795 | Inhibitor | 0.62 | | | | |
| chlorhexidine | Inhibitor | 0.45 | | | | 0.43 |
| Tetrahydrocurcumin CG | Inhibitor | 0.44 | | | | |
| HYDROQUINONE | Inhibitor | | | | | |
| 6-Hydroxy-1,3-benzoxathiol-2-one | Inhibitor | | | | | |
| 6-HYDROXYINDOLE | Inhibitor | | | | | |
| Acetyl tributyl citrate | Inhibitor | | | | | |
| Berberine Chloride | Inhibitor | | | | | |
| Brij 98 | Inhibitor | | | | | |
| Copper(II) D-gluconate | Inhibitor | | | | | |
| Oleyl alcohol | Inhibitor | | | | | |
| Piroctone olamine | Inhibitor | | | | | |
| Pluronic L101 | Inhibitor | | | | | |
| Tannic acid | Inhibitor | | | | | |
| tert-BUTYL HYDROQUINONE | Inhibitor | | | | | |
| kynurenic acid | Inhibitor | | | | | |

FIG. 24B

| Total Inhibitors and benchmarks identified | 20 | 2 | 1 | 1 | 9 |
|---|---|---|---|---|---|
| Note: no C-map score means that the chemical was not a hit (i.e., in the top 200 instances of the corresponding signature with a score >=0.30). | | | | | |

FIG. 25

Table S:

| Skin Tone Benchmark Materials | Concentration | Number of probe sets with significant (<0.05) p-values compared to DMSO controls | | |
|---|---|---|---|---|
| | | Tert-keratinocytes | HBL melanoma cells | HeMnMP melanocytes |
| Hexamidine diisethionate | 5 uM | 4263 | 1497 | 2359 |
| Myo-inositol | 20 uM | 5082 | 960 | 3687 |
| N-acetyl-glucosamine | 200 uM | 1034 | 1334 | 1454 |
| NDP-MSH* | 100 nM | 1448 | 1532 | 1173 |
| Niacinamide | 100 uM | 2198 | 1345 | 1312 |
| Sepiwhite | 10 uM | 2451 | 883 | 2310 |

METHOD OF GENERATING A HYPERPIGMENTATION CONDITION GENE EXPRESSION SIGNATURE

BACKGROUND OF THE INVENTION

Skin pigment irregularities are common across ethnic and racial groups and are often considered cosmetically disfiguring. Disorders of pigment production and distribution occur as a function of intensity and duration of UV radiation exposure, life style habits, chronological age, endocrine functioning and disease state and are found ubiquitously in older populations. Hence there is a widespread demand for skin pigment modifying, skin lightening and skin tone enhancing products for the cosmetic market.

The color of normal human skin is due primarily to varying amounts and distribution of melanin, hemoglobin, and carotenoids. Of these pigments, melanin is of primary significance to cosmetic skin treatment protocols. Melanin is produced by specialized cells in the skin called melanocytes through a complicated series of chemical and enzymatic reactions, mainly involving the copper and manganese containing enzyme tyrosinase. Once synthesized, the melanin granules are packaged into melanosomes and transferred via the cellular dendrites (extensions) of the melanocyte to the surrounding keratinocytes, the most abundant cell type in the epidermis. The rate of melanin synthesis, and the subsequent transfer of melanin by melanocytes via their dendrites, appears to be influenced by ultraviolet light exposure. Melanosomes transferred to the outer layer of the skin are responsible for the darkening of the skin, with the degree of darkening being associated with skin type, sun exposure, and/or certain dermatological conditions.

Two types of melanin are present in human skin: (1) eumelanin, which is the dark brown-black pigment found in most skin, hair, and eyes, and whose production is stimulated by exposure to ultraviolet light, and (2) pheomelanin, which is a yellow-orange pigment found mainly in the skin of very fair-skinned people, particularly those with red hair. The perceived color of skin is determined by the ratio of eumelanins to pheomelanins, and to a smaller extent on blood within the dermis.

The pigmentation pathway has been elucidated in detail. Summarily, melanin forms through a series of oxidative reactions involving the amino acid tyrosine in the presence of the enzyme tyrosinase. Tyrosinase converts tyrosine to dihydroxyphenylalanine (DOPA) and then to dopaquinone. Subsequently, dopaquinone is converted to dopachrome through auto-oxidation, and finally to dihydroxyindole or dihydroxyindole-2-carboxylic acid (DHICA), which polymerize to form eumelanin. The latter reactions occur in the presence of dopachrome tautomerase and DHICA oxidase. In the presence of sulfur-containing cysteine or glutathione, dopaquinone is converted to cysteinyl DOPA or glutathione DOPA; subsequently, pheomelanin is formed.

A variety of skin hyperpigmentation disorders are known and etiology is diverse, overlapping in many cases, and often not fully understood. For example, melanosis or melasma is a condition characterized by the development of sharply demarcated blotchy, brown spots usually in a symmetric distribution over the cheeks, forehead, and sometimes on the upper lip and neck. This condition frequently occurs during pregnancy (melasma gravidarum or "mask of pregnancy"), and at menopause. Also, this condition is frequently found among those taking oral contraceptives, and is occasionally found among nonpregnant women who are not taking oral contraceptives, and sometimes among men. A pattern of similar facial hyperpigmentation is associated with a chronic liver disease called chloasma. A common condition associated with aging skin is the development of dark spots sometimes referred to as "age spots" or "liver spots." Other forms of hyperpigmentation can be caused by UV irradiation, in particular UVB radiation which up-regulates the production of tyrosinase resulting in skin "tanning," or may result from a genetic predisposition for the condition, or may come about in association with a skin inflammatory event or during the course of wound healing.

Vitiligo is a form of hypopigmentation in which cutaneous melanocytes are either ablated or fail to produce sufficient pigment. Ideally treatment would restore lost pigmentation in vitiligo-affected skin, but this approach has met with little success via topical interventions and formulations. Although cosmetic camouflage with dihydroxyacetone sunless-tanning lotions provides some darkening of hypo-pigmented areas, it also tends to darken surrounding normal skin, substantially maintaining the undesirable contrast. Hence, a more favored cosmetic approach is to reduce the normal pigmentation of the unaffected skin to reduce contrast and produce a tone evening effect.

Several proven targets for pigmentation control are known, but these have generally been derived from an understanding of the pigmentation process. Hydroquinone (parahydroxy-benzene), for example, is a widely used skin lightening agent that is known to provide a satisfactory cosmetic result, however its use strictly for cosmetic purposes is discouraged due to its association with a variety of disorders, including diabetes, hypertension, ochronosis, periorbitary dyschromia, infectious dermatosis, contact eczema, extended dermatophytosis, and necrotizing cellulites (see, e.g., Raynaud E. et al., Ann Dermatol Venereol 128(6-7):720-724, 2001). Hydroquinone has also shown genotoxic and mutagenic activities (see, e.g., Jagetia G. C. et al, Toxicol Lett 121(1):15-20, 2001). Due to concerns over toxicity and carcinogenic effects, the United States limits treatment solutions to a 2% or lower concentration and the FDA has proposed a ban on all over-the-counter preparations, while hydroquinone is currently banned in Europe as a skin lightening or depigmenting agent.

Kojic acid, Azelaic acid and certain-hydroxy acids such as glycolic acid, have demonstrated skin-lightening effects, but reports of localized irritation and inflammation are common. The prenylated flavonol artocarpin has shown some efficacy for skin-lightening in the context of ultraviolet-induced skin pigmentation (Shimizu K. et al., Planta Med 68(1):79-81, 2002).

Recently, a more detailed genomic and proteomic understanding of melanogenesis, the melanocyte, melanocyte-keratinocyte interaction, and the melanocyte-fibroblast interaction has revealed potentially hundreds of proteins and other effectors involved in the pigmentation process and in the etiology of hyperpigmentation disorders, which may provide additional targets. There is a need in the cosmetic arts both for generating potential skin lightening agents and for effective and efficient screening methods for identifying putative skin active agents with efficacy and safety in the cosmetic treatment of hyperpigmentation and pigmentation disorders.

Traditionally scientists have focused on the development and provision of safe and effective topical compositions formulated to lighten skin and such an approach has been useful for treating localized epidermal hyperpigmentation and for masking areas of skin hypopigmentation. There remains a need, however, for safe and effective agents capable of delivery through topical application to reduce the degree of skin pigmentation in both contexts.

Skin pigmentation and the broader cosmetic concept of skin tone, are therefore highly complex conditions with multiple and overlapping etiologies, which manifest in part as a function of individual predisposition, and which therefore pose a significant treatment challenge. There is a need in the art for methods of identifying potential skin pigment modifying agents, and in particular skin-lightening agents, and for evaluating the efficacy of putative skin active agents using screening methods that are substantially independent of mechanism of action or etiology of the pigment condition. The present investigators therefore undertook an investigation into the application of a relatively new technology known as "connectivity mapping" to the search for new skin-active agents with efficacy in the treatment of hyperpigmentation disorders and related skin conditions.

Connectivity mapping is a well-known hypothesis generating and testing tool having successful application in the fields of operations research, telecommunications, and more recently in pharmaceutical drug discovery. The undertaking and completion of the Human Genome Project, and the parallel development of very high throughput high-density DNA microarray technologies enabling rapid and simultaneous quantization of cellular mRNA expression levels, resulted in the generation of an enormous genetic database. At the same time, the search for new pharmaceutical actives via in silico methods such as molecular modeling and docking studies stimulated the generation of vast libraries of potential small molecule actives. The amount of information linking disease to genetic profile, genetic profile to drugs, and disease to drugs grew exponentially, and application of connectivity mapping as a hypothesis testing tool in the medicinal sciences ripened.

The general notion that functionality could be accurately determined for previously uncharacterized genes, and that potential targets of drug agents could be identified by mapping connections in a data base of gene expression profiles for drug-treated cells, was spearheaded in 2000 with publication of a seminal paper by T. R. Hughes et al. ["Functional discovery via a compendium of expression profiles" *Cell* 102, 109-126 (2000)], followed shortly thereafter with the launch of The Connectivity Map (-map Project by Justin Lamb and researchers at MIT ("Connectivity Map: Gene Expression Signatures to Connect Small Molecules, Genes, and Disease", *Science, Vol* 313, 2006.) In 2006, Lamb's group began publishing a detailed synopsis of the mechanics of C-map construction and installments of the reference collection of gene expression profiles used to create the first generation C-map and the initiation of an on-going large scale community C-map project, which is available under the "supporting materials" hyperlink at http://www.sciencemag.org/content/313/5795/1929/suppl/DC1.

The basic paradigm of predicting novel relationships between disease, disease phenotype, and drugs employed to modify the disease phenotype, by comparison to known relationships has been practiced for centuries as an intuitive science by medical clinicians. Modern connectivity mapping, with its rigorous mathematical underpinnings and aided by modern computational power, has resulted in confirmed medical successes with identification of new agents for the treatment of various diseases including cancer. Nonetheless, certain limiting presumptions challenge application of C-map with respect to diseases of polygenic origin or syndromic conditions characterized by diverse and often apparently unrelated cellular phenotypic manifestations.

According to Lamb, the challenge to constructing a useful C-map is in the selection of input reference data which permit generation of clinically salient and useful output upon query. For the drug-related C-map of Lamb, strong associations comprise the reference associations, and strong associations are the desired output identified as hits.

Noting the benefit of high-throughput, high density profiling platforms which permit automated amplification, labeling hybridization and scanning of 96 samples in parallel a day, Lamb nonetheless cautioned: "[e]ven this much firepower is insufficient to enable the analysis of every one of the estimated 200 different cell types exposed to every known perturbagen at every possible concentration for every possible duration . . . compromises are therefore required" (page 54, column 3, last paragraph). Lamb, however, took the position that cell type did not ultimately matter, and confined his C-map to data from a very small number of established cell lines out of efficiency and standardization concerns. Theoretically this leads to heightened potential for in vitro to in vivo mismatch, and limits output information to the context of a particular cell line. If one accepts the Lamb precept that cell line does not matter then this limitation may be benign.

However, agents suitable as pharmaceutical agents and agents suitable as cosmetic agents are categorically distinct, with the former defining agents selected for specificity and which are intended to have measurable effects on structure and function of the body, while the latter are selected for effect on appearance and may not affect structure and function of the body to a measurable degree. Cosmetic agents tend to be substantially non-specific with respect to effect on cellular phenotype, and administration to the body is generally limited to application on or close to the body surface.

In constructing C-maps relating to pharmaceutical agents, Lamb stresses that particular difficulty may be encountered if reference connections are extremely sensitive and at the same time difficult to detect (weak), and Lamb adopted compromises aimed at minimizing numerous, diffuse associations. Since the regulatory scheme for drug products requires high degrees of specificity between a purported drug agent and disease state, and modulation of disease by impacting a single protein with a minimum of tangential associations is desired in development of pharmaceutical actives, the Lamb C-map is well-suited for screening for potential pharmaceutical agents despite the Lamb compromises.

The connectivity mapping protocols of Lamb would not be predicted, however, to have utility for hypothesis testing/generating in the field of cosmetics or for a primarily cosmetic disorder where symptoms may be diffuse, systemic and relatively mild. In complete contravention of the goal of pharmaceutical active discovery, cosmetic formulators seek agents or compositions of agents capable of modulating multiple targets and having effects across complex phenotypes and conditions. Further, the phenotypic impact of a cosmetic agent must be relatively low by definition, so that the agent avoids being subject to the regulatory scheme for pharmaceutical actives. Nonetheless, the impact must be perceptible to the consumer and preferably empirically confirmable by scientific methods. Gene transcription/expression profiles for cosmetic conditions are generally diffuse, comprising many genes with low to moderate fold differentials. Cosmetic agents, therefore, provide more diverse and less acute effects on cellular phenotype and generate the sort of associations expressly taught by Lamb as unsuitable for generating connectivity maps useful for confident hypothesis testing.

Successful identification of skin lightening agents has proven to be difficult due to the multi-cellular, multi-factorial processes involved in etiology of the hyperpigmentation condition itself. Conventional in vitro studies of biological responses to potential skin-lightening agents can be hindered by the complex or weakly detectable responses typically induced and/or caused by the putative skin active or potential skin active agents. Such weak responses arise, in part, due to the great number of genes and gene products involved, and the fact that skin-active and cosmetic agents may affect multiple genes in multiple ways. Moreover, the degree of bioactivity of cosmetic agents may differ for each gene and be difficult to quantify.

The value of a connectivity map approach to discover functional connections among cosmetic phenotypes such as hyperpigmented skin, gene expression perturbation, and cosmetic agent action is counter-indicated by the progenors of the drug-based C-map. The relevant phenotypes are very complex, the genetic perturbations are numerous and weak, and cosmetic agent action is likewise diffuse and by definition, relatively weak. It is unclear whether statistically valid data may be generated from cosmetic C-maps and it is further unclear whether a cell line exists which may provide salient or detectable cosmetic data.

SUMMARY OF THE INVENTION

Accordingly, the present inventors have developed a C-map approach that surprisingly enables discovery of skin tone agents having efficacy for disorders of skin pigmentation.

The present inventors discovered that useful connectivity maps could be developed from cosmetic active—cellular phenotype—gene expression data associations in particular with respect to hyperpigmentation actives and cosmetic agents, despite the highly diffuse, systemic and low-level effects these sorts of actives generally engender. Although the Lamb team asserted that results should be substantially independent of cell-type, the present inventors surprisingly discovered that selection of cell line affects the utility of the C-map for hypothesis generating and testing relating to skin pigmentation actives and treatment of hyperpigmentation disorders. In particular, keratinocyte cells, rather than melanocyte or melanoma cells, exhibited a more robust transcriptional profile when treated with skin-lightening agents, and there was little to no thematic overlap between cell types treated with the same benchmark skin active agent (shown in Example 8).

Accordingly, the present invention provides novel methods, systems and models useful for generating potential new skin-active agents efficacious for the treatment of skin conditions such as hyperpigmentation. Through careful selection of cell type, and by generation of a reference collection of gene-expression profiles for known skin-active agents and recognized skin disorders, the present inventors were surprisingly able to create connectivity map architecture useful for testing and generating hypotheses about skin-active agents and hyperpigmentation skin disorders.

The present invention provides embodiments which broadly include methods and systems for determining relationships between a skin condition/disorder of interest and one or more skin-active agents, one or more genes associated with the skin disorder condition, and physiological themes implicated by the skin condition and/or affected by a skin-active agent. The inventive methods may be used to identify skin-active agents without detailed knowledge of the mechanisms of biological processes associated with a skin disorder or condition of interest, all of the genes associated with such a condition, or the cell types associated with such a condition.

One aspect of the invention provides methods for constructing a data architecture for use in identifying connections between perturbagens and genes associated with skin tone, comprising: (a) providing a gene expression profile for a control human cell, wherein the control cell is from a human cell line selected from the group consisting of keratinocyte, fibroblast, melanocyte and melanoma cell lines; (b) generating a gene expression profile for a human cell exposed to at least one perturbagen, wherein the cell is selected from the same cell line as the control cell; (c) identifying genes differentially expressed in response to the at least one perturbagen by comparing the gene expression profiles of (a) and (b); (d) creating an ordered list comprising identifiers representing the differentially expressed genes, wherein the identifiers are ordered according to the differential expression of the genes; (e) storing the ordered list as an instance on at least one computer readable medium, wherein the instance is a keratinocyte, fibroblast melanocyte or melanoma instance according to the selection in (a); and (f) constructing a data architecture of stored instances by repeating (a) through (e), wherein the at least one perturbagen of step (a) is different qualitatively or quantitatively for each instance. In specific embodiments each instance is repeated twice in C-map testing. Example 4 illustrates generating a benchmark skin tone agent signature using fibroblasts to create signatures and using keratinocytes to create signatures.

The data architecture may be mined to identify relationships between perturbagens, genotypes and phenotypes and may also be used as an in silico tool for generating new actives with potential efficacy for treatment of a cosmetic condition. The data architecture may be implemented for this purpose through the use of a query, which is an input to the C-map wherein the output is based on connectivity scores to the query. In one embodiment, a method for implementing the data architecture to identify at least one putative skin active agent having potential efficacy in treating a skin pigmentation condition is provided. The method comprises querying the data architecture with a pigmentation-relevant gene expression signature, wherein querying comprises comparing the pigmentation-relevant gene expression signature to each stored cell instance, and further wherein the pigmentation-relevant expression signature represents genes differentially expressed in cells derived from skin affected with a skin hyperpigmentation condition or genes differentially expressed in cells treated with at least one benchmark skin active agent having known efficacy in treating a skin hyperpigmentation condition. Cell instances are derived from a keratinocyte, fibroblast, melanocyte or melanoma cell line and the pigmentation-relevant gene expression signature is derived from a corresponding cell line. Example 1 illustrates development of a hyperpigmentation condition expression signature.

Other embodiments are direct to methods for generating a hyperpigmentation condition gene expression signature for use in identifying connections between perturbagens and genes associated with a skin pigmentation condition. Methods comprise: (a) providing a gene expression profile for a reference sample of human skin cells not affected with a pigmentation condition; (b) generating a gene expression profile for at least one sample of human skin cells from a subject exhibiting the hyperpigmentation condition, (c) comparing the expression profiles of (a) and (b) to determine a gene expression signature comprising a set of genes differentially expressed in (a) and (b); (d) assigning an identifier to each gene constituting the gene expression signature and ordering the identifiers according to the direction of differential expression to create one or more gene expression signature lists; and (e) storing the one or more gene expression signature lists on at least one computer readable medium.

Another embodiment provides methods for generating a benchmark skin pigmentation-modifying gene expression signature for use in identifying connections between perturbagens and genes associated with a skin pigmentation condition, the method comprising: (a) generating a gene expression profile for a human skin cell sample treated with at least one benchmark skin pigmentation modifying agent, wherein the benchmark skin pigmentation modifying agent is suspended in a vehicle composition, (b) generating a gene expression profile for a human skin cell sample treated with the vehicle composition; (c) comparing the expression profiles of (a) and (b) to determine a gene expression signature comprising a set of genes differentially expressed in (a) and (b); (d) assigning an identifier to each gene constituting the gene expression signature and ordering the identifiers according to the direction of differential expression to create one or more gene expression signature lists; and (e) storing the one or more gene expression signature lists on at least one computer readable medium. Gene expression signatures and immobilized arrays of probes corresponding to the genes constituting the inventive signatures are also provided.

In some aspects a single benchmark skin active agent may be used to generate a benchmark signature (see Example 2) and in other aspects a composite signature may be generated by treating a cell sample with more than one agent (see Examples 3, 6, and 7). A composite signature can be added in two ways: cells can be treated with each agent separately, the signature can be generated by comparing regulated genes from all agents (together), looking for genes regulated in the same direction by all agents; secondarily, agents can be mixed together prior to treatment of cells. In another embodiment, a composite benchmark signature may be generated for a skin-lightening agent (Example 2), and another generated for a skin darkening agent. The signature for the skin-lightening agent may be further tweaked by eliminating any gene from the signature that also appears in the signature of the skin-darkening agent, regulated in the same direction, or vice versa. The inventors discovered that such composite signatures are particularly useful for mining C-map for agents capable of modifying skin pigment in the desired direction.

Systems for identifying connections between perturbagens and genes associated with a skin hyperpigmentation condition are also provided. The systems comprise: (a) at least one computer readable medium having stored thereon a plurality of instances, and a skin hyperpigmentation-relevant gene expression signature, wherein the instances and the gene expression signature are derived from one of a human keratinocyte cell, a human fibroblast cell, a human melanocyte cell, or a human melanoma cell, wherein each instance comprises an instance list of rank-ordered identifiers of differentially expressed genes, and wherein the hyperpigmentation-relevant gene expression signature comprises one or more gene expression signature lists of identifiers representing differentially expressed genes associated with a hyperpigmentation condition or differentially expressed genes associated with a benchmark skin-lightening agent; (b) a programmable computer comprising computer-readable instructions that cause the programmable computer to execute one or more of the following: (i) accessing the plurality of instances and a hyperpigmentation-relevant gene expression signature stored on the computer readable medium; (ii) comparing the hyperpigmentation-relevant gene expression signature to the plurality of the instances, wherein the comparison comprises comparing each identifier in the gene expression signature list with the position of the same identifier in the instance list for each of the plurality of instances; and (iii) assigning a connectivity score to each of the plurality of instances.

A computer readable medium aspect is also disclosed wherein a data architecture comprising a first digital file is stored in a spreadsheet file format, a word processing file format, or a database file format suitable to be read by a respective spreadsheet, word processing, or database computer program, the first digital file comprising data arranged to provide one or more gene expression signature lists comprising a plurality of identifiers when read by the respective spreadsheet, word processing, or database computer program; and wherein each identifier is selected from the group consisting of a microarray probe set ID, a human gene name, a human gene symbol, and combinations thereof representing a gene set forth in any of Tables B through P wherein each of the one or more gene expression signature lists comprises between about 10 and about 400 identifiers. Instructions for reading the digital file may be included.

These and additional objects, embodiments, and aspects of the invention will become apparent by reference to the Figures and Detailed Description below.

BRIEF DESCRIPTION OF THE FIGURES

FIG. 1 sets forth pigmentation control targets and some benchmark skin active agents as depicted in Table A.

FIG. 2 sets forth identifiers for the genes constituting a gene expression signature for hyperpigmented skin. Table B sets forth identifiers for the 200 most significantly up-regulated genes and Table C sets forth identifiers for the 200 most significantly down-regulated genes.

FIG. 10 sets forth identifiers as shown in Table D, Hexamidine Benchmark Signature; 100 up-regulated.

FIG. 11 sets forth identifiers as shown in Table E, Hexamidine Benchmark Signature; 100 top down-regulated.

FIG. 12 sets forth identifiers as shown in Table F, NAG Benchmark Signature; 39 significantly up-regulated.

FIG. 13 sets forth identifiers as shown in Table G, NAG Benchmark Signature, most significantly down-regulated.

FIG. 14 sets forth identifiers as shown in Table H, Niacinamide Benchmark Signature, 100 top up-regulated.

FIG. 15 sets forth identifiers as shown in Table I, Niacinamide Benchmark Signature, 100 top down-regulated.

FIG. 16 sets forth identifiers as shown in Table J, Sepiwhite Benchmark Signature; 100 top up-regulated.

FIG. 17 sets forth identifiers as shown in Table K, Sepiwhite Benchmark Signature; 100 top down-regulated.

FIG. 18 sets forth identifiers as shown in Table L, Composite "Skin Tone" Benchmark Signature; approximately 40 up-regulated+58 down-regulated.

FIG. 19 sets forth identifiers as shown in Table M, RA benchmark signature in tKC cell–200 upregulated.

FIG. 20 sets forth identifiers as shown in Table N, RA benchmark signature in tKC, 200 down-regulated.

FIG. 21 sets forth identifiers as shown in Table O, RA Benchmark Signature in BJ fibroblasts, 200 up-regulated.

FIG. 22 sets forth identifiers as shown in Table P, RA Benchmark Signature in BJ fibroblast, 200 down-regulated.

FIG. 23 sets in Table Q, Average C-map scores for some representative potential skin lightening agents with the Retinoic Acid Keratinocyte RA_200 Signature.

FIG. 24 Shows Table R, showing a comparison of the predictiveness of different C-map signatures for predicting the activity of compounds in the mouse B16 melanoma cell melanogenesis assay.

FIG. 25, Shows Table S, with data outlining the responsiveness of tert Keratinocytes, melanocytes, and melanoma cells to skin tone benchmarks.

DETAILED DESCRIPTION OF THE INVENTION

Figure 3:
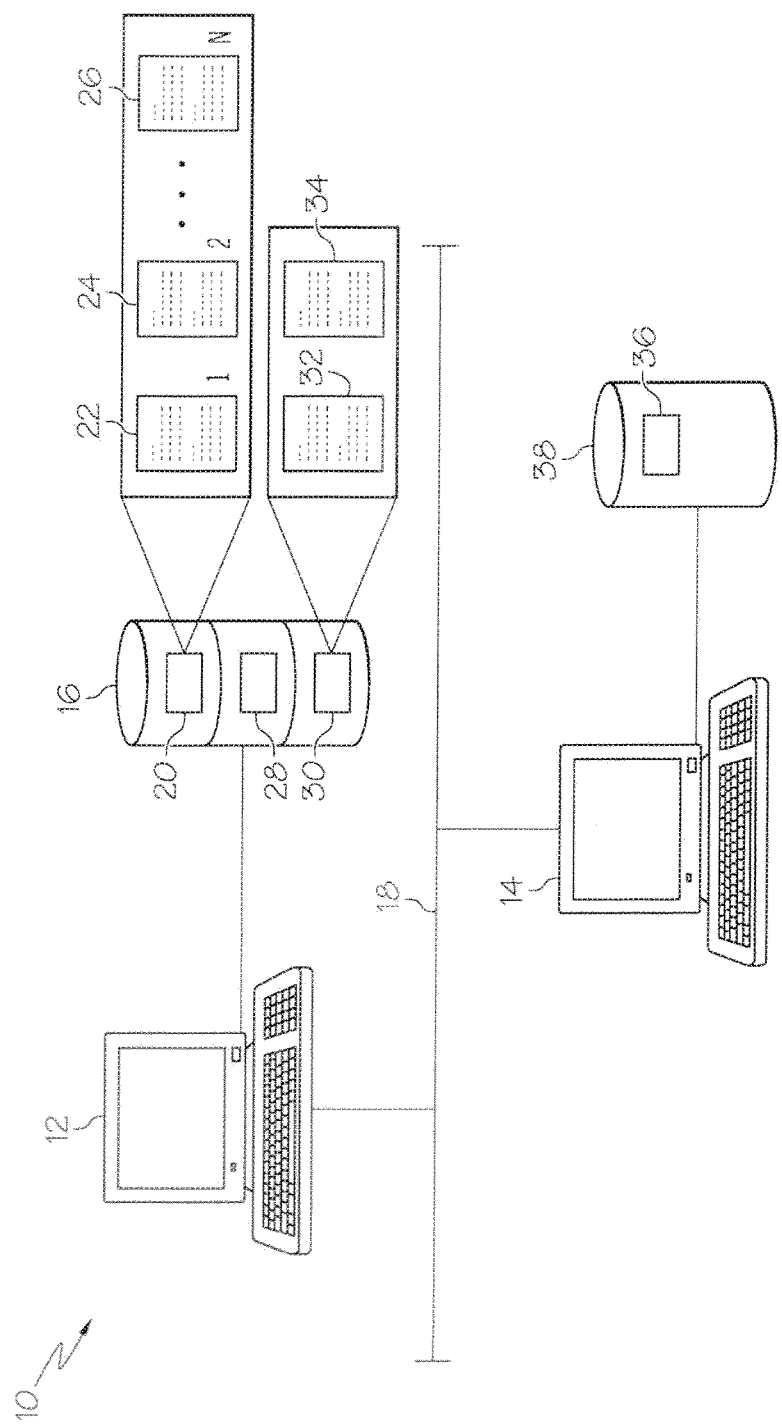
FIG. 3 is a schematic illustration of a computer system suitable for use with the present invention.

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and to fully convey the scope of the invention to those skilled in the art.

Unless otherwise defined, all technical and scientific terms used herein have the same meaning as commonly understood by one of ordinary skill in the art to which this invention pertains. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

As used interchangeably herein, the terms "connectivity map" and "C-map" refer broadly to devices, systems, articles of manufacture, and methodologies for identifying relationships between cellular phenotypes or cosmetic conditions, gene expression, and perturbagens, such as cosmetic actives.

As used herein, the term "cosmetic agent" means any substance, as well as any component thereof, which may be rubbed, poured, sprinkled, sprayed, introduced into, or otherwise applied to a mammalian body or any part thereof. Cosmetic agents may include substances that are Generally Recognized as Safe (GRAS) by the US Food and Drug Administration, food additives, and materials used in non-cosmetic consumer products including over-the-counter medications. In some embodiments, cosmetic agents may be incorporated in a cosmetic composition comprising a dermatologically acceptable carrier suitable for topical application to skin. A cosmetic agent includes, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are known to induce or cause at least one effect (positive or negative) on skin tissue and are discovered, using the provided methods and systems, to induce or cause at least one previously unknown effect (positive or negative) on the skin tissue; and (iii) chemicals, compounds, small molecules, extracts, formulations, or combinations thereof that are not known have an effect on skin tissue and are discovered, using the provided methods and systems, to induce or cause an effect on skin tissue.

Some examples of cosmetic agents or cosmetically actionable materials can be found in: the PubChem database associated with the National Institutes of Health, USA (http://pubchem.ncbi.nlm.nih.gov); the Ingredient Database of the Personal Care Products Council (http://online.personalcarecouncil.org/jsp/Home.jsp); and the 2010 International Cosmetic Ingredient Dictionary and Handbook, 13$^{th}$ Edition, published by The Personal Care Products Council; the EU Cosmetic Ingredients and Substances list; the Japan Cosmetic Ingredients List; the Personal Care Products Council, the SkinDeep database (URL: http://www.cosmeticsdatabase.com); the FDA Approved Excipients List; the FDA OTC List; the Japan Quasi Drug List; the US FDA Everything Added to Food database; EU Food Additive list; Japan Existing Food Additives, Flavor GRAS list; US FDA Select Committee on GRAS Substances; US Household Products Database; the Global New Products Database (GNPD) Personal Care, Health Care, Food/Drink/Pet and Household database (URL: http://www.gnpd.com); and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panethenol, ascorbic acid, tocopherol, and tocopherol acetate). Other non-limiting examples of cosmetic agents include sugar amines, phytosterols, hexamidine, hydroxy acids, ceramides, amino acids, and polyols.

Non-limiting examples of agents herein utilized are described in detail below, such as for vitamin B3 compounds, N-acyl amino acid compounds, and retinoid compounds. In some embodiments, the vitamin B compound is a B3 compound having the formula:

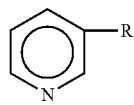

wherein R is —CONH$_2$ (i.e., niacinamide), —COOH (i.e., nicotinic acid) or —CH$_2$OH (i.e., nicotinyl alcohol); derivatives thereof; and salts of any of the foregoing. Exemplary derivatives include nicotinic acid esters, including non-vasodilating esters of nicotinic acid (e.g., tocopheryl nicotinate, myristyl nicotinate). Examples of suitable vitamin $B_3$ compounds are well known in the art and are commercially available from a number of sources (e.g., the Sigma Chemical Company, ICN Biomedicals, Inc., and Aldrich Chemical Company).

Some embodiments of the compositions of the present invention comprise a safe and effective amount of one or more N-acyl amino acid compounds. The amino acid can be one of any of the amino acids known in the art. The N-acyl amino acid compounds of the present invention correspond to the formula:

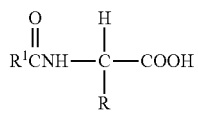

wherein R can be a hydrogen, alkyl (substituted or unsubstituted, branched or straight chain), or a combination of alkyl and aromatic groups. A list of possible side chains of amino acids known in the art are described in Stryer, *Biochemistry*, 1981, published by W.H. Freeman and Company. $R^1$ can be $C_1$ to $C_{30}$, saturated or unsaturated, straight or branched, substituted or unsubstituted alkyls; substituted or unsubstituted aromatic groups; or mixtures thereof.

Preferably, the N-acyl amino acid compound is selected from the group consisting of N-acyl Phenylalanine, N-acyl Tyrosine, their isomers, their salts, and derivatives thereof. The amino acid can be the D or L isomer or a mixture thereof. N-acyl Phenylalanine corresponds to the following formula:

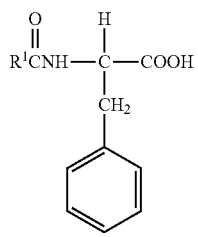

wherein $R^1$ can be $C_1$ to $C_{30}$, saturated or unsaturated, straight or branched, substituted or unsubstituted alkyls; substituted or unsubstituted aromatic groups; or mixtures thereof.

N-acyl Tyrosine corresponds to the following formula:

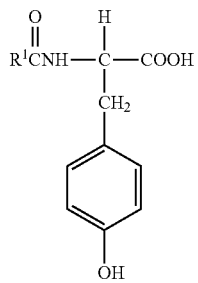

wherein $R^1$ can be $C_1$ to $C_{30}$, saturated or unsaturated, straight or branched, substituted or unsubstituted alkyls; substituted or unsubstituted aromatic groups; or mixtures thereof.

A particularly useful compound in the present invention is N-undecylenoyl-L-phenylalanine. This agent belongs to the broad class of N-acyl Phenylalanine derivatives, with its acyl group being a C11 mono-unsaturated fatty acid moiety and the amino acid being the L-isomer of phenylalanine. N-undecylenoyl-L-phenylalanine corresponds to the following formula:

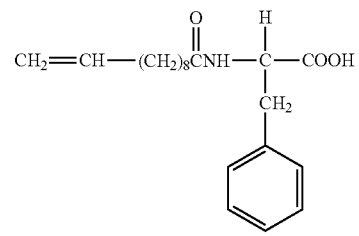

As used herein, N-undecylenoyl-L-phenylalanine is commercially available under the tradename Sepiwhite® from SEPPIC, France.

Some embodiments of the present invention include retinoid compounds. As used herein, "Retinoid Compounds" include all natural and/or synthetic analogs of Vitamin A or retinol-like compounds which possess the biological activity of Vitamin A in the skin as well as the geometric isomers and stereoisomers of these compounds. The Retinoid Compound includes, but is not limited to, retinol, retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid). In some embodiments, the Retinoid Compound is retinoic acid. These compounds are well known in the art and are commercially available from a number of sources, e.g., Sigma Chemical Company (St. Louis, Mo.), and Boerhinger Mannheim (Indianapolis, Ind.). Other Retinoid Compounds which may be useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and Reissue 34,075, issued Sep. 22, 1992 to Purcell et al.

As used herein, the term "putative skin active agent" means a cosmetic agent as herein defined that has shown promise through preliminary screens as effecting a specific change in skin biology related to pigmentation but that has not yet been tested for effectiveness through the methods herein described for constructing a data architecture for use in identifying connections between perturbagens and genes associated with skin tone, comprising As used herein, the term "skin-active agent" is a subset of cosmetic agents as defined herein and includes generally any substance, as well as any component thereof, intended to be applied to the skin for the purpose of effectuating a treatment of an undesirable skin condition or disorder, or for achieving a desirable skin status. Examples relating to skin tone include skin pigmentation disorders, including disorders of hyperpigmentation, such as ephelides (freckles), lentigines including age spots (solar lentigos), post-inflammatory hyperpigmentation, Café au lait macules, Addisons disease and other systemic disease effects, hemochromatosis, melasma (mask of pregnancy and other hormonal related pigment disorders) and acanthosis nigricans, as well as phototoxia and medicinal-induced alternations in pigmentation. Examples of disorders of hypopigmentation include Vitiligo and skin trauma-related ablation of melanocytes in circumscribed areas. In some case a cosmetic consumer merely desires a change in pigmentation status of skin as determined by some cultural standard, such as skin lightening among some dark skinned people and skin darkening or tanning among some light skinned people.

Although the term "skin tone" is most often thought of with respect to skin pigmentation and evenness of coloration, "skin tone" may also include other characteristics of skin that contribute to a consumer perception of overall tone. For example, pore size and distribution, and skin texture are also generally considered attributes of overall skin tone.

Categorical examples of skin-active agents include skin pigment modifying agents, steroidal anti-inflammatory agents, non-steroidal anti-inflammatory agents, pediculocides, sensates, enzymes, vitamins, hair growth actives, sunscreens, and combinations thereof. Cosmetic compositions according to the instant invention may contain skin-active agents.

Many processes and proteins are known to be involved in the pigmentary process; there is a wide array of targets against which to screen for pigmentation control agents. Among the many targets are inhibitors of melanocyte stimulation (e.g., antioxidants, anti-inflammatory agents), cell receptor antagonists (e.g., alpha-MSH antagonists), inhibitors of melanin synthesis enzymes (e.g., tyrosinase, TRP-1, TRP-2), inhibitors of melanosome transport within the melanocyte and transfer to the keratinocyte (e.g., PAR-2 antagonists), and activators of melanin degradation within the keratinocyte.

Skin active agents which modify skin pigmentation are known in the art. Certain substances may only be considered cosmetic in severely reduced concentrations since there are side effects which suggest undesirable systemic activity beyond the cosmetic concern being addressed. These include hydroquinone, trans-retinoic acid, and corticosteroids. Generally, a classic target for cosmetic formulation is inhibition of tyrosinase, the first enzyme in the conversion of tyrosine to melanin. A wide array of compounds, such as kojic acid, arbutin, ascorbic acid, ellagic acid, sulfhydryl compounds, and resorcinols, are effective tyrosinase inhibitors, as is a more recently discussed deoxy-arbutin. However, since several of these materials also have other effects, it is difficult to directly connect a specific mechanism to the observed effect on pigmentation. Table A provides a short list of the many known targets and a few agents effective against them.

Generally, a "benchmark skin active agent" refers to any chemical, compound, environmental factor, small or large molecule, extract, formulation, or combinations thereof that is known to induce or cause a superior effect (positive or negative) on skin tissue. In accordance with the present invention, agents having known efficacy in either skin-lightening or skin darkening contexts are also herein referred to as "Benchmark Agents."

Non-limiting examples of benchmark skin active agents are set forth in Table A, along with the corresponding theorized pigmentation control target.

Newer benchmark skin active agents include niacinamide and glucosamine (in particular, its derivative N-acetyl glucosamine [NAG]), which have recently been shown to be effective in reducing melanin production in culture. In vitro, glucosamine reduces production of melanin by inhibiting activation of tyrosinase, while niacinamide inhibits melanosome transfer from melanocytes to keratinocytes. Cosmetic moisturizer formulations containing niacinamide alone are effective in reducing the appearance of hyperpigmented spots in vivo and the addition of NAG to the formula yields greater effectiveness. Another benchmark pigmentation control agent is N-undecylenoyl-L-phenylalanine, which has been reported to inhibit biding of alpha-MSH to the melanocyte in vitro and is effective as a component of cosmetic moisturizer formulations in clinical testing.

The terms "gene expression signature," and "gene-expression signature" refer to a rationally derived list, or plurality of lists, of genes representative of a skin tissue condition or a skin agent. In specific contexts, the skin agent may be a benchmark skin active agent or a potential skin agent. Thus, the gene expression signature may serve as a proxy for a phenotype of interest for skin tissue. A gene expression signature may comprise genes whose expression, relative to a normal or control state, is increased (up-regulated), whose expression is decreased (down-regulated), and combinations thereof. Generally, a gene expression signature for a modified cellular phenotype may be described as a set of genes differentially expressed in the modified cellular phenotype compared to the cellular phenotype. A gene expression signature can be derived from various sources of data, including but not limited to, from in vitro testing, in vivo testing and combinations thereof. In some embodiments, a gene expression signature may comprise a first list representative of a plurality of up-regulated genes of the condition of interest and a second list representative of a plurality of down-regulated genes of the condition of interest.

As used herein, the term "query" refers to data that is used as an input to a Connectivity Map and against which a plurality of instances are compared. A query may include a gene expression signature associated with a skin condition such as age spots, or may include a gene expression signature derived from a physiological process associated with a skin condition. A C-map may be queried with perturbagens, gene expression signatures, skin disorders, thematic signatures, or any data feature or combination of data features or associations that comprise the data architecture.

The term "instance," as used herein, refers to data from a gene expression profiling experiment in which skin cells are dosed with a perturbagen. In some embodiments, the data comprises a list of identifiers representing the genes that are part of the gene expression profiling experiment. The identifiers may include gene names, gene symbols; microarray probe set IDs, or any other identifier. In some embodiments, an instance may comprise data from a microarray experiment and comprises a list of probe set IDs of the microarray ordered by their extent of differential expression relative to a control. The data may also comprise metadata, including but not limited to data relating to one or more of the perturbagen, the gene expression profiling test conditions, the skin cells, and the microarray.

The term "perturbagen," as used herein, means anything used as a challenge in a gene expression profiling experiment to generate gene expression data for use in the present invention. In some embodiments, the perturbagen is applied to human cells and the gene expression data derived from the gene expression profiling experiment may be stored as an instance in a data architecture. Human cells in accordance with the invention may be keratinocyte, melanocyte, fibroblast, or melanoma cells. Any substance, chemical, compound, active, natural product, extract, drug [e.g. Sigma-Aldrich LOPAC (Library of Pharmacologically Active Compounds) collection], small molecule, and combinations thereof used as to generate gene expression data can be a perturbagen. A perturbagen can also be any other stimulus used to generate differential gene expression data. For example, a perturbagen may also be UV radiation, heat, osmotic stress, pH, a microbe, a virus, and small interfering RNA. A perturbagen may be, but is not required to be, any cosmetic agent.

The term "dermatologically acceptable," as used herein, means that the compositions or components described are suitable for use in contact with human skin tissue.

As used herein, the term "computer readable medium" refers to any electronic storage medium and includes but is not limited to any volatile, nonvolatile, removable, and non-removable media implemented in any method or technology for storage of information such as computer readable instructions, data and data structures, digital files, software programs and applications, or other digital information. Computer readable media includes, but are not limited to, application-specific integrated circuit (ASIC), a compact disk (CD), a digital versatile disk (DVD), a random access memory (RAM), a synchronous RAM (SRAM), a dynamic RAM (DRAM), a synchronous DRAM (SDRAM), double data rate SDRAM (DDR SDRAM), a direct RAM bus RAM (DRRAM), a read only memory (ROM), a programmable read only memory (PROM), an electronically erasable programmable read only memory (EEPROM), a disk, a carrier wave, and a memory stick. Examples of volatile memory include, but are not limited to, random access memory (RAM), synchronous RAM (SRAM), dynamic RAM (DRAM), synchronous DRAM (SDRAM), double data rate SDRAM (DDR SDRAM), and direct RAM bus RAM (DRRAM). Examples of non-volatile memory include, but are not limited to, read only memory (ROM), programmable read only memory (PROM), erasable programmable read only memory (EPROM), and electrically erasable programmable read only memory (EEPROM). A memory can store processes and/or data. Still other computer readable media include any suitable disk media, including but not limited to, magnetic disk drives, floppy disk drives, tape drives, Zip drives, flash memory cards, memory sticks, compact disk ROM (CD-ROM), CD recordable drive (CD-R drive), CD rewriteable drive (CD-RW drive), and digital versatile ROM drive (DVD ROM).

As used herein, the terms "software" and "software application" refer to one or more computer readable and/or executable instructions that cause a computing device or other electronic device to perform functions, actions, and/or behave in a desired manner. The instructions may be embodied in one or more various forms like routines, algorithms, modules, libraries, methods, and/or programs. Software may be implemented in a variety of executable and/or loadable forms and can be located in one computer component and/or distributed between two or more communicating, co-operating, and/or parallel processing computer components and thus can be loaded and/or executed in serial, parallel, and other manners. Software can be stored on one or more computer readable medium and may implement, in whole or part, the methods and functionalities of the present invention.

As used herein, the term "hyperpigmentation gene expression signature" refers to a gene expression signature derived from gene expression profiling of a hyperpigmentation condition.

As used herein, the term "connectivity score" refers to a derived value representing the degree to which an instance correlates to a query.

As used herein, the term "data architecture" refers generally to one or more digital data structures comprising an organized collection of data. In some embodiments, the digital data structures can be stored as a digital file (e.g., a spreadsheet file, a text file, a word processing file, a database file, etc.) on a computer readable medium. In some embodiments, the data architecture is provided in the form of a database that may be managed by a database management system (DBMS) that is be used to access, organize, and select data (e.g., instances and gene expression signatures) stored in a database.

As used herein, the terms "gene expression profiling" and "gene expression profiling experiment" refer to the measurement of the expression of multiple genes in a biological sample using any suitable profiling technology. For example, the mRNA expression of thousands of genes may be determined using microarray techniques. Other emerging technologies that may be used include RNA-Seq or whole transcriptome sequencing using NextGen sequencing techniques.

As used herein, the term "microarray" refers broadly to any ordered array of nucleic acids, oligonucleotides, proteins, small molecules, large molecules, and/or combinations thereof on a substrate that enables gene expression profiling of a biological sample. Non-limiting examples of microarrays are available from Affymetrix, Inc.; Agilent Technologies, Inc.; Illumina, Inc.; GE Healthcare, Inc.; Applied Biosystems, Inc.; Beckman Coulter, Inc.; etc.

Unless otherwise indicated, all numbers expressing quantities of ingredients, properties such as molecular weight, reaction conditions, and so forth as used in the specification and claims are to be understood as being modified in all instances by the term "about". Additionally, the disclosure of any ranges in the specification and claims are to be understood as including the range itself and also anything subsumed therein, as well as endpoints. All numeric ranges are inclusive of narrower ranges; delineated upper and lower range limits are interchangeable to create further ranges not explicitly delineated. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

In accordance with one aspect of the present invention, provided are devices, systems and methods for implementing a connectivity map utilizing one or more query signatures associated with a pigmentation or pigmentation-related condition. The query signatures may be derived in variety of ways. In some embodiments, the query signatures may be gene expression signatures derived from gene expression profiling of full thickness skin biopsies of skin exhibiting a skin condition of interest compared to a control. The gene expression profiling can be carried out using any suitable technology, including but not limited to microarray analysis or NextGen sequencing. An example of a gene expression signature includes a hyperpigmentation gene expression signature, an example of which is described more fully hereafter. A query signature may be derived from transcriptional profiling of a keratinocyte, fibroblast, melanocyte, or melanoma cell line exposed to benchmark skin-active agents such as skin-lightening agents. In other embodiments, the query signature may be a benchmark gene expression signature wherein a skin-lightening benchmark signature is further refined by comparing it to a skin-darkening benchmark signature and genes having similar directional regulation are eliminated. In further embodiments a cell is treated with more than one benchmark skin active agent to derive a benchmark composite signature, and in specific embodiments, the cell is treated with a plurality of benchmark skin active agents wherein the selected agents include those acting from different mechanisms known to underpin skin pigmentation. In other specific embodiments a general benchmark skin tone signature may be generated by treating a cell with a plurality of benchmark skin active agents including agents comprising benchmark skin active agents for skin pigmentation, skin pore size and distribution, and/or skin texture. These query signatures may be used singularly or in combination. In specific embodiments a composite signature has been shown to provide advantages in predicting gene changes for chemicals affecting tone versus signatures from single chemicals.

In accordance with another aspect of the present invention, provided are devices, systems, and methods for implementing a connectivity map utilizing one or more instances derived from a perturbagen, such as a cosmetic agent, exposed to an epidermal or dermal cell line, including for example keratinocyte, fibroblast, melanocyte and melanoma cells. Instances from more complex cell culture systems may also be used, such as skin organotypic cultures containing the targeted cell or ex vivo human skin. Instances from a plurality of cell lines may be used with the present invention.

In accordance with yet another aspect of the present invention, provided are devices, systems and methods for identification of relationships between a skin condition, e.g. skin hyperpigmentation condition query signature and a plurality of instances, where the query signature may be a gene expression signature or a physiological theme expression signature. For example, it may be possible to ascertain perturbagens that give rise to a statistically significant activity on a statistically significant number of genes associated with a skin condition of interest, leading to the identification of new cosmetic agents for treating the skin condition or new uses of known cosmetic agents.

I. Systems and Devices

Figure 5:
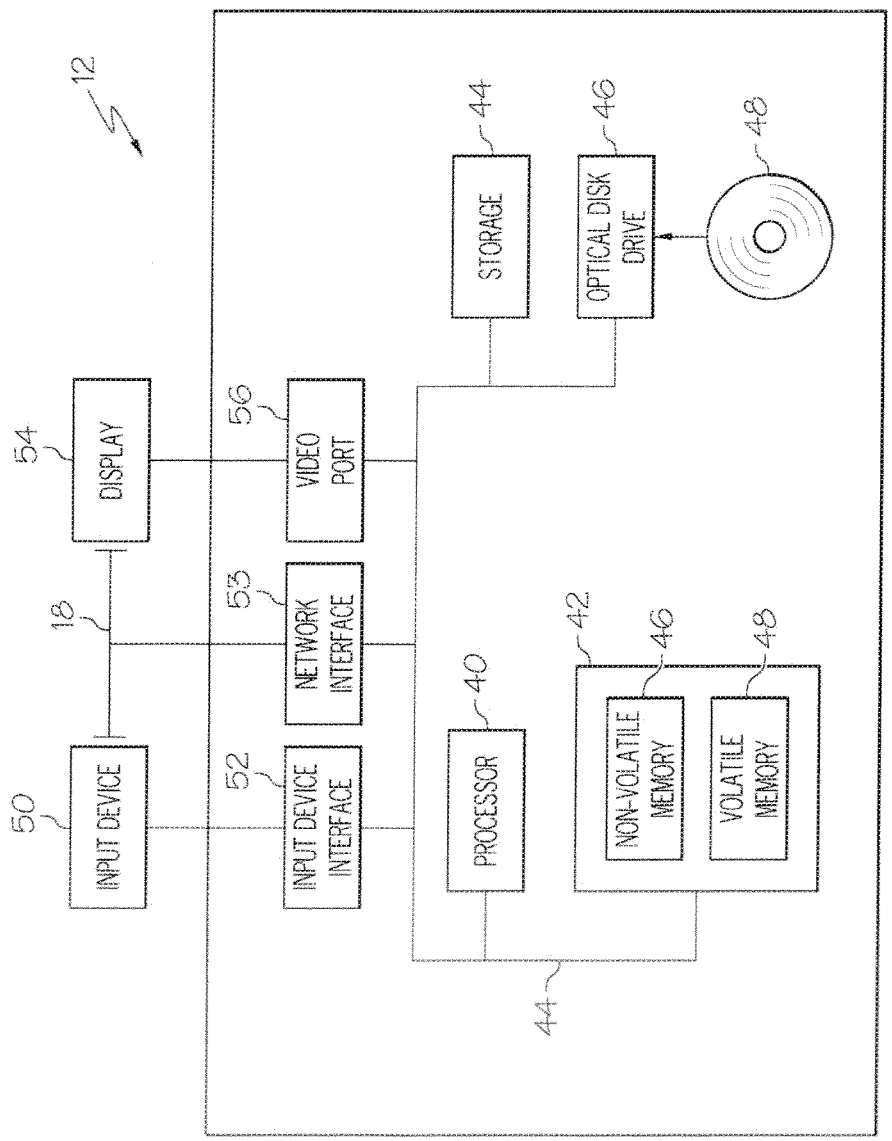
FIG. 5 is a schematic illustration of a programmable computer suitable for use with the present invention.
Figure 6:
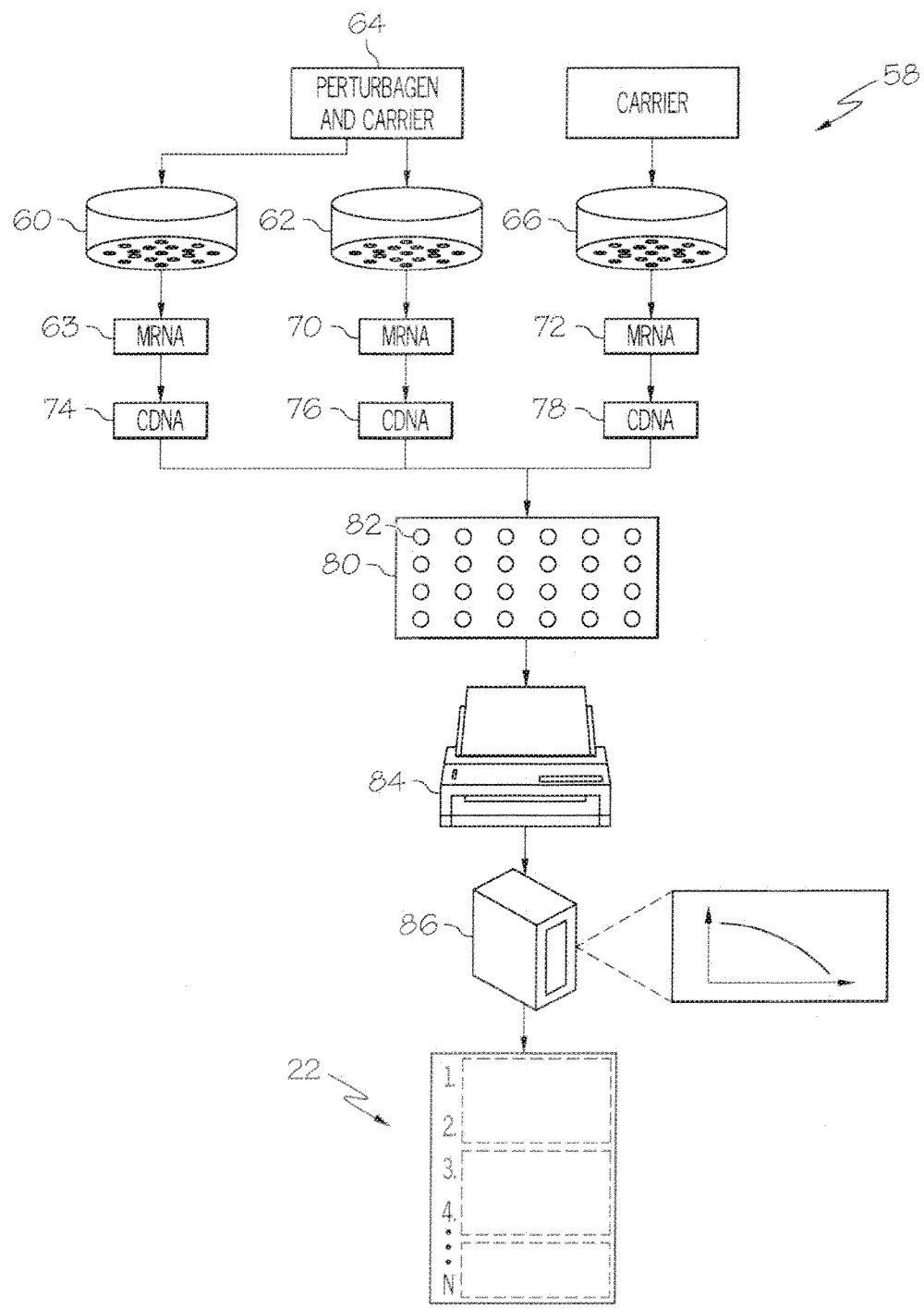
FIG. 6 is a schematic illustration of an exemplary system for generating an instance.

Referring to FIGS. 3, 5 and 6, some examples of systems and devices in accordance with the present invention for use in identifying relationships between perturbagens, skin pigmentation conditions, and genes associated with the skin pigmentation condition will now be described. System 10 comprises one or more of computing devices 12, 14, a computer readable medium 16 associated with the computing device 12, and communication network 18.

The computer readable medium 16, which may be provided as a hard disk drive, comprises a digital file 20, such as a database file, comprising a plurality of instances 22, 24, and 26 stored in a data structure associated with the digital file 20. The plurality of instances may be stored in relational tables and indexes or in other types of computer readable media. The instances 22, 24, and 26 may also be distributed across a plurality of digital files, a single digital file 20 being described herein however for simplicity.

The digital file 20 can be provided in wide variety of formats, including but not limited to a word processing file format (e.g., Microsoft Word), a spreadsheet file format (e.g., Microsoft Excel), and a database file format. Some common examples of suitable file formats include, but are not limited to, those associated with file extensions such as *.xls, *.xld, *.xlk, *.xll, *.xlt, *.xlxs, *.dif, *.db, *.dbf, *.accdb, *.mdb, *.mdf, *.cdb, *.fdb, *.csv, *sql, *.xml, *.doc, *.txt, *.rtf, *.log, *.docx, *.ans, *.pages, *.wps, etc.

Figure 4:
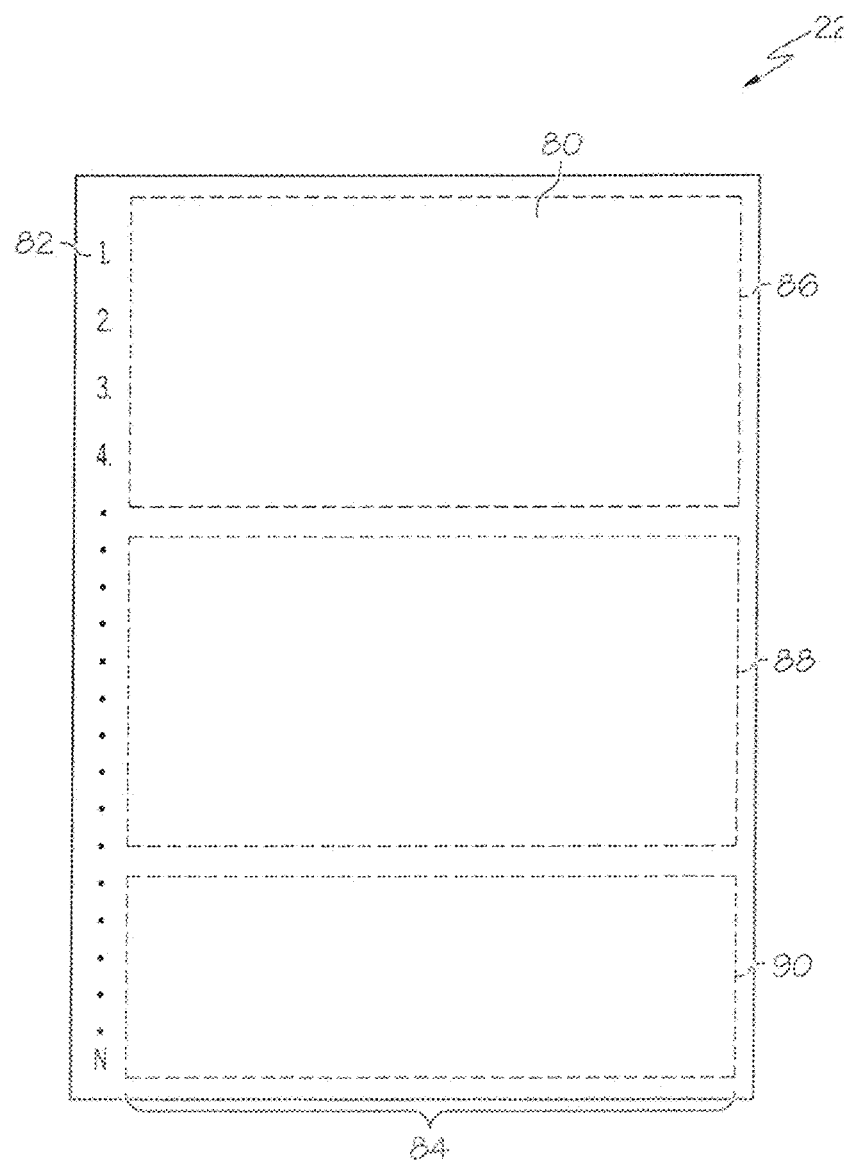
FIG. 4 is a schematic illustration of an instance associated with a computer readable medium of the computer system of FIG. 3.

Referring to FIG. 4, in some embodiments the instance 22 may comprise an ordered listing of microarray probe set IDs, wherein the value of N is equal to the total number of probes on the microarray used in analysis. Common microarrays include Affymetrix GeneChips and Illumina BeadChips, both of which comprise probe sets and custom probe sets. To generate the reference gene profiles according to the invention, preferred chips are those designed for profiling the human genome. Examples of Affymetrix chips with utility in the instant invention include model Human Genome HG-U133 Plus 2.0 and HG-U219. A specific Affymetrix chip employed by the instant investigators is HG-U133A2.0, however it will be understood by a person or ordinary skill in the art that any chip or microarray, regardless of proprietary origin, is suitable so long as the probe sets of the chips used to construct a data architecture according to the invention are substantially similar.

Instances derived from microarray analyses utilizing Affymetrix GeneChips may comprise an ordered listing of gene probe set IDs where the list comprises 22,000+IDs. The ordered listing may be stored in a data structure of the digital file 20 and the data arranged so that, when the digital file is read by the software application 28, a plurality of character strings are reproduced representing the ordered listing of probe set IDs. While it is preferred that each instance comprise a full list of the probe set IDs, it is contemplated that one or more of the instances may comprise less than all of the probe set IDs of a microarray. It is also contemplated that the instances may include other data in addition to or in place of the ordered listing of probe set IDs. For example, an ordered listing of equivalent gene names and/or gene symbols may be substituted for the ordered listing of probe set IDs. Additional data may be stored with an instance and/or the digital file 20. In some embodiments, the additional data is referred to as metadata and can include one or more of cell line identification, batch number, exposure duration, and other empirical data, as well as any other descriptive material associated with an instance ID. The ordered list may also comprise a numeric value associated with each identifier that represents the ranked position of that identifier in the ordered list.

Referring again to FIGS. 3, 4 and 5, the computer readable medium 16 may also have a second digital file 30 stored thereon. The second digital file 30 comprises one or more lists 32 of microarray probe set IDs associated with one or more pigmentation-relevant gene expression signatures. The listing 32 of microarray probe set IDs typically comprises a much smaller list of probe set IDs than the instances of the first digital file 20. In some embodiments, the list comprises between 2 and 1000 probe set IDs. In other embodiments the list comprises greater than 10, 50, 100, 200, or 300 and/or less than about 800, 600, or about 400 probe set IDs. The listing 32 of probe set IDs of the second digital file 30 comprises a list of probe set IDs representing up, and/or down-regulated genes selected to represent a skin tone condition of interest. In some embodiments, a first list may represent the up-regulated genes and a second list may represent the down-regulated genes of the gene expression signature. The listing(s) may be stored in a data structure of the digital file 30 and the data arranged so that, when the digital file is read by the software application 28, a plurality of character strings are reproduced representing the list of probe set IDs. Instead of probe set IDs, equivalent gene names and/or gene symbols (or another nomenclature) may be substituted for a list of probe set IDs. Additional data may be stored with the gene expression signature and/or the digital file 30 and this is commonly referred to as metadata, which may include any associated information, for example, cell line or sample source, and microarray identification. Examples of listings of probe set IDs for a skin hyperpigmentation gene expression signature, specifically wherein the skin hyperpigmentation condition is age spots, is set forth in FIG. 2, Tables B (the 200 most up-regulated genes) and C (the 200 most down-regulated genes in a skin hyperpigmentation gene expression signature). In some embodiments, one or more skin hyperpigmentation condition gene expression signatures may be stored in a plurality of digital files and/or stored on a plurality of computer readable media. In other embodiments, a plurality of gene expression signatures (e.g., 32, 34) may be stored in the same digital file (e.g., 30) or stored in the same digital file or database that comprises the instances 22, 24, and 26.

As previously described, the data stored in the first and second digital files may be stored in a wide variety of data structures and/or formats. In some embodiments, the data is stored in one or more searchable databases, such as free databases, commercial databases, or a company's internal proprietary database. The database may be provided or structured according to any model known in the art, such as for example and without limitation, a flat model, a hierarchical model, a network model, a relational model, a dimensional model, or an object-oriented model. In some embodiments, at least one searchable database is a company's internal proprietary database. A user of the system 10 may use a graphical user interface associated with a database management system to access and retrieve data from the one or more databases or other data sources to which the system is operably connected. In some embodiments, the first digital file 20 is provided in the form of a first database and the second digital file 30 is provided in the form of a second database. In other embodiments, the first and second digital files may be combined and provided in the form of a single file.

In some embodiments, the first digital file 20 may include data that is transmitted across the communication network 18 from a digital file 36 stored on the computer readable medium 38. In one embodiment, the first digital file 20 may comprise gene expression data obtained from a cell line (e.g., a fibroblast cell line and/or a keratinocyte cell line) as well as data from the digital file 36, such as gene expression data from other cell lines or cell types, gene expression signatures, perturbagen information, clinical trial data, scientific literature, chemical databases, pharmaceutical databases, and other such data and metadata. The digital file 36 may be provided in the form of a database, including but not limited to Sigma-Aldrich LOPAC collection, Broad Institute C-MAP collection, GEO collection, and Chemical Abstracts Service (CAS) databases.

The computer readable medium 16 (or another computer readable media, such as 16) may also have stored thereon one or more digital files 28 comprising computer readable instructions or software for reading, writing to, or otherwise managing and/or accessing the digital files 20, 30. The computer readable medium 16 may also comprise software or computer readable and/or executable instructions that cause the computing device 12 to perform one or more steps of the methods of the present invention, including for example and without limitation, the step(s) associated with comparing a gene expression signature stored in digital file 30 to instances 22, 24, and 26 stored in digital file 20. In some embodiments, the one or more digital files 28 may form part of a database management system for managing the digital files 20, 28. Non-limiting examples of database management systems are described in U.S. Pat. Nos. 4,967,341 and 5,297,279.

The computer readable medium 16 may form part of or otherwise be connected to the computing device 12. The computing device 12 can be provided in a wide variety of forms, including but not limited to any general or special purpose computer such as a server, a desktop computer, a laptop computer, a tower computer, a microcomputer, a mini computer, and a mainframe computer. While various computing devices may be suitable for use with the present invention, a generic computing device 12 is illustrated in FIG. 5. The computing device 12 may comprise one or more components selected from a processor 40, system memory 42, and a system bus 44. The system bus 44 provides an interface for system components including but not limited to the system memory 42 and processor 40. The system bus 36 can be any of several types of bus structures that may further interconnect to a memory bus (with or without a memory controller), a peripheral bus, and a local bus using any of a variety of commercially available bus architectures. Examples of a local bus include an industrial standard architecture (USA) bus, a microchannel architecture (MSA) bus, an extended ISA (EISA) bus, a peripheral component interconnect (PCI) bus, a universal serial (USB) bus, and a small computer systems interface (SCSI) bus. The processor 40 may be selected from any suitable processor, including but not limited to, dual microprocessor and other multiprocessor architectures. The processor executes a set of stored instructions associated with one or more program applications or software.

The system memory 42 can include non-volatile memory 46 (e.g., read only memory (ROM), erasable programmable read only memory (EPROM), electrically erasable programmable read only memory (EEPROM), etc.) and/or volatile memory 48 (e.g., random access memory (RAM)). A basic input/output system (BIOS) can be stored in the non-volatile memory 38, and can include the basic routines that help to transfer information between elements within the computing device 12. The volatile memory 48 can also include a high-speed RAM such as static RAM for caching data.

The computing device 12 may further include a storage 44, which may comprise, for example, an internal hard disk drive [HDD,e.g., enhanced integrated drive electronics (EIDE) or serial advanced technology attachment (SATA)] for storage. The computing device 12 may further include an optical disk drive 46 (e.g., for reading a CD-ROM or DVD-ROM 48). The drives and associated computer-readable media provide non-volatile storage of data, data structures and the data architecture of the present invention, computer-executable instructions, and so forth. For the computing device 12, the drives and media accommodate the storage of any data in a suitable digital format. Although the description of computer-readable media above refers to an HDD and optical media such as a CD-ROM or DVD-ROM, it should be appreciated by those skilled in the art that other types of media which are readable by a computer, such as Zip disks, magnetic cassettes, flash memory cards, cartridges, and the like may also be used, and further, that any such media may contain computer-executable instructions for performing the methods of the present invention.

A number of software applications can be stored on the drives 44 and volatile memory 48, including an operating system and one or more software applications, which implement, in whole or part, the functionality and/or methods described herein. It is to be appreciated that the embodiments can be implemented with various commercially available operating systems or combinations of operating systems. The central processing unit 40, in conjunction with the software applications in the volatile memory 48, may serve as a control system for the computing device 12 that is configured to, or adapted to, implement the functionality described herein.

A user may be able to enter commands and information into the computing device 12 through one or more wired or wireless input devices 50, for example, a keyboard, a pointing device, such as a mouse (not illustrated), or a touch screen. These and other input devices are often connected to the central processing unit 40 through an input device interface 52 that is coupled to the system bus 44 but can be connected by other interfaces, such as a parallel port, an IEEE 1394 serial port, a game port, a universal serial bus (USB) port, an IR interface, etc. The computing device 12 may drive a separate or integral display device 54, which may also be connected to the system bus 44 via an interface, such as a video port 56.

The computing devices 12, 14 may operate in a networked environment across network 18 using a wired and/or wireless network communications interface 58. The network interface port 58 can facilitate wired and/or wireless communications. The network interface port can be part of a network interface card, network interface controller (NIC), network adapter, or LAN adapter. The communication network 18 can be a wide area network (WAN) such as the Internet, or a local area network (LAN). The communication network 18 can comprise a fiber optic network, a twisted-pair network, a Tl/El line-based network or other links of the T-carrier/E carrier protocol, or a wireless local area or wide area network (operating through multiple protocols such as ultra-mobile band (UMB), long term evolution (LTE), etc.). Additionally, communication network 18 can comprise base stations for wireless communications, which include transceivers, associated electronic devices for modulation/demodulation, and switches and ports to connect to a backbone network for backhaul communication such as in the case of packet-switched communications.

II. Methods for Creating a Plurality of Instances

In some embodiments, the methods of the present invention may comprise populating at least the first digital file 20 with a plurality of instances (e.g., 22, 24, 26) comprising data derived from a plurality of gene expression profiling experiments, wherein one or more of the experiments comprise exposing, for example, keratinocyte cells (or other skin cells such as human skin equivalent cultures or ex vivo cultured human skin) to at least one perturbagen. For simplicity of discussion, the gene expression profiling discussed hereafter will be in the context of a microarray experiment.

Referring to FIG. 6, one embodiment of a method of the present invention is illustrated. The method 58 comprises exposing a keratinocyte cell to a perturbagen 64. The perturbagen may be dissolved in a carrier, such as dimethyl sulfoxide (DMSO). After exposure, mRNA is extracted from the cells exposed to the perturbagen and reference cells 66 (e.g., keratinocyte cells) which are exposed to only the carrier. The mRNA 68, 70, 72 may be reverse transcribed to cDNA 64, 76, 78 and marked with different fluorescent dyes (e.g., red and green) if a two color microarray analysis is to be performed. Alternatively, the samples may be prepped for a one color microarray analysis, and further a plurality of replicates may be processed if desired. The cDNA samples may be co-hybridized to the microarray 80 comprising a plurality of probes 82. The microarray may comprise thousands of probes 82. In some embodiments, there are between 10,000 and 50,000 gene probes 82 present on the microarray 80. The microarray is scanned by a scanner 84, which excites the dyes and measures the amount fluorescence. A computing device 86 may be used to analyze the raw images to determine the expression levels of a gene in the cells 60, 62 relative to the reference cells 66. The scanner 84 may incorporate the functionality of the computing device 86. The expression levels include: i) up-regulation [e.g., greater binding of the test material (e.g., cDNA 74, 76) to the probe than the reference material (e.g., cDNA 78)], or ii) down-regulation [e.g., greater binding of the reference material (e.g., cDNA 78) to the probe than the test material (e.g., cDNA 74, 76)], iii) expressed but not differentially [e.g., similar binding of the reference material (e.g., cDNA 78) to the probe than the test material (e.g., cDNA 74. 76)], and iv) no detectable signal or noise. The up- and down-regulated genes are referred to as differentially expressed. Microarrays and microarray analysis techniques are well known in the art, and it is contemplated that other microarray techniques may be used with the methods, devices and systems of the present invention. For example, any suitable commercial or non-commercial microarray technology and associated techniques may used. Good results have been obtained with Affymetrix GeneChip® technology and Illumina BeadChip™ technology. One illustrative technique is described in the Examples, "Generally Applicable" methods section. However, one of skill in the art will appreciate that the present invention is not limited to the methodology of the example and that other methods and techniques are also contemplated to be within its scope.

In a very specific embodiment, an instance consists of the rank ordered data for all of the probe sets on the Affymetrix HG-U133A2.0 GeneChip wherein each probe on the chip has a unique probe set Identifier. The probe sets are rank ordered by the fold change relative to the controls in the same C-map batch (single instance/average of controls). The probe set Identifiers are rank-ordered to reflect the most up-regulated to the most down-regulated.

Notably, even for the non-differentially regulated genes the signal values for a particular probe set are unlikely to be identical for the instance and control so a fold change different from 1 will be calculated that can be used for comprehensive rank ordering. In accordance with methods disclosed by Lamb et al. (2006), data are adjusted using 2 thresholds to minimize the effects of genes that may have very low noisy signal values, which can lead to spurious large fold changes. The thresholding is preferably done before the rank ordering. An example for illustrative purposes includes a process wherein a first threshold is set at 20. If the signal for a probe set is below 20, it is adjusted to 20. Ties for ranking are broken with a second threshold wherein the fold changes are recalculated and any values less than 2 are set to 2. For any remaining ties the order depends on the specific sorting algorithm used but is essentially random. The probe sets in the middle of the list do not meaningfully contribute to an actual connectivity score.

The rank ordered data are stored as an instance. The probes may be sorted into a list according to the level of gene expression regulation detected, wherein the list progresses from up-regulated to marginal or no regulation to down-regulated, and this rank ordered listing of probe IDs is stored as an instance (e.g., 22) in the first digital file 20. Referring to FIG. 4, the data associated with an instance comprises the probe ID 80 and a value 82 representing its ranking in the list (e.g., 1, 2, 3, 4 . . . N, where N represents the total number of probes on the microarray). The ordered list 84 may generally comprise approximately three groupings of probe IDs: a first grouping 86 of probe IDs associated with up-regulated genes, a second group 88 of probe IDs associated with genes with marginal regulation or no detectable signal or noise, and a third group 90 of probe IDs associated with down-regulated genes. The most up regulated genes are at or near the top of the list 84 and the most down-regulated genes are at or near the bottom of the list 84. The groupings are shown for illustration, but the lists for each instance may be continuous and the number of regulated genes will depend on the strength of the effect of the perturbagen associated with the instance. Other arrangements within the list 84 may be provided. For example, the probe IDs associated with the down-regulated genes may be arranged at the top of the list 84. This instance data may also further comprise metadata such as perturbagen identification, perturbagen concentration, cell line or sample source, and microarray identification.

In some embodiments, one or more instances comprise at least about 1,000, 2,500, 5,000, 10,000, or 20,000 identifiers and/or less than about 30,000, 25,000, or 20,000 identifiers. In some embodiments, the database comprises at least about 50, 100, 250, 500, or 1,000 instances and/or less than about 50,000, 20,000, 15,000, 10,000, 7,500, 5,000, or 2,500 instances. Replicates of an instance may be created, and the same perturbagen may be used to derive a first instance from keratinocyte cells and a second instance from another skin cell type, such as fibroblasts, melanocytes, melanoma or complex tissue, for example ex vivo human skin.

The present inventors have discovered that instances derived with a cell type, such as keratinocyte cells, are more predictive than other cell types when used in combination with a skin lightening benchmark agent expression signature derived from the same cell type. In other words, better results are achieved if the cell type used to generate the query signature is the same as the instance cell type. While this cell-consistency guide may appear predictable, what is surprising is that with respect to benchmark agent signatures the present inventors surprisingly discovered that certain benchmark skin active agents have greater predictive efficacy with certain cell types over others. For example, as set forth in Examples 4 and 5, the present inventors compared Retinoic Acid benchmark gene expression signatures derived from BJ fibroblast cells and keratinocyte cells, it was surprisingly discovered that those derived from keratinocyte cells yield better results with respect to a potential agent hit list based on connectivity with the query signature.

III. Methods for Deriving Hyperpigmentation Gene Expression Signatures

Some methods of the present invention comprise identifying a gene expression signature that represents the up-regulated and down-regulated genes associated with a skin condition of interest, in particular with skin tone or hyperpigmentation.

The pathogenesis of a skin pigmentation condition typically involves complex processes involving numerous known and unknown extrinsic and intrinsic factors, as well as responses to such factors that are subtle over a relatively short period of time but non-subtle over a longer period of time. This is in contrast to what is typically observed in drug development and drug screening methods, wherein a specific target, gene, or mechanism of action is of interest. Due to the unique screening challenges associated with a skin pigmentation condition, the quality of the gene expression signature representing the condition of interest can be important for distinguishing between the gene expression data actually associated with a response to a perturbagen from the background expression data.

One challenge in developing gene expression signatures for skin tone and pigmentation-related skin disorders is that the number of genes selected needs to be adequate to reflect the dominant and key biology but not so large as to include many genes that have achieved a level of statistical significance by random chance and are non-informative. Thus, query signatures should be carefully derived since the predictive value may be dependent upon the quality of the gene expression signature.

One factor that can impact the quality of the query signature is the number of genes included in the signature. The present inventors have found that, with respect to a cosmetic data architecture and connectivity map, too few genes can result in a signature that is unstable with regard to the highest scoring instances. In other words, small changes to the gene expression signature can result in significant differences in the highest scoring instance. Conversely, too many genes may tend to partially mask the dominant biological responses and will include a higher fraction of genes meeting statistical cutoffs by random chance—thereby adding undesirable noise to the signature. The inventors have found that the number of genes desirable in a gene expression signature is also a function of the strength of the biological response associated with the condition and/or the number of genes needed to meet minimal values (e.g., a p-value less than about 0.05 or less than about 1.0, or in accordance with applicable statistical principles) for statistical significance. Hence, what is considered an ideal number of genes will vary from condition to condition. When the biology is weaker, such as is the case typically with cosmetic condition phenotypes, fewer genes than those which may meet the statistical requisite for inclusion in the prior art, may be used to avoid adding noisy genes.

For example, the present inventors have determined that where gene expression profiling analysis of a skin condition yields from between about 2,000 and 4,000 genes having a statistical p-value of less than 0.05 and approximately 1000 genes having a p-value of less than 0.001, a very strong biological response is indicated. A moderately strong biological response may yield approximately 800-2000 genes have a statistical p-value of less than 0.05 combined with approximately 400-600 genes have a p-value of less than 0.001. In these cases, a gene expression signature comprising between about 100 and about 600 genes appears ideal. Weaker biology may be better represented by a gene expression signature comprising fewer genes, such as between about 20 and 100 genes.

While a gene expression signature may represent all significantly regulated genes associated with a skin condition of interest; typically it represents a subset of such genes. The present inventors have discovered that hyperpigmentation gene expression signatures comprising between about 50 and about 400 genes of approximately equal numbers of up-regulated and/or down-regulated genes are stable, reliable, and can provide predictive results. For example, a suitable gene expression signature may have from about 100-150 genes, 250-300 genes, 300-350 genes, or 350-400 genes. In a very specific embodiment, a hyperpigmentation gene expression signature includes the 100 most up- and down-regulated genes. However, one of skill in the art will appreciate that gene expression signatures comprising fewer or more genes are also within the scope of the various embodiments of the invention. For purposes of depicting a gene expression signature, the probe set IDs associated with the genes are preferably separated into a first list comprising the most up-regulated genes and a second list comprising the most down-regulated, as set forth in FIG. 2, Tables B and C.

Gene expression signatures may be generated from full thickness skin biopsies from skin having the skin condition of interest compared to a control. For generation of an exemplary hyperpigmentation gene expression signature, biopsies are taken from forearm age spots and compared to non-affected forearm skin sampled from the same subject.

In other embodiments of the present invention, a gene expression signature may be derived from a gene expression profiling analysis of keratinocyte, melanocyte, fibroblast or melanoma cells treated with one or more benchmark skin-active agents, in particular a skin-lightening agent, to represent cellular perturbations leading to improvement in the skin tissue condition treated with that benchmark skin active agent, wherein the signature comprises a plurality of genes up-regulated and down-regulated by the benchmark skin active agent in cells in vitro. As one illustrative example, microarray gene expression profile data where the perturbagen is the known skin lightening agent Niacinamide may be analyzed using the present invention to determine from the rank-ordered instances in the query results, the perturbagens associated with the highest scoring instances.

A composite benchmark signature according to the invention is a signature derived from a cell treated with more than one benchmark skin active agent (described in Examples 3, 6, and 7). The actives may be selected to reflect more than one mechanism of action in skin, or may be selected to reflect more than one attribute of general skin tone.

In a further specific embodiment, a benchmark skin-lightening gene expression signature is compared to a benchmark skin-darkening gene expression signature and genes not differentially regulated between the two are eliminated from the signature intended to be the query signature. Non-limiting examples of skin-darkening agents according to this embodiment include alpha-melanocyte-stimulating hormone (a-MSH) and any related melanocortin 1 receptor agonists or stimulant thereof.

Figure 7:
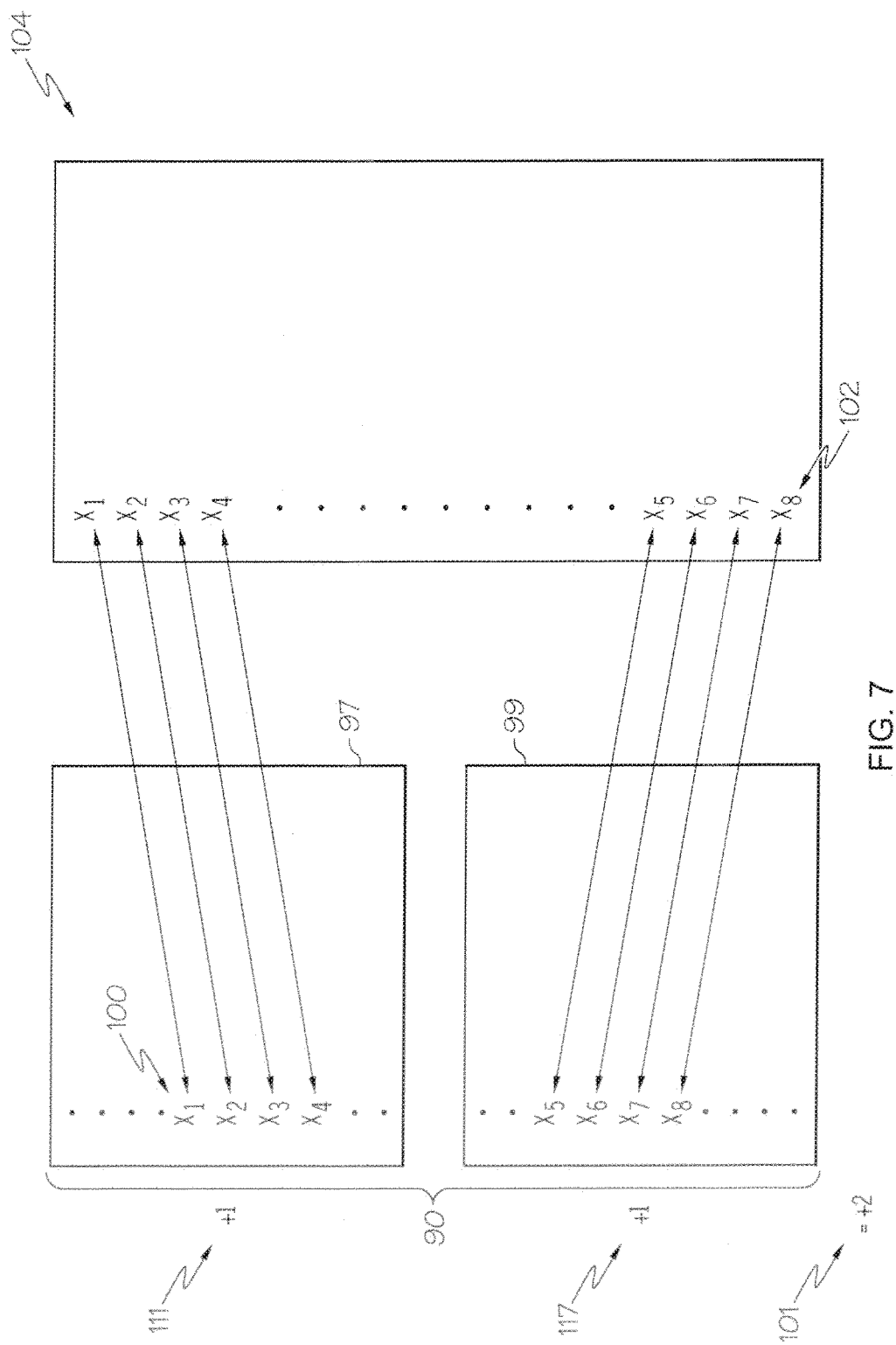
FIG. 7 is a schematic illustration of a comparison between a gene expression signature and an instance, wherein there is a positive correlation between the lists.
Figure 8:
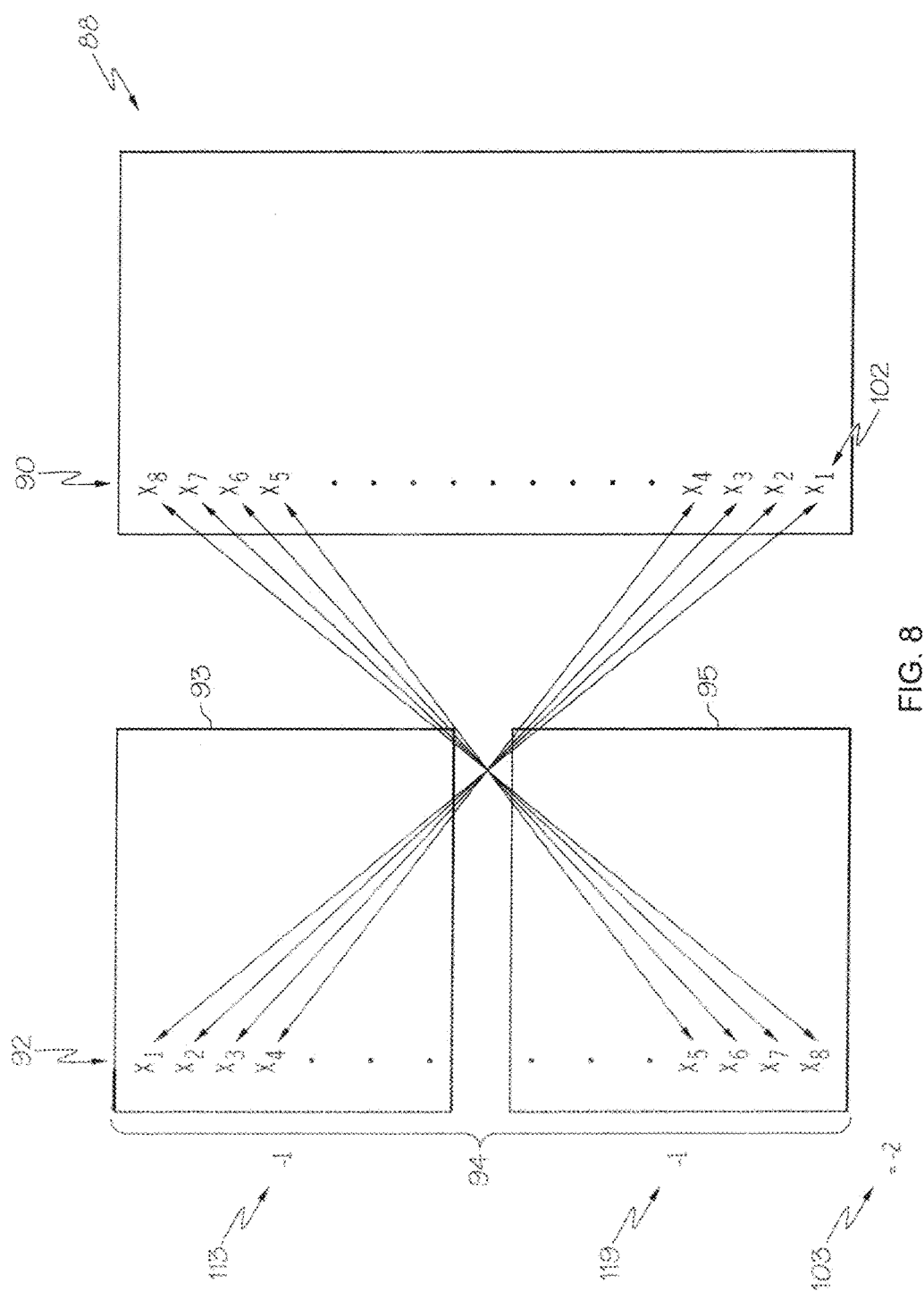
FIG. 8 is a schematic illustration of a comparison between a gene expression signature and an instance, wherein there is a negative correlation between the lists.
Figure 9:
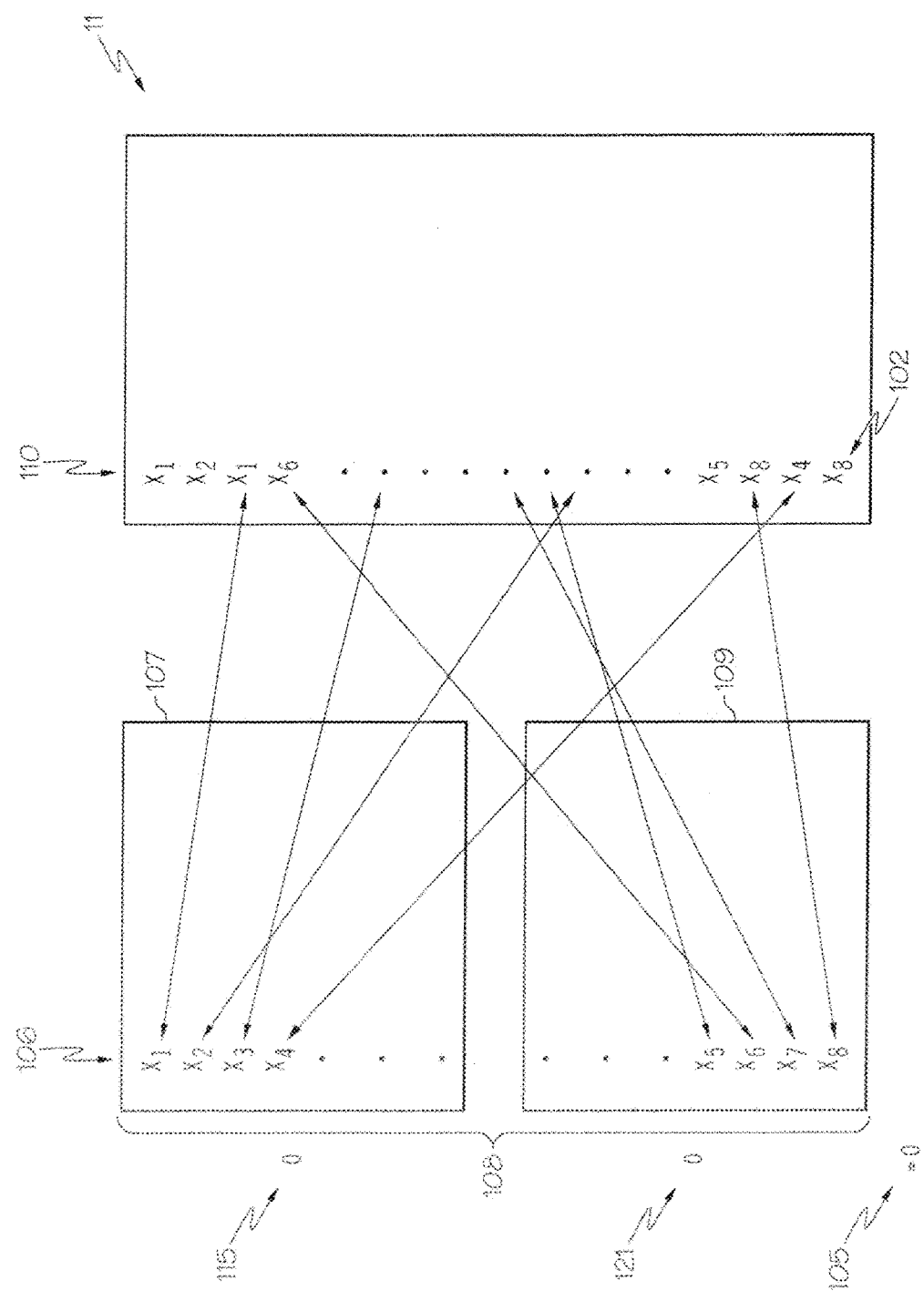
FIG. 9 is a schematic illustration of a comparison between a gene expression signature and an instance, wherein there is a neutral correlation between the lists.

IV. Methods for Comparing a Plurality of Instances to One or More Pigmentation Gene Expression Signatures Referring to FIG. 7 and FIG. 8, a method for querying a plurality of instances with one or more hyperpigmentation-relevant gene signatures will now be described. Broadly, the method comprises querying a plurality of instances with one or more hyperpigmentation-relevant gene signatures and applying a statistical method to determine how strongly the signature genes match the regulated genes in an instance. Positive connectivity occurs when the genes in the up-regulated signature list are enriched among the up-regulated genes in an instance and the genes in the down-regulated signature list are enriched among the down-regulated genes in an instance. On the other hand, if the up-regulated genes of the signature are predominantly found among the down-regulated genes of the instance, and vice versa, this is scored as negative connectivity. FIG. 7 schematically illustrates an extreme example of a positive connectivity between signature 90 and the instance 104 comprising the probe IDs 102, wherein the probe IDs of the instance are ordered from most up-regulated to most down-regulated. In this example, the probe IDs 100 (e.g., $X_1$, $X_2$ $X_3$, $X_4$, $X_5$, $X_6$, $X_7$, $X_8$) of the gene signature 90, comprising an up list 97 and a down list 99, have a one to one positive correspondence with the most up-regulated and down-regulated probe IDs 102 of the instance 104, respectively. Similarly, FIG. 8 schematically illustrates an extreme example of a negative connectivity between signature 94 and the instance 88 comprising the probe IDs 90, wherein the probe IDs of the instance are ordered from most up-regulated to most down-regulated. In this example, the probe IDs of the up list 93 (e.g., $X_1$, $X_2$ $X_3$, $X_4$) correspond exactly with the most down-regulated genes of the instance 88, and the probe IDs of the down list 95 (e.g., $X_5$, $X_6$, $X_7$, $X_8$) correspond exactly to the most up-regulated probe IDs of the instance 88. FIG. 9 schematically illustrates an extreme example of neutral connectivity, wherein there is no consistent enrichment of the up- and down-regulated genes of the signature among the up- and down-regulated genes of the instance, either positive or negative. Hence the probe IDs 106 (e.g., $X_1$, $X_2$ $X_3$, $X_4$, $X_5$, $X_6$, $X_7$, $X_8$) of a gene signature 108 (comprising an up list 107 and a down list 109) are scattered with respect to rank with the probe IDs 110 of the instance 112, wherein the probe IDs of the instance are ordered from most up-regulated to most down-regulated. While the above embodiments illustrate process where the gene signature comprises a both an up list and a down list representative of the most significantly up- and down-regulated genes of a skin condition, it is contemplated that the gene signature may comprise only an up list or a down list when the dominant biology associated with a condition of interest shows gene regulation in predominantly one direction.

In some embodiments, the connectivity score can be a combination of an up-score and a down score, wherein the up-score represents the correlation between the up-regulated genes of a gene signature and an instance and the down-score represents the correlation between the down-regulated genes of a gene signature and an instance. The up score and down score may have values between +1 and −1. For an up score (and down score) a high positive value indicates that the corresponding perturbagen of an instance induced the expression of the microarray probes of the up-regulated (or down-regulated) genes of the gene signature, and a high negative value indicates that the corresponding perturbagen associated with the instance repressed the expression of the microarray probes of the up-regulated (or down-regulated) genes of the gene signature. The up-score can be calculated by comparing each identifier of an up list of a gene signature comprising the up-regulated genes (e.g., Tables B, D, F, H and lists 93, 97, and 107) to an ordered instance list, while the down-score can be calculated by comparing each identifier of a down list of a gene signature comprising the down-regulated genes (see, e.g., Tables C, E, G, I and down lists 95, 99, and 109) to an ordered instance list. In these embodiments, the gene signature comprises the combination of the up list and the down list.

In some embodiments, the connectivity score value may range from +2 (greatest positive connectivity) to −2 (greatest negative connectivity), wherein the connectivity score (e.g., 101, 103, and 105) is the combination of the up score (e.g., 111, 113, 115) and the down score (e.g., 117, 119, 121) derived by comparing each identifier of a gene signature to the identifiers of an ordered instance list. In other embodiments the connectivity range may be between +1 and −1. Examples of the scores are illustrated in FIGS. 7, 8 and 9 as reference numerals 101, 103, 105, 111, 113, 115, 117, 119, and 121. The strength of matching between a signature and an instance represented by the up scores and down scores and/or the connectivity score may be derived by one or more approaches known in the art and include, but are not limited to, parametric and non-parametric approaches. Examples of parametric approaches include Pearson correlation (or Pearson r) and cosine correlation. Examples of non-parametric approaches include Spearman's Rank (or rank-order) correlation, Kendall's Tau correlation, and the Gamma statistic. Generally, in order to eliminate a requirement that all profiles be generated on the same microarray platform, a non-parametric, rank-based pattern matching strategy based on the Kolmogorov-Smirnov statistic (see M. Hollander et al. "*Nonparametric Statistical Methods*"; Wiley, New York, ed. 2, 1999) (see, e.g., pp. 178-185). It is noted, however, that where all expression profiles are derived from a single technology platform, similar results may be obtained using conventional measures of correlation, for example, the Pearson correlation coefficient.

In specific embodiments, the methods and systems of the present invention employ the nonparametric, rank-based pattern-matching strategy based on the Kolmogorov-Smirnov statistic, which has been refined for gene profiling data by Lamb's group, commonly known in the art as Gene Set Enrichment Analysis (GSEA) (see, e.g., Lamb et al. 2006 and Subramanian, A. et al. (2005) *Proc. Natl. Acad Sci U.S.A*, 102, 15545-15550). For each instance, a down score is calculated to reflect the match between the down-regulated genes of the query and the instance, and an up score is calculated to reflect the correlation between the up-regulated genes of the query and the instance. In certain embodiments the down score and up score each may range between −1 and +1. The combination represents the strength of the overall match between the query signature and the instance.

The combination of the up score and down score is used to calculate an overall connectivity score for each instance, and in embodiments where up and down score ranges are set between −1 and +1, the connectivity score ranges from −2 to +2, and represents the strength of match between a query signature and the instance. The sign of the overall score is determined by whether the instance links positivity or negatively to the signature. Positive connectivity occurs when the perturbagen associated with an instance tends to up-regulate the genes in the up list of the signature and down-regulate the genes in the down list. Conversely, negative connectivity occurs when the perturbagen tends to reverse the up and down signature gene expression changes, The magnitude of the connectivity score is the sum of the absolute values of the up and down scores when the up and down scores have different signs. A high positive connectivity score predicts that the perturbagen will tend to induce the condition that was used to generate the query signature, and a high negative connectivity score predicts that the perturbagen will tend to reverse the condition associated with the query signature. A zero score is assigned where the up and down scores have the same sign, indicating that a perturbagen did not have a consistent impact the condition signature (e.g., up-regulating both the up and down lists).

According to Lamb et al. (2006), there is no standard for estimating statistical significance of connections observed. Lamb teaches that the power to detect connections may be greater for compounds with many replicates. Replicating in this context means that the same perturbagen is profiled multiple times. Where batch to batch variation must be avoided, a perturbagen should be profiled multiple times in each batch. However, since microarray experiments tend to have strong batch effects it is desirable to replicate instances in different batches (i.e., experiments) to have the highest confidence that connectivity scores are meaningful and reproducible.

Each instance may be rank ordered according to its connectivity score to the query signature and the resulting rank ordered list displayed to a user using any suitable software and computer hardware allowing for visualization of data.

In some embodiments, the methods may comprise identifying from the displayed rank-ordered list of instances (i) the one or more perturbagens associated with the instances of interest (thereby correlating activation or inhibition of a plurality of genes listed in the query signature to the one or more perturbagens); (ii) the differentially expressed genes associated with any instances of interest (thereby correlating such genes with the one or more perturbagens, the skin tissue condition of interest, or both); (iii) the cells associated with any instance of interest (thereby correlating such cells with one or more of the differentially expressed genes, the one or more perturbagens, and the skin tissue condition of interest); or (iv) combinations thereof. The one or more perturbagens associated with an instance may be identified from the metadata stored in the database for that instance. However, one of skill in the art will appreciate that perturbagen data for an instance may be retrievably stored in and by other means. Because the identified perturbagens statistically correlate to activation or inhibition of genes listed in the query signature, and because the query signature is a proxy for a skin condition of interest, e.g. a hyperpigmentation condition, the identified perturbagens may be candidates for new cosmetic agents, new uses of known cosmetic agents, or to validate known agents for known uses relevant to the hyperpigmentation condition.

In some embodiments, the methods of the present invention may further comprise testing the selected candidate cosmetic agent, using in vitro assays and/or in vivo testing, to validate the activity of the agent and usefulness as a cosmetic agent. Any suitable in vitro test method can be used, including those known in the art, and most preferably in vitro models developed in accordance with the present invention. For example, MatTek human skin equivalent cultures or other skin equivalent cultures may be treated with one or a combination of perturbagens selected for mimicry of the skin condition of interest with respect to regulation of the genes constituting a physiological theme pattern for the skin condition of interest. In some embodiments, evaluation of selected agents using in vitro assays may reveal, confirm, or both, that one or more new candidate cosmetic agents may be used in conjunction with a known cosmetic agent (or a combination of known cosmetic agents) to regulate a skin condition of interest.

Clinical testing can be useful to confirm putative skin-pigmentation modifying efficacy. Clinical methods include live expert grading, chromameter, and color image capture and analysis. A new useful clinical measurement tool in assessing effectiveness is based on the principle of noncontact SIAscopy™, a recently described method to measure skin melanin content and distribution. It rapidly captures facial maps of skin chromophores, permitting determination of the content and distribution of melanin in any spot or any area of the skin. Clinical testing on various body sites such as forearm, face, chest, and back have been reported, and all have utility in evaluating technology. Any thoroughly controlled clinical evaluation is expensive and therefore practicality limits testing to only the most promising candidates.

V. Hyperpigmentation Disorders

The present invention provides methods for identifying putative skin active agents for the treatment of pigmentation conditions and disorders, and in particular those relating to hyperpigmentation. Main factors in the development of conditions of hyperpigmentation are exposure to certain environmental conditions and hormonal changes. In general, the number of active melanocytes per unit area of skin decreases with age (10-20% decline per decade), and there are more active melanocytes in chronically sun-exposed skin than in non-exposed skin. This increased number of active melanocytes in sun-damaged skin indicates the influence of chronic UV exposure (e.g., on face, hands, and arms) in stimulating melanogenic activity. Since chronic UV exposure also alters dermal fibroblast function in aging skin and since fibroblasts appear to play a regulatory role in melanin production, dermal damage from sunlight may contribute to the production of hyperpigmentation in exposed aging skin.

Post-inflammatory hyperpigmentation (PIH) results from inflammation of the skin and disproportionately affects people with darker skin. Inflammation induced pigmentation is often seen associated with acne lesions, ingrown hairs, scratches, insect bites, and surfactant damage. As an example of the latter, exposure of human forearm skin to the harsh surfactant sodium lauryl sulfate (SLS) under patch for a few hours will produce erythema within a day. Over the course of 1-2 weeks after this SLS exposure, hyperpigmentation will result, particularly in darker skin, but it will occur even in Caucasian skin. Topical treatment with anti-inflammatory agents is known to ameliorate this. A non-limiting example is phytosterol.

Exposure of skin to sunlight is the most common cause of skin hyperpigmentation and is increasingly believed that it is a subset of PIH caused by a post-inflammatory response to UV damage to skin. The inflammatory response may be the result of an obvious acute inflammatory event such as sunburn or due to repeated sub-erythemal exposures to UV. While in the latter, there may not be visible erythema, histologically, such exposed skin has elevated inflammatory cell content, yielding a "subclinical" inflammatory process. This explanation is supported by the fact that topical treatment with anti-inflammatory agents immediately after UVB exposure prevents induction of delayed tanning.

Inflammation may result in hyperpigmentation through several mechanisms. Among them is direct stimulation of melanocytes by inflammatory mediators such as IL-1-alpha. Reactive oxygen species such as superoxide and nitric oxide generated in damaged skin (e.g., from UV exposure) or released as by-products from inflammatory cells are also known stimulators of melanocytes. Additionally, damage induced in epidermal cells can lead to release of endocrine inducers of pigmentation such as alpha-melanin stimulating hormone (MSH). The resulting hyperpigmentation induced by all these effects is adaptive since it appears to provide some measure of protection against subsequent insult since melanin is known to have both UV absorption and reactive oxygen species scavenging capacity.

The melanin produced during an inflammatory event also can enter the dermis where it is engulfed by macrophages, producing "melanophages." These cells are often retained in the upper dermis for prolonged periods since removal of dermal melanin apparently is a very slow process. Thus, post-inflammatory hyperpigmentation can be a very long-lived problem for the skin.

Solar (Actinic) Lentigos are hyperpigmented spots also known as lentigines, age spots, and liver spots. They develop as a result of chronic exposure of skin to UV radiation and occur on sun-exposed parts of the body (in particular, the hands, arms, face, upper chest, and shoulders). Chronic exposure of skin to UV results in chronic inflammation, such as the epidermal endothelin cascade. The dark appearance of age spots results from excessive melanin in the region, and may result from overproduction of melanin in the hyperactive melanocytes, longer retention of melanin in aging epidermis due to the slower turnover of this tissue layer, longer retention of melanin in keratinocytes within rete ridges, and dermal melanin-containing melanophages, which have been observed histologically to lie beneath the lentigines. There is reduced wound healing with age at least in part due to reduced clearance of materials from dermis apparently due to vascular and lymphatic changes, so that the residence time of melanophages in dermis may be lengthened in older populations.

Certain observations suggest that there is a change in the genetic and phenotypic expression within an age spot as compared to cells in surrounding non-affected skin. For example, within lesional lentigo skin, the rete ridges are greatly exaggerated, extending deeper into the dermis. This deep penetration runs counter to the general observation of flattening of the convoluted dermal-epidermal junction with aging, evidenced by the diminution of the rete ridges. In solar lentigines, the basement membrane is also perturbed, which likely contributes to melanin entering the dermis to result in melanophage formation.

Moreover, the expression levels of several melanogenesis-associated genes are known to be increased in actinic lentigos. There is an accentuation of the epidermal endothelin inflammatory cascade, together with decreased proliferation and differentiation of lesional keratinocytes. Many of these changes appear to be permanent since these spots persist even when further UV exposure is avoided.

While lentigos appear to be permanent, their melanin content and thus their intensity will vary seasonally. For example, in evaluation of women with facial hyperpigmented spots in October versus December (in Kobe, Japan or Cincinnati, Ohio, USA), there is a marked reduction in the size of spots over that time period, suggesting that the lack of continued exposure to sunlight in winter leads to gradual reduction in melanin production (seasonal fading) even in hyperpigmented spots. Additionally, in a separate examination of facial spots in March versus May (in Cincinnati, Ohio, USA), a marked increase in the size of spots is observed, consistent with the expected increased pigmentation due to increased sun exposure in spring (seasonal darkening).

From a consumer appearance standpoint, hyperpigmented spots and uneven pigmentation are important in the perception of age. In a series of studies, facial images were digitally modified to remove all age-defining textural features (e.g., facial furrows, folds, lines, wrinkles) leaving only pigmentation as the variable. Studies have shown that when using naïve judge evaluation and computer image analysis of the facial images, pigmentation features can contribute to up to 20 years in perceived age of individuals.

The hyperpigmentary disorder generally referred to as melasma is not well understood. It occurs typically as symmetrical lesions on the face, primarily in darker skin type females at puberty or later in life. Sunlight exposure is likely a factor in the development of melasma since it occurs on the face (a sun-exposed body site) and since the condition worsens in the summer. Most melasma sufferers have a hypersensitivity to ultraviolet radiation, and even brief exposures to sunlight can stimulate hyperpigmentation. There is also a hormonal component, likely progesterone, since episodes of melasma are often associated with pregnancy and the use of hormonal birth control. There may also be an estrogen component since estrogen receptor expression is increased in melasma.

In melasma lesions, there is excess melanin present in both the epidermis and upper dermis, associated with extravascular macrophages. Since there is only a slight increase in the number of melanocytes, the abnormality appears to be in function of the skin cells, in particular, increase expression of factors in keratinocytes, fibroblasts, and melanocytes of the involved skin. In contrast to PIH, there is no apparent inflammatory phase involved in its development. Additionally, there is likely a genetic compound predisposing individuals to melasma, although the specific genetic basis for it is not defined.

The pigmentation process is complex as evidenced particularly by recent revelations from genomic and proteomic analysis. There are approximately 1,500 gene products (proteins) expressed in melanosomes of all developmental stages, with 600 of them being expressed at any given time, and with 100 of them apparently unique to the melanosome. Added to this are many other proteins (membrane-associated, cytoskeletal, transport, etc.) involved in pigmentation in both the melanocyte and the keratinocyte, indicating the complexity of the pigmentary process. While the basic process (e.g., stimulation of melanocytes and conversion of tyrosine to melanin) is well studied, there are many regulatory elements that have emerged from recent research involved in signaling, in the transport of melanosomes within the melanocyte, and the transfer of melanosomes to the keratinocyte.

VI. Cosmetic Compositions and Personal Care Products

Generally, skin-active agents identified for the enhancement of skin tone or for treatment of pigment-related skin conditions may be applied in accordance with cosmetic compositions and formulation parameters well-known in the art. Various methods of treatment, application, regulation, or improvement may utilize the skin care compositions comprising skin-active agents identified according to the inventive methods.

Skin hyperpigmentation as a cosmetic concern is generally treated by topical formulation administration, so that depigmentation is restricted to hyperpigmented areas and normal skin is left unaffected by the drug.

Because of the desirability of providing various cosmetic skin anti-aging benefits to a consumer, it may be beneficial to incorporate test agents or compounds identified by one or more of the screening methods described herein into a cosmetic composition suitable for topical application to skin. That is, it may be desirable to include the test agent as an ingredient in the cosmetic composition. In certain embodiments, the cosmetic composition may include a dermatological acceptable carrier, the test agent, and one or more optional ingredients of the kind commonly included in the particular cosmetic compositing being provided.

Dermatologically acceptable carriers should be safe for use in contact with human skin tissue. Suitable carriers may include water and/or water miscible solvents. The cosmetic skin care composition may comprise from about 1% to about 95% by weight of water and/or water miscible solvent. The composition may comprise from about 1%, 3%, 5%, 10%, 15%, 20%, 25%, 30%, 35%, 40%, 45%, 50%, 55%, 60%, 65%, 70%, 75%, 80%, or 85% to about 90%, 85%, 80%, 75%, 70%, 65%, 60%, 55%, 50%, 45%, 40%, 35%, 30%, 25%, 20%, 15%, 10%, or 5% water and/or water miscible solvents. Suitable water miscible solvents include monohydric alcohols, dihydric alcohols, polyhydric alcohols, glycerol, glycols, polyalkylene glycols such as polyethylene glycol, and mixtures thereof. When the skin care composition is in the form of an emulsion, water and/or water miscible solvents are carriers typically associated with the aqueous phase.

Suitable carriers also include oils. The skin care composition may comprise from about 1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water soluble solvents. Suitable oils include silicones, hydrocarbons, esters, amides, ethers, and mixtures thereof. The oils may be volatile or nonvolatile.

Suitable silicone oils include polysiloxanes. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.).

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N,-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The skin care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. Nos. 3,755,560, 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Emulsifiers also include emulsifying silicone elastomers. Suitable silicone elastomers may be in the powder form, or dispersed or solubilized in solvents such as volatile or nonvolatile silicones, or silicone compatible vehicles such as paraffinic hydrocarbons or esters. Suitable emulsifying silicone elastomers may include at least one polyalkyl ether or polyglycerolated unit.

Structuring agents may be used to increase viscosity, thicken, solidify, or provide solid or crystalline structure to the skin care composition. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents.

Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof. Silicone gums are another oil phase structuring agent. Another type of oily phase structuring agent includes silicone waxes. Silicone waxes may be referred to as alkyl silicone waxes which and are semi-solids or solids at room temperature. Other oil phase structuring agents may be one or more natural or synthetic waxes such as animal, vegetable, or mineral waxes.

The skin care compositions may be generally prepared by conventional methods such as known in the art of making compositions and topical compositions. Such methods typically involve mixing of ingredients in or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions are preferably prepared such as to optimize stability (physical stability, chemical stability, photostability, etc.) and/or delivery of active materials. The composition may be provided in a package sized to store a sufficient amount of the composition for a treatment period. The size, shape, and design of the package may vary widely. Certain package examples are described in U.S. Pat. Nos. D570,707; D391,162; D516,436; D535,191; D542,660; D547,193; D547,661; D558,591; D563,221; 2009/0017080; 2007/0205226; and 2007/0040306.

EXAMPLES

The present invention will be better understood by reference to the following examples which are offered by way of illustration not limitation.

Generally Applicable C-Map Methodology

Generating Instances

Individual experiments (referred to as batches) generally comprise 30 to 96 samples analyzed using Affymetrix GeneChip® technology platforms, containing 6 replicates of the vehicle control (e.g., DSMO), 2 replicate samples of a positive control that gives a strong reproducible effect in the cell type used, and samples of the test material/perturbagen. Replication of the test material is done in separate batches due to batch effects. In vitro testing was performed in 6-well plates to provide sufficient RNA for GeneChip® analysis (2-4 µg total RNA yield/well).

Human telomerized keratinocytes (tKC) were obtained from the University of Texas, Southwestern Medical Center, Dallas, Tex. tKC cells were grown in EpiLife® media with 1× Human Keratinocyte Growth Supplement (Invitrogen, Carlsbad, Calif.) on collagen I coated cell culture flasks and plates (Becton Dickinson, Franklin Lakes, N.J.). Keratinocytes were seeded into 6-well plates at 20,000 cells/cm² 24 hours before chemical exposure. Human skin fibroblasts (BJ cell line from ATCC, Manassas, Va.) were grown in Eagle's Minimal Essential Medium (ATCC) supplemented with 10% fetal bovine serum (HyClone, Logan, Utah) in normal cell culture flasks and plates (Corning, Lowell, Mass.). BJ fibroblasts were seeded into 6-well plates at 12,000 cells/cm² 24 hours before chemical exposure.

All cells were incubated at 37° C. in a humidified incubator with 5% $CO_2$. At t=-24 hours cells were trypsinized from T-75 flasks and plated into 6-well plates in basal growth medium. At t=0 media was removed and replaced with the appropriate dosing solution as per the experimental design. Dosing solutions were prepared the previous day in sterile 4 ml Falcon snap cap tubes. Pure test materials may be prepared at a concentration of 1-200 µM, and botanical extracts may be prepared at a concentration of 0.001 to 1% by weight of the dosing solution. After 6 to 24 hours of chemical exposure, cells were viewed and imaged. The wells were examined with a microscope before cell lysis and RNA isolation to evaluate for morphologic evidence of toxicity. If morphological changes were sufficient to suggest cytotoxicity, a lower concentration of the perturbagen was tested. Cells were then lysed with 350 ul/well of RLT buffer containing β-mercaptoethanol (Qiagen, Valencia, Calif.), transferred to a 96-well plate, and stored at -20° C.

RNA from cell culture batches was isolated from the RLT buffer using Agencourt® RNAdvance Tissue-Bind magnetic beads (Beckman Coulter) according to manufacturer's instructions. 1 µg of total RNA per sample was labeled using Ambion Message Amp™ II Biotin Enhanced kit (Applied Biosystems Incorporated) according to manufacturer's instructions. The resultant biotin labeled and fragmented cRNA was hybridized to an Affymetrix HG-U133A 2.0 GeneChip®, which was then washed, stained and scanned using the protocol provided by Affymetrix.

Example 1

This Example illustrates use of C-map to identify connections between perturbens and genes associated with a pigmentation condition, wherein the pigmentation condition is a hyperpigmentation condition. Specifically an analysis of tissue from the arms of individuals showing the hyperpigmentation condition Solar Lentigines (age spots) is compared to an analysis of tissue from full normal controls, and an expression signature is created as herein described through specific statistical comparisons, filtering, and sorting. The expression signature can then be used to implement a data architecture by providing a C-map query to identify relationships between perturbens and genes associated with a hyperpigmentation pigmentation condition.

Deriving a Hyperpigmentation Condition Expression Signature

RNA isolated from clinical samples was analyzed using the Affymetrix HG-U133 Plus 2.0 GeneChips, which contain 54,613 probe sets complementary to the transcripts of more than 20,000 genes. However, instances in the provided database used were derived from gene expression profiling experiments using Affymetrix HG-U133A 2.0 GeneChips, containing 22,214 probe sets, which are a subset of those present on the Plus 2.0 GeneChip. Therefore, in developing gene expression signatures from the clinical data, the probe sets were filtered for those included in the HG-U133A 2.0 gene chips.

A statistical analysis of the microarray data is performed to derive a plurality of hyperpigmentation gene expression signatures which may comprise a statistically relevant number of the up-regulated and down-regulated genes. In certain embodiments a hyperpigmentation gene expression signature includes between 10 and 400 up-regulated and/or between 10 and 400 down-regulated genes. In more specific embodiments a hyperpigmentation gene expression signature includes the 50 most statistically relevant up-regulated genes alone or in combination with the 50 most statistically relevant down-regulated genes. Regulation is determined in comparison to gene expression in normal cells.

a. Filtering based on Absent/Margin/Present Calls. This filter creates a list of potential genes for inclusion in the gene expression signature. For example, a suitable filter may be that at least 50% of the samples in one treatment group must have a Present call for each probe set. Present calls are derived from processing the raw GeneChip data and provide evidence that the gene transcript complementary to a probe set that is actually expressed in the biological sample. The probes that are absent from all samples are likely to be just noisy measurements. This step is important to filter out probe sets that do not contribute meaningful data to the signature. For hyperpigmentation gene expression signatures, the data was filtered for probe sets with at least 50% Present calls provided by the Affymetrix MAS 5 software.

b. Filtering According to a Statistical Measure. For example, a suitable statistical measure may be p-values from a t-test, ANOVA, correlation coefficient, or other model-based analysis. As one example, p-values may be chosen as the statistical measure and a cutoff value of p=0.05 may be chosen. Limiting the signature list to genes that meet some reasonable cutoff for statistical significance compared to an appropriate control is important to allow selection of genes that are characteristic of the biological state of interest. This is preferable to using a fold change value, which does not take into account the noise around the measurements. The t-statistic was used to select the probe sets in the signatures because it is signed and provides an indication of the directionality of the gene expression changes (i.e. up- or down-regulated) as well as statistical significance.

c. Sorting the Probe Sets. All the probe sets are sorted into sets of up-regulated and down-regulated sets using the statistical measure. For example, if a t-test was used to compute p-values, the values (positive and negative) of the t-statistic are used to sort the list since p-values are always positive. The sorted t-statistics will place the sets with the most significant p-values at the top and bottom of the list with the non-significant ones near the middle.

d. Creation of the Gene expression signature. Using the filtered and sorted list created, a suitable number of probe sets from the top and bottom are selected to create a gene expression signature that preferably has approximately the same number of sets chosen from the top as chosen from the bottom. For example, the gene expression signature created may have at least about 10, 50, 70, 100, 200, or 300 and/or less than about 800, 600, 400 or 100 genes corresponding to a probe set on the chip. The number of probe sets approximately corresponds to the number of genes, but a single gene may be represented by more than one probe set.

It is understood that the phrase "number of genes" as used herein, corresponds generally with the phrase "number of probe sets."

An exemplary Hyperpigmentation Condition Signature according to the invention is provided, wherein the hyperpigmentation condition is Solar Lentigines (Age Spots). Data is generated from an arm age spot genomics study, full spot tissue vs. full normal tissue comparison. Probe selection method for up-regulated probes: 1. mean expression value of spot tissue>200, 2. ratio of present call of spot tissue chips>=50%, 3. probe is significantly up regulated, p<0.05, 4. top 50, 100 and 200 probes ranked by p values, are selected respectively. Three signatures are generated using top up and down regulated probes cut at 50, 100 and 200, respectively. C-Map hit evaluation: hits are selected based on their average weight from three signatures. Probe selection method for down-regulated probes: 1. mean expression value of normal tissue>200, 2. ratio of present call of normal tissue chips>=50%, 3. probe is significantly down regulated, p<0.05, 4. Top 50, 100 and 200 probes ranked by p values, are selected respectively. The illustrative signature is set forth as FIG. 2, Tables B and C.

Example 2

This Example provides support for the use of benchmark signatures in a C-map query to generate putative agents. The Example specifically outlines generation of a benchmark skin pigmentation-modifying gene expression signature. As described herein, the benchmark skin pigmentation-modifying gene expression signature was generated using methods such as filtering as described in Example 1. More specifically, Hexamidine, N-acetyl glucosamine, Niacinamide, or SEPIWHITE (Sepiwhite is the purported tradename of the agent known as undecylenoyl phenylalanine) are applied as described below to tert-Keratinocyte cells to generate the benchmark skin pigmentation-modifying gene expression signature.

A. Hexamidine (hex).

A tert-Keratinocyte (tKC) cell line is used to conduct the genomics study with an Affy U133A chip. (a) Probe selection method for up-regulated probes: 1. mean expression value of hex treated>200, 2. ratio of present calls of hex treated chips>=50%, 3. up regulated by hex, but down regulated by MSH (a skin darkening agent), 4. hex treated p<0.05, top 100 probes ranked by p value; (b) Probe selection method for down regulated probes, 1. mean expression value of DMSO control>200, 2. ratio of present calls of DMSO control chips>=50%, 3. down-regulated by hex, but up-regulated by MSH (a skin darkening agent), 4. hex treated p<0.05, top 100 probes ranked by p value. The illustrative signatures are set forth as FIGS. 10 and 11, Tables D and E, respectively.

B. N-acetyl-glucosamine (NAG).

tKC cell line, Affy U133A chip; Probe selection method for up-regulated probes: 1. mean expression value of NAG treated>200, 2. ratio of present calls of NAG treated chips>=50%, 3. up regulated by NAG, but down regulated by MSH (a skin darkening agent), 4. NAG treated p<0.05, 39 probes are selected. Probe selection method for down-regulated probes: 1. mean expression value of DMSO control>200, 2. ratio of present calls of DMSO control chips>=50%, 3. down regulated by NAG, but up regulated by MSH (a skin darkening agent), 4. NAG treated p<0.05, 43 probes are selected. The illustrative signatures are set forth as FIGS. 12 and 13, Tables F and G, respectively.

C. Niacinamide.

The Niainamide signature was generated by filtering analogous to that used for hexamidine or NAG was used. The illustrative signatures are set forth as FIGS. 14 and 15, Tables H and I, respectively.

D. Sepiwhite.

The Sepiwhite signature was generated by filtering analogous to that used for hexamidine or NAG was used. The illustrative signatures are set forth as FIGS. 16 and 17, Tables J and K, respectively.

Example 3

This Example illustrates use of C-map and the generation of a signature as described in Example 2; however Example 3 outlines development of a composite "skin tone" signature where Niacinaminde, Sepiwhite, NAG, and Hexamidine are used together to generate a signature. This Example illustrates generation of an exemplary composite "skin tone" Signature comprised of four benchmark skin-lightening agents: Niacinamide, Sepiwhite, NAG, and Hexamidine. Chips Used for Signature Generation: DMSO control chips used for Signature generation: Conditions for Signature Generation: 1. a probe must have 10% present call among Control chips or BenchMark chips, 2. The average signal for an up-regulated probe on the treated chip must be >200, 3. The average signal for a down-regulated probe on the control chip must be >200, 4. A probe must be up or down-regulated cross all benchmark chips. Table Headers: Average signal of all control chips, AvgFC, AvgSignal-Treated: Average signal of all treated chips, Average fold change, AvgSignalControl. The illustrative signature is set forth as FIG. 18, Table L.

This Example supports embodiments outlining how a composite signature may be generated by treating a cell sample with more than one agent. As indicated earlier, a composite signature can be added in two ways: cells can be treated with each agent separately, the signature can be generated by comparing regulated genes from all agents (together), looking for genes regulated in the same direction by all agents; secondarily, agents can be mixed together prior to treatment of cells. In another embodiment, a composite benchmark signature may be generated for a skin-lightening agent, and another generated for a skin darkening agent. The signature for the skin-lightening agent may be further tweaked by eliminating any gene from the signature that also appears in the signature of the skin-darkening agent, regulated in the same direction, or vice versa. The inventors discovered that such composite signatures are particularly useful for mining C-map for agents capable of modifying skin pigment in the desired direction.

Example 4

This Example illustrates use of C-map and the generation of a signature. More specifically, the signature was generated through application of Retinoic acid to fibroblasts and keratinocytes. This Example illustrates a method for generating a benchmark skin tone agent signature according to the invention in each of two different cell types for comparison of the C-map hit evaluations, wherein the benchmark skin active agent is Retinoic acid ("RA") and the cell types are (a) fibroblast, and (b) keratinocyte.

(a) Tert-keratinocytes (tKC) RA Signatures. Cells were treated with 1 uM tRA for 6 hr, tested in triplicate, with triplicate DMSO controls, and analyzed on HG-U133A GeneChips; Signatures were generated like for BJ fibroblasts, below; the signature KC_RA_200 consists of 100 most significant up- and 100 most significant down-regulated probe sets; the signature KC_RA_400 consists of 200 most significant up- and 200 most significant down-regulated probe sets.

(b) Fibroblast RA Signatures. The selected cell type is BJ fibroblast. Cells were treated with 1 uM tRA for 6 hr, tested in triplicate, with triplicate DMSO controls, and analyzed on HG-U133A GeneChips. Present calls>0 for naïve, DMSO and RA (9 samples total). Mean signal>=200 for DMSO OR RA samples t-test p<0.05; Filtered for minimum fold change up or down of 1.2; Used log fold change to establish directionality and sorted up and down lists by t-test p value. The signature BJ_RA_200 consists of 100 most significant up- and 100 most significant down-regulated probe sets; The signature BJ_RA_400 consists of 200 most significant up- and 200 most significant down-regulated probe sets. The illustrative signatures are set forth as FIGS. 19, 20, 21, AND 22, Tables M, N, O and P respectively.

Example 5

This example summarizes representative potential skin-lightening agents and C-map query results for the benchmark skin active agent all-trans-retinoic acid according to the invention. C-map was queried using the Retinoic Acid/Keratinocyte 200 benchmark signature. The average C-map scores for the top scoring known skin lightening agents are tabled. Retinoic acid had the highest score of the materials tested because it was used to generate the signature. The data shown are for teleomerized human keratinocytes (tKC). Average CMap scores for some skin lightening agents with the Retinoic Acid Keratinocyte RA_200 Signature are shown in FIG. 23, Table Q.

Example 6

This Example provides evidence of the advantages of using composite signatures and illustrates clinical affirmation of the C-map model for predicting efficacy of skin-lightening agents. This Example supports embodiments related to composite signatures (as described at the end of Example 3). An illustrative "Skin Tone" Signature developed from a genomics study using a composite skin-lightening benchmark agent signature is derived from Niacinamide, Hexamidine, Sepiwhite, and NAG. The signature is used to query C-map and generate a list of potential skin-lightening agents. A top hit, Chlorhexidine Diactate (CD) is entered into clinical testing for confirmation of efficacy. The control for clinical efficacy is a 5% Niacinamide+1% Sepiwhite formulation in the control vehicle.

Primary endpoints are changes in color spot area fraction (image analysis) and melanin spot area fraction (NC2) from baseline. Secondary endpoints are changes from baseline in L*a*b (color image analysis), mean melanin gray scale (NC2), and melanin evenness (NC2). Texture area fraction and pore area fraction are also evaluated to explore impact on other aspects relating to overall skin tone. Statistical significant superiority to the vehicle at one of these time points is a project success criteria. Statistically significant superiority to the high efficacy benchmark skin active agent to vehicle performance is the clinical success criteria.

Study Design: The experimental protocol included a 9-week (1-week preconditioning & 8-week treatment), randomized, double-blind, round robin, vehicle-controlled, split-face tone benefit study. The subject population included 330 Chinese females, 25-55 years old with hyperpigmented spots. 318 subjects completed the entire study. Pre-conditioning was achieved with application of Nature Science Deep Purify cleanser and study-specific moisturizer for a week. Olay Complete SPF 15 UV Moisturizing Lotion is concomitantly used during pre-conditioning and treatment. 0.5 g each test product per half-face (forehead to jaw line; ~4 mg/cm$^2$) is dosed 2× a day (morning/evening). Color SAF and treatment area, Melanin SAF, gray scale, evenness by NC2, and additional measurement of Fine Lines and Wrinkle and Texture are by REAL 3.01A. Data collection points include baseline, and ends of weeks 4, 6 and 8. The tested hypothesis is that there is no difference in clinical endpoint versus the benchmark composition treatment. Study site is Kuntai Clinical Center, Beijing, China and study time frame is February 2010 (pre-conditioning) to April 2010.

0.05% Chlorhexidine Diacetate in SC-99 vehicle (7% glycerin) was a top connectivity hit using the tone composite benchmark signature query set forth as Example 3 and is tested for clinical efficacy with respect to four different tone criteria against a known high efficacy benchmark composition of 5% Niacinamide and 1% Sepiwhite in SC-99 vehicle. Results:

According to the spot area fraction color test: 0.05% CD showed significantly fewer spots when compared to vehicle at week 8. In the spot area fraction NC2 test, CD showed a significantly reduced fraction when compared to the vehicle at both weeks 6 and 8. In the NC2 Melanin evenness test, CD demonstrated superiority to the vehicle at weeks 6 and 8, and with respect to Basal skin tone, CD demonstrated superiority at week 8. Surprisingly, CD also demonstrated superior efficacy in the Pore area and Texture area fractions when compared to the vehicle at week 8, suggesting that it is a good candidate for overall skin tone and texture enhancement.

Example 7

This Example provides support for the unexpected effectiveness of composite signature use with the C-map technology, with this Example illustrating a comparison of expression signature efficacy in predicting inhibitors; specifically, from 33 various chemicals identified as melanogenesis inhibitors in the mouse B16 melanoma cell assay (FIG. 24, Table R). The composite signature was unexpectedly more effective at identifying inhibitors than any of the individual signatures (such as for Niacinamide, NAG, Hexamidine, or Sepiwhite). For this analysis C-map hits were defined as materials occurring in the top 200 instances (from the same pool of 2266 instances) with a score≥0.30. Result Summary of correctly predicted melanogenesis inhibitors: Composite signature: 20, Niacinamide: 1, NAG: 1, Hexamidine: 2, and Sepiwhite: 9. The C-map scores shown in Table R are average scores across the instances of the chemicals. A maximum positive C-map score is 2.0 indicating perfect positive connectivity. The individual materials do not show perfectly high scores linking to themselves because of replicate variability, which is more evident for materials with relatively weak effects on gene expression. Surprisingly, for this set of materials the composite signature in 3 of 4 cases gave better scores with the benchmark materials than the individual benchmark signatures. The process of generating the benchmark signature may select for the most consistently regulated probe sets, which may account for this result.

As indicated in Example 3, this Example (7) supports embodiments outlining how a composite signature may be generated by treating a cell sample with more than one agent. As indicated earlier, a composite signature can be added in two ways: cells can be treated with each agent separately, the signature can be generated by comparing regulated genes from all agents (together), looking for genes regulated in the same direction by all agents; secondarily, agents can be mixed together prior to treatment of cells. In another embodiment, a composite benchmark signature may be generated for a skin-lightening agent, and another generated for a skin darkening agent. The signature for the skin-lightening agent may be further tweaked by eliminating any gene from the signature that also appears in the signature of the skin-darkening agent, regulated in the same direction, or vice versa. The inventors discovered that such composite signatures are particularly useful for mining C-map for agents capable of modifying skin pigment in the desired direction.

Example 8

This Example provides support to illustrate that it is believed that keratinocyte cells, rather than melanocyte or melanoma cells, have exhibited a more robust transcriptional profile when treated with skin-lightening agents. Keratinocytes have been preliminarily shown to be easier to grow than melanocytes and have increased responsiveness such that keratinocytes may be able to be used to detect active chemicals over a wider range of concentrations than testing with melanocytes. More specifically, in this Example, six skin tone benchmark materials were applied to each of three cell types (tert-keratinocytes, melanocyes, and melanoma cells), and with four of six tested materials tert-keratinocytes showed the greatest response (as indicated in FIG. 25, Table S which shows that with four of the six tested materials, the number of probe sets with significant P-values compared to DMSO controls was greatest for tert-keratinocytes). As can be seen in Table S, The six tested skin tone benchmark materials included: Haxamidine diisothionate, Myo-inositol, N-acetyl-glucosamine, NDP-MSH, Niacinamide, and Sepiwhite. For completeness, details of the exact types of melanocytes and melanoma cells, as well as the cell culturing conditions and result analysis are provided herein below.

HEMn primary neonatal medium pigment melanocytes were obtained from Invitrogen, Carlsbad, Calif. and were cultured in Medium 254 from Invitrogen. HBL melanoma cells were obtained from the Laboratory of Oncology and Experimental Surgery, Institut Bordet, Université Libre de Bruxelles, Belgium and were cultured in F-10 Nutrient Mixture (Ham) from Invitrogen supplemented with 10% fetal bovine serum (HyClone, Logan, Utah). Human telomerized keratinocytes (tert-keratinocytes) were obtained from the University of Texas, Southwestern Medical Center, Dallas, Tex. and were grown in EpiLife® media with 1× Human Keratinocyte Growth Supplement (Invitrogen). All cells were incubated at 37° C. in a humidified incubator with 5% CO2.

Cells were seeded into 6-well plates a 24 hours before chemical exposure, and the skin tone benchmark chemicals listed in the table below were added to culture medium dissolved in DMSO. The final concentration of DMSO was 0.1%, and cells treated just with DMSO served as controls. After 6 hours of chemical exposure cells were then lysed with 350 ul/well of RLT buffer containing β-mercaptoethanol (Qiagen, Valencia, Calif.), transferred to a 96-well plate, and stored at −20° C. RNA from cell culture batches was isolated from the RLT buffer using Agencourt® RNAdvance Tissue-Bind magnetic beads (Beckman-Coulter, Brea Calif. 92821) according to manufacturer's instructions. 1 ug of total RNA per sample was labeled using Ambion Message Amp™ II Biotin Enhanced kit (Life Technologies, Grand Island, N.Y. 14072) according to manufacturer's instructions. The resultant biotin labeled and fragmented cRNA was hybridized to an Affymetrix HG-U133A 2.0 GeneChip®, which was then washed, stained and scanned using the protocol provided by Affymetrix.

Regarding the results and analysis of the testing: Two sample t-tests were performed on each treatment to compare with the DMSO control. The number of probe sets with significant p-values (<0.05) are summarized in the table below. Each GeneChip® contains 22215 probes sets. Using a significance level of 0.05, 1111 probe sets (95% confidence interval of 1047 to 1174) are expected to be significant by chance alone. This estimate is somewhat conservative since there may be multiple probe sets for the same gene.

In summary, the tert-keratinocytes were generally the most responsive cells to the skin tone benchmark materials. There were more significantly regulated probe sets for 4/6 skin tone benchmark materials in the tert-keratinocytes compared to either HeMnMP melanocytes or HBL melanoma cells. The tert-keratinocytes have an additional advantage over the second most responsive cells, HeMnMP melanocytes, in that they grow substantially faster and are more practical cell line for routine screening.

Every document cited herein is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent any meaning or definition of a term in this document conflicts with any meaning or definition of the same term in a document incorporated by reference, the meaning or definition assigned to that term in this document shall govern.

The values disclosed herein are not to be understood as being strictly limited to the exact numerical values recited. Instead, unless otherwise specified, each such value is intended to mean both the recited value and a functionally equivalent range surrounding that value.

The present invention should not be considered limited to the specific examples described herein, but rather should be understood to cover all aspects of the invention. Various modifications, equivalent processes, as well as numerous structures and devices to which the present invention may be applicable will be readily apparent to those of skill in the art. Those skilled in the art will understand that various changes may be made without departing from the scope of the invention, which is not to be considered limited to what is described in the specification.

What is claimed is:

1. A method of generating a gene expression signature for use in identifying connections between perturbagens and genes associated with a skin pigmentation condition, the method comprising:

a) generating a gene expression profile for a human keratinocyte or fibroblast sample treated with at least one benchmark skin pigmentation modifying agent, wherein the benchmark skin pigmentation modifying agent includes a skin lightening agent suspended in a vehicle composition;

b) generating a gene expression profile for a human skin cell sample treated with the vehicle composition, wherein generating the gene expression profiles in at least one of (a) and (b) comprises
   i. isolating RNA from the human skin cell sample(s), and
   ii. creating cDNA from the isolated RNA,
   iii. creating cRNA from the cDNA, and
   iv. hybridizing the cRNA to a microarray to obtain microarray data; and c) comparing the expression profiles of (a) and (b) to identify a set of genes differentially expressed in (a) and (b), wherein the comparison step comprises
   i. statistically analyzing the microarray data to identify differentially expressed genes,
   ii. assigning a p-value to each of the differentially expressed genes, and
   iii. discarding differentially expressed genes that have a p-value of greater than 0.05;

d) rank ordering the differentially expressed gene set by p-value according to the direction of differential expression, wherein the rank ordered genes reflect the most up-regulated to the most down-regulated genes;

e) selecting from 10 to 800 of the most up-regulated and down-regulated differentially expressed genes based on p-value to provide a first gene expression signature list;

f) repeating steps (a) to (e) to provide a second gene expression signature list, wherein the skin lightening agent is replaced with a skin darkening agent;

g) comparing the first gene expression signature list to the second gene expression signature list and eliminating from the first gene expression signature list any genes that have the same direction of differential expression in the first and second lists to provide a third gene expression signature list; and h) storing the third gene expression signature list on a computer readable medium.

2. The method of claim 1, wherein the benchmark skin pigment modifying agent comprises an agent selected from the group consisting of a melanocyte stimulation inhibitor, an anti-inflammatory agent, an alpha-MSH pigment induction antagonist, a melanophage dermal residence time suppressor, a melanin synthesis-associated enzyme inhibitor, a melanosome transport inhibitor, a vitamin B3 compound, hexamidine diisothionate, Myo-inositol, N-acetyl-glucosamine (NAG), NDP-MSH, an N-acyl amino acid compound, a retinoid compound, hexyldecanol, hydroquinone and combinations thereof.

3. The method of claim 1, further comprising assigning an identifier to each gene in the gene expression profile, wherein the identifiers are selected from the group consisting of gene names, gene symbols, and microarray probe set IDs.

4. The method of claim 1, where the cRNA is labeled with biotin.

* * * * *